(12) United States Patent
Canne et al.

(10) Patent No.: US 7,094,871 B2
(45) Date of Patent: *Aug. 22, 2006

(54) SOLID PHASE NATIVE CHEMICAL LIGATION OF UNPROTECTED OR N-TERMINAL CYSTEINE PROTECTED PEPTIDES IN AQUEOUS SOLUTION

(75) Inventors: Lynne Canne, Pacifica, CA (US); Stephen B. H. Kent, San Francisco, CA (US); Reyna Simon, Los Gatos, CA (US)

(73) Assignee: Gryphon Therapeutics, South San Francisco, CA (US)

( * ) Notice: Subject to any disclaimer, the term of this patent is extended or adjusted under 35 U.S.C. 154(b) by 698 days.

This patent is subject to a terminal disclaimer.

(21) Appl. No.: 09/987,655

(22) Filed: Nov. 15, 2001

(65) Prior Publication Data

US 2002/0132975 A1 Sep. 19, 2002

Related U.S. Application Data

(62) Division of application No. 09/097,094, filed on Jun. 12, 1998, now Pat. No. 6,326,468.
(60) Provisional application No. 60/049,553, filed on Jun. 13, 1997.

(51) Int. Cl.
C07K 1/02 (2006.01)

(52) U.S. Cl. ........................ 530/334; 530/326; 530/333; 530/339; 530/350; 530/402; 435/283.1; 525/54.1

(58) Field of Classification Search ................. 530/334, 530/326, 333, 339, 350, 402; 435/283.1; 525/54.1
See application file for complete search history.

(56) References Cited

U.S. PATENT DOCUMENTS 6,326,468 B1 * 12/2001 Canne et al. ............... 530/333

FOREIGN PATENT DOCUMENTS

WO    WO 96/34878    11/1996
WO    WO 98/28434    7/1998

OTHER PUBLICATIONS

Aimoto, "Synthesis of Phosphorylated Calmodulin–binding Site of Ca2+/Calmodulin–dependent Protein Kinase IICAMII by a Thioester Method," Chemical Abstracts, vol. 125, No. 1, Abstract No. 11415, (1996).
Akaji, et al., "Stiudies On Peptides. CXXVII. Synthesis Of A Tripentacontapeptide With Epidermal Growth Factor Activity," Chem. Pharma. Bull. (Tokyo) 33:184–102 (1985).
Atherton, et al., "Solid Phase Fragment Condensation—The Problems," In Innovation and Perspective In Solid Phase Synthesis, R. Epton, et al. Eds., pp. 11–25 (1990).
Ball, et al., "Affinity Purification Of 101 Residue Rat Cpn 10 Using A Reversible Biotinylated Probe," J. Pept. Sci., 1:288–294 (1995).
Blake, "Total Synthesis Of S–Carbamoylmethyl Bovine Apocytochrome C By Segment Coupling," Int. J. Pept. Protein Res., 27:191–200 (1986).
Canne, et al., "Synthesis Of Versatile Purification Handle For Use With Boc Chemistry Solid Phase Peptide Synthesis," Tetrahedron Letters, 38(19):3361–3364 (1997).
Canne, "Extending the Applicability of Native Chemical Ligation," J. Am. Che. Soc., vol. 118:5891–5896 (1996).
Canne, "A General Method For The Synthesis Of Thioester Resin Linkers For Use In The Solid Phase Synthesis Of Peptide–α–Thioacids," Tetrahedron Letters, 36(8):1217–1220 (1995).
Cheng, et al., "Chemical Synthesis of Human β–Endorphin(1–27) Analogs By Peptide Segment Coupling," Int. J. Pept. Prot. Res., 38:70–78 (1991).
Dawson, et al., "Synthesis Of Proteins By Native Chemical Ligation," Science, 266:766–799 (1994).
Funakoshi, et al., "Chemoselective One–Step Purification Method For Peptides Synthesized by the Solid Phase Technique," Proc. Natl. Acad. Sci. USA, 88:6981–6985 (1991).
Funakoshi, et al., "Affinity Purification Method Using Reversible Biotinylating Reagent For Peptides Synthesized By The Solid–Phase Technique," J. Chromatog., 638:21–27 (1995).
Garcia–Echeverria, et al., "One The Use of Hydrophobic Probes In The Chormatographic Purification Of Solid––Phase–Synthesized Peptides," J. Chem. Soc. Chem. Commun., 779–780 (1995).
Hojo, "Development of a Linker With an Enhanced Stability for the Preparation of Peptide Thioesters and Its Application to the Synthesis of a Stable–Isotope–Labelled HU–Type DNA–Binding Protein," Bull. Chem. Soc. Japan, 66(9):2700–2706 (1993).
Hojo, et al., "Protein Synthesis Using S–Alkyl Thioester Of Partially Protected Peptide Segments, Synthesis of DNA–Binding Domain of c–Myb Protein (142–193)–NH$_2$," Bull. Chem. Soc. Japan, 65:3055–3063 (1992).

(Continued)

Primary Examiner—Anish Gupta
(74) Attorney, Agent, or Firm—Jeffrey I. Auerbach; Liniak, Berenato & White

(57) ABSTRACT

The present invention provides methods, apparatus and kits for synthesizing assembled peptides and proteins on a solid phase with sequential ligation of three or more unprotected peptide segments using chemoselective and mild ligation chemistries in aqueous solution. Also provided are methods of monitoring solid phase sequential ligation reactions using MALDI or electrospray ionization mass spectrometry of reaction products.

20 Claims, 31 Drawing Sheets

OTHER PUBLICATIONS

Hojo, et al., "Polypeptide Synthesis Using the S–Alkyl Thioester of a Partially Protected Segment: Synthesis of the DNA–Binding Domain of c–Myb Protein (142–193)–NH$_2$," *Bull. Chem. Soc. Japan*, 64:111–117 (1991).

Janssen, "Thiolo, Thiono, and Dithio Acids and Ester," Chapter 15, *The Chemistry of Carboxylic Acids and Esters* (1969).

Liu, et al., "Peptide Segment Ligation Strategy Without Use Of Protecting Groups," *Proc. Natl. Acad. Sci. USA*, 91:6584–6588 (1994).

Muramatsu, et al., "Localization of Heparin–Binding, Neurite Outgrowth and Antigenic Regions In Midkine Molecule," *Biochem. And Biophys. Res. Comm.*, 203(2):1131–1139 (1994).

Rose, et al., "Facile Synthesis Of Homogeneous Artificial Proteins," *J. Am. Chem. Soc.*, 116:30–34 (1994).

Schnolzer, et al., "Constructing Proteins By Dovetailing Unprotected Synthetic Peptides: Backbone–Engineered HIV Protease," *Science*, 256:221–225 (1992).

Tam, et al., "Peptide Synthesis Using Unprotected Peptides Through Orthogonal Coupling Methods," *Proc. Natl. Acad. Sci. USA*, 92:12485–12489 (1995).

* cited by examiner

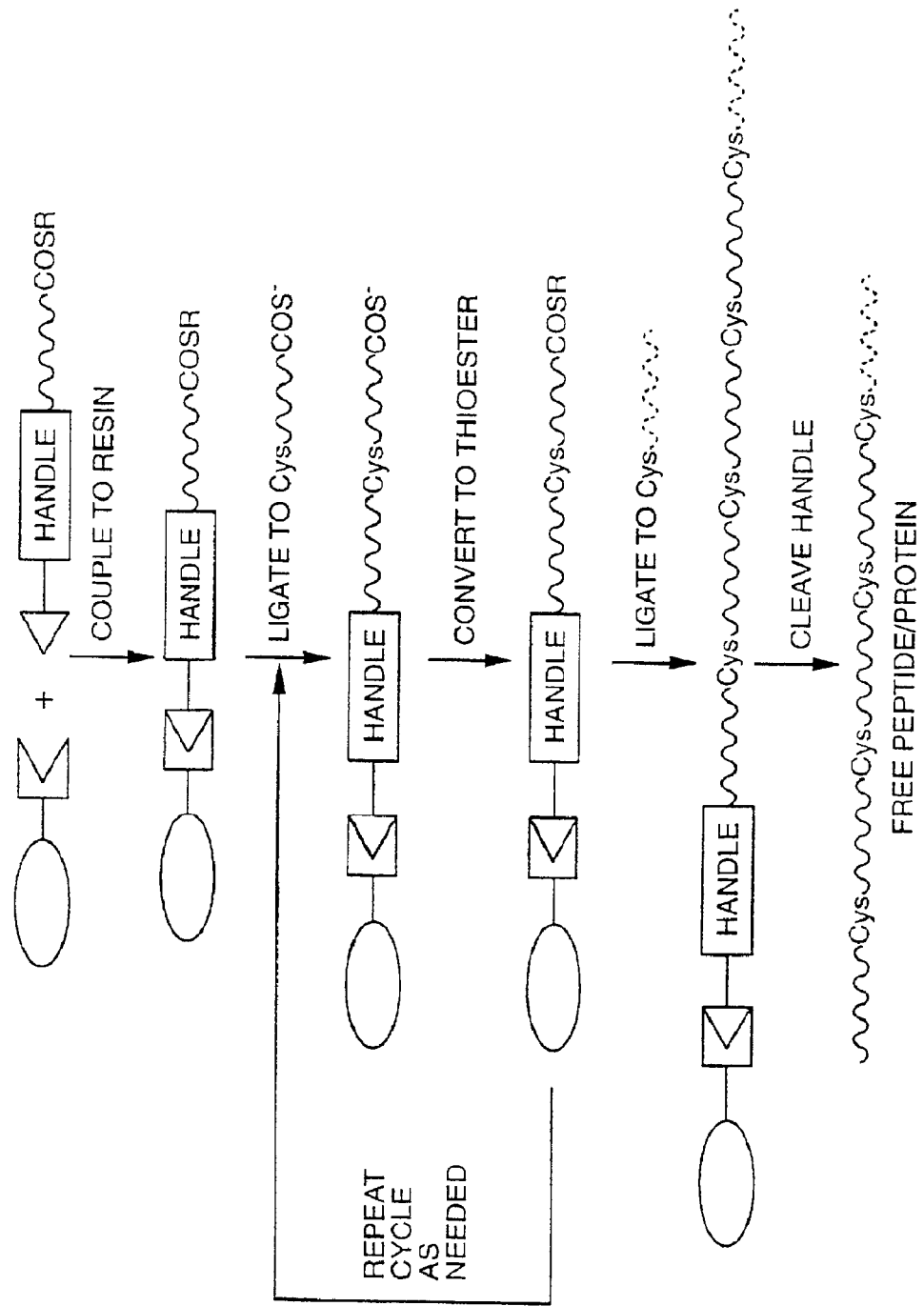
Scheme 1 Solid Phase Protein Synthesis
Native Chemical Ligations in an N- to C- Terminal Direction
FIG._1

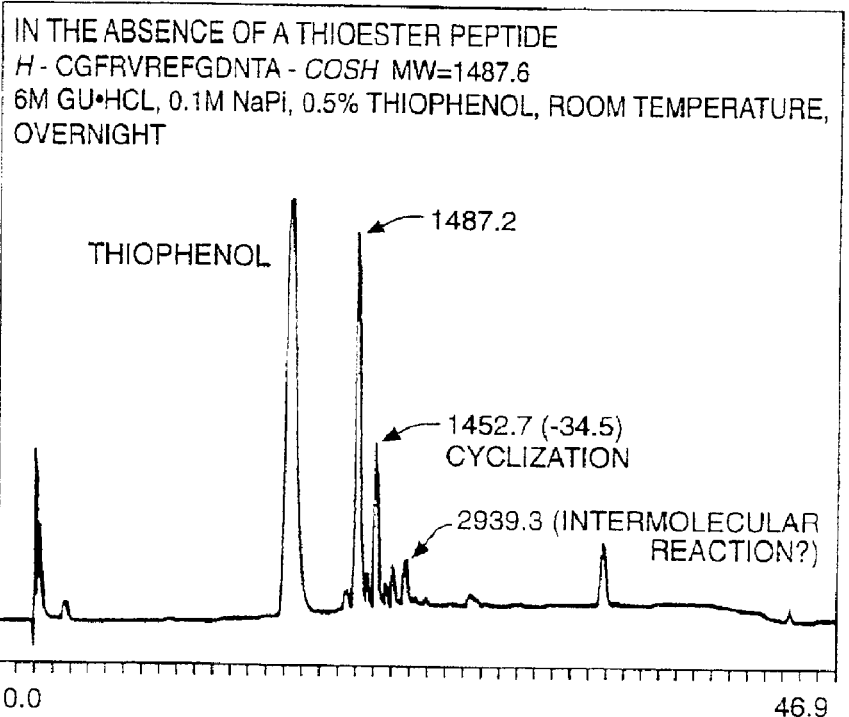
FIG._2A
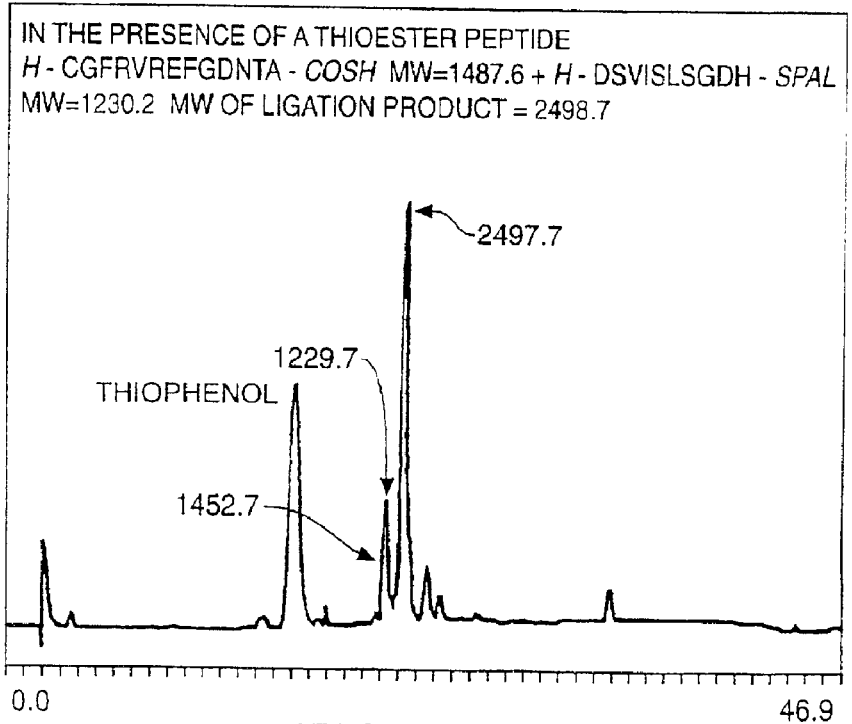
FIG._2B
Cys +COSR Stability Under Ligation Conditions

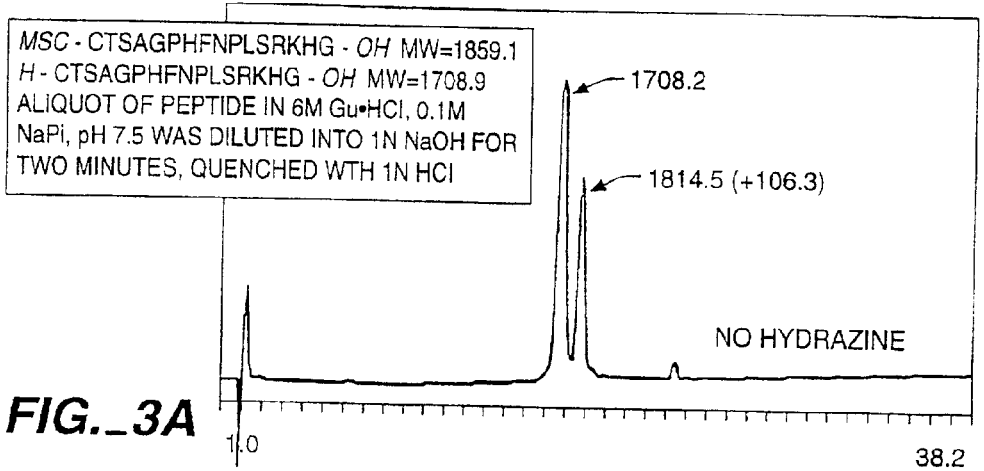
*FIG._3A*
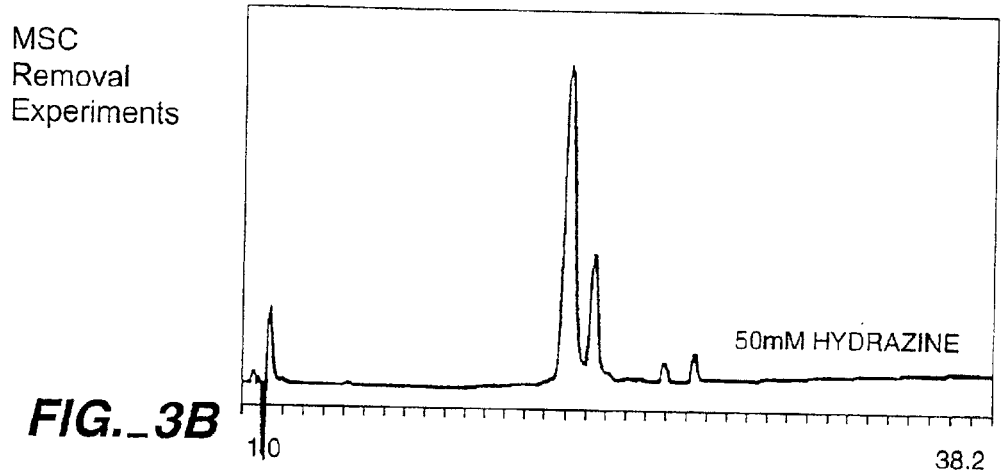
*FIG._3B*
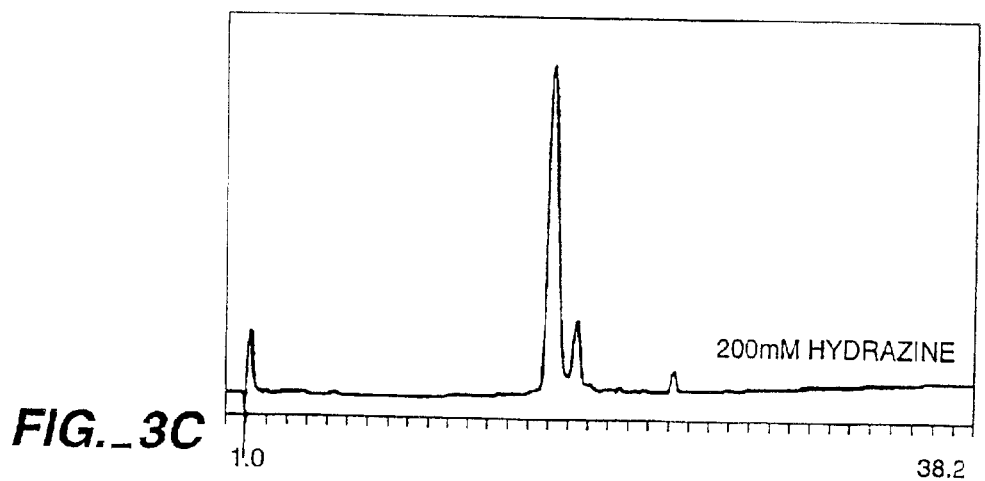
*FIG._3C*

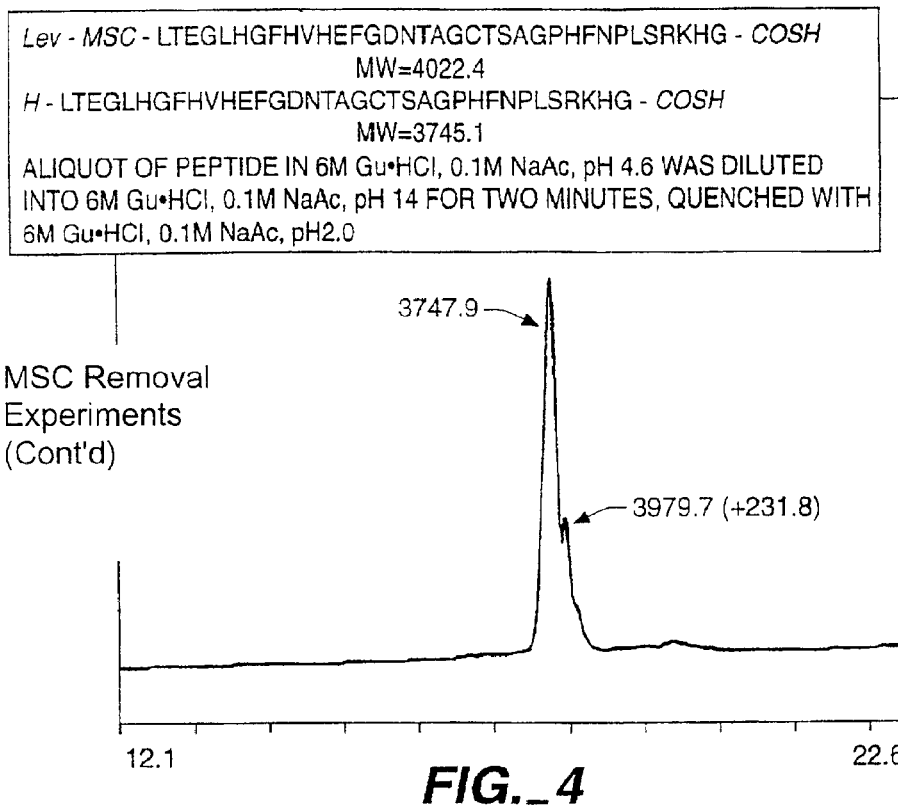
FIG._4
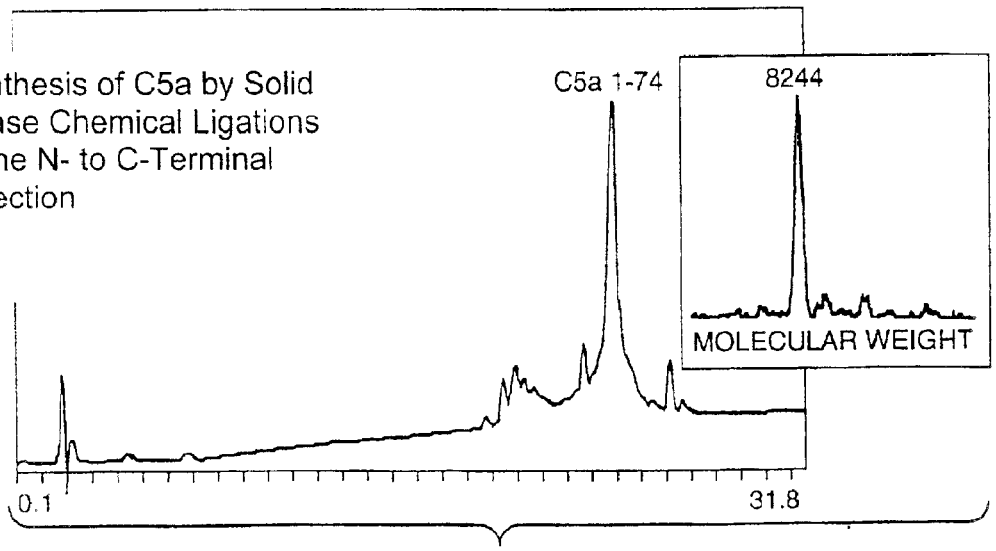
FIG._26

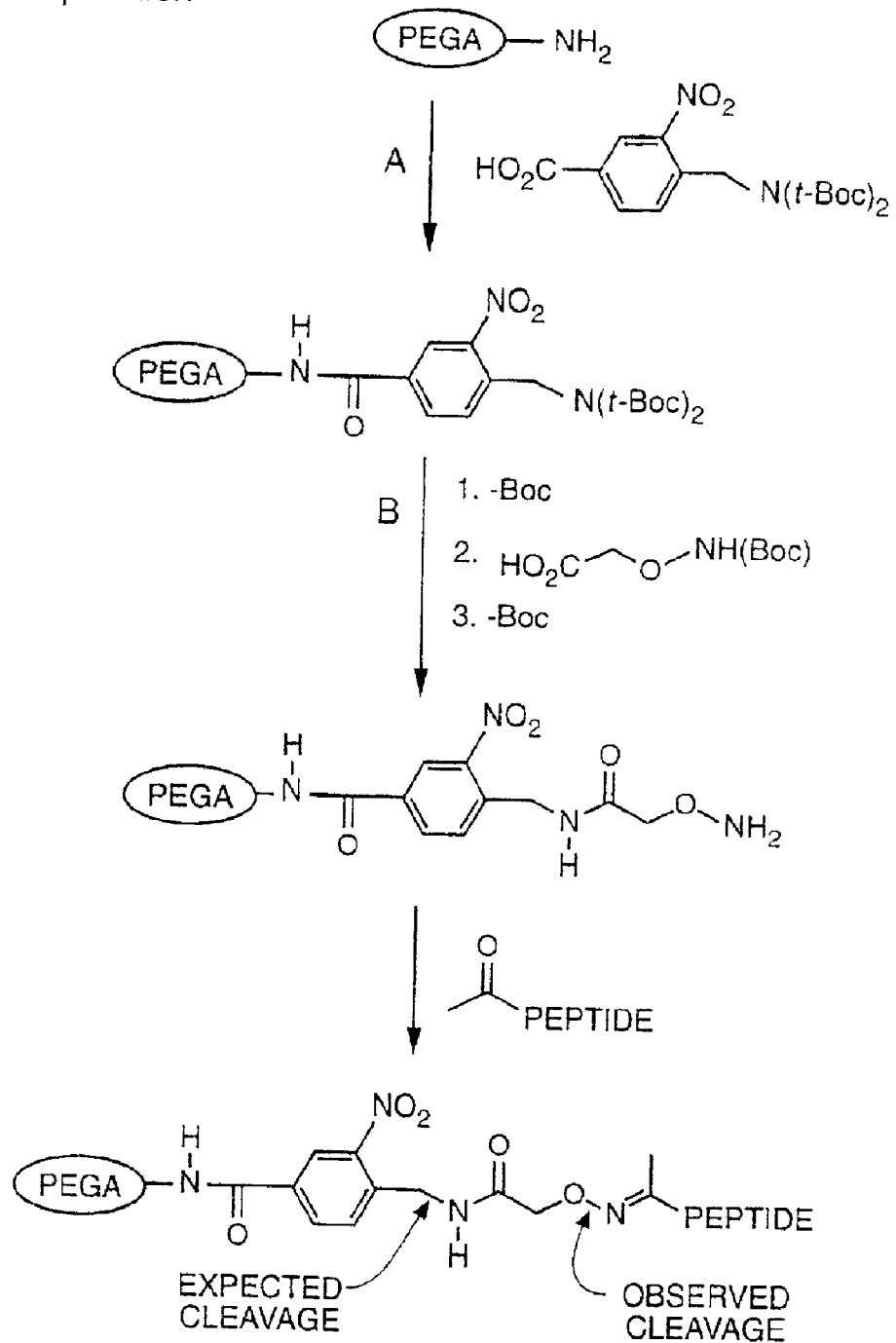
FIG._5A

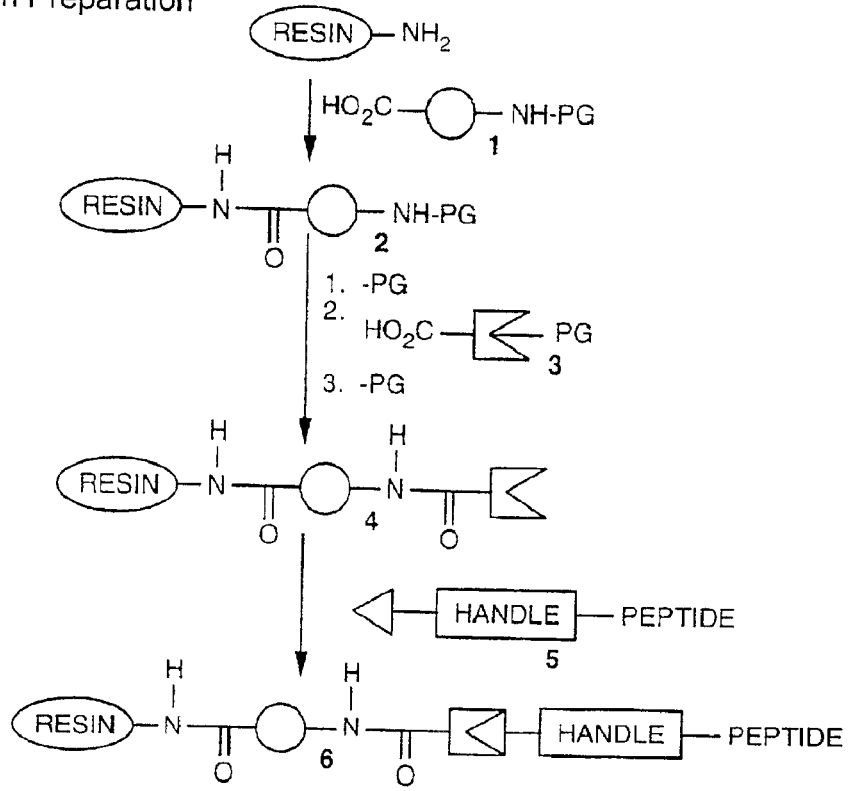
FIG._5B

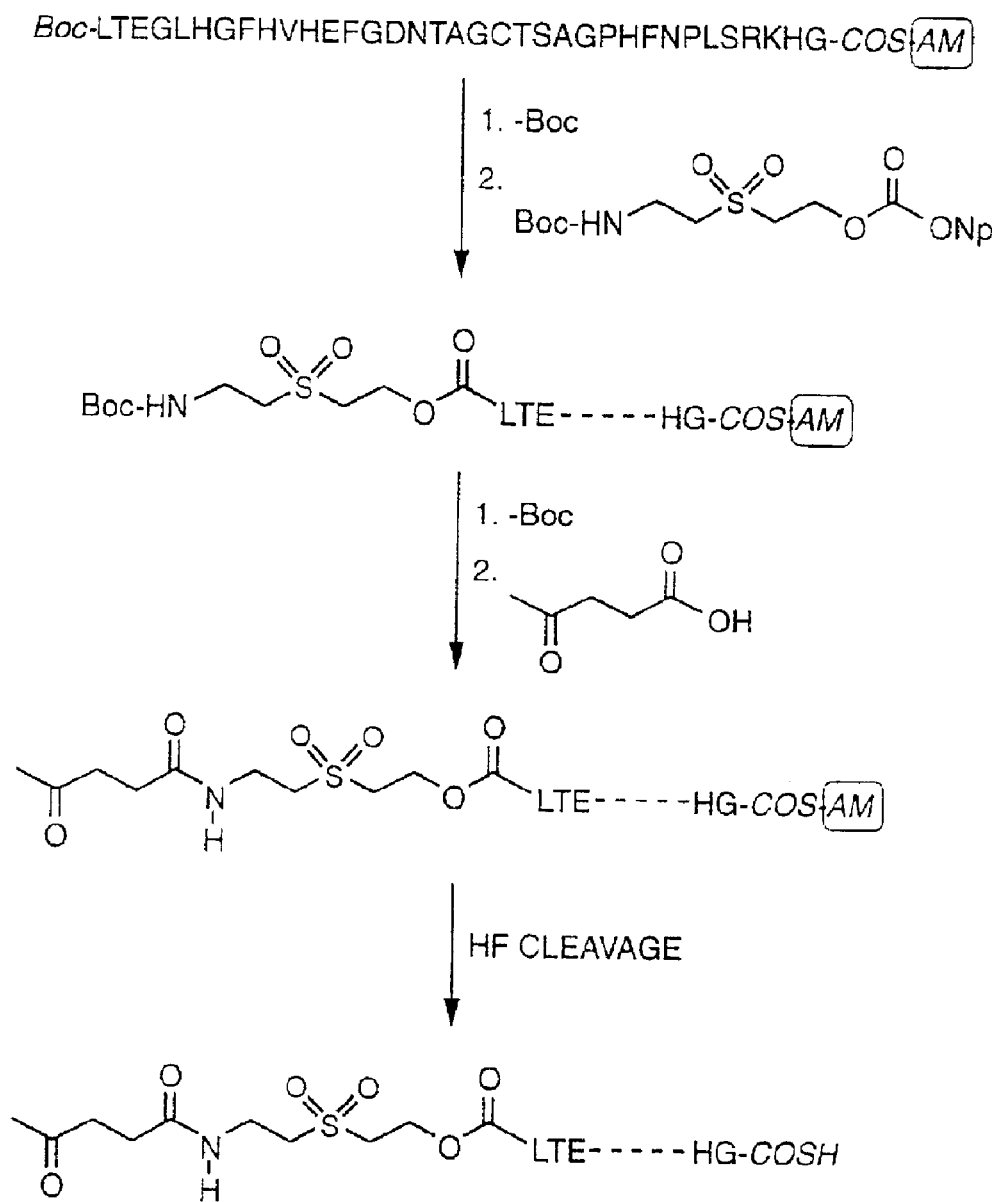
FIG._6
Derivatization of Segment 1
(N-terminal)

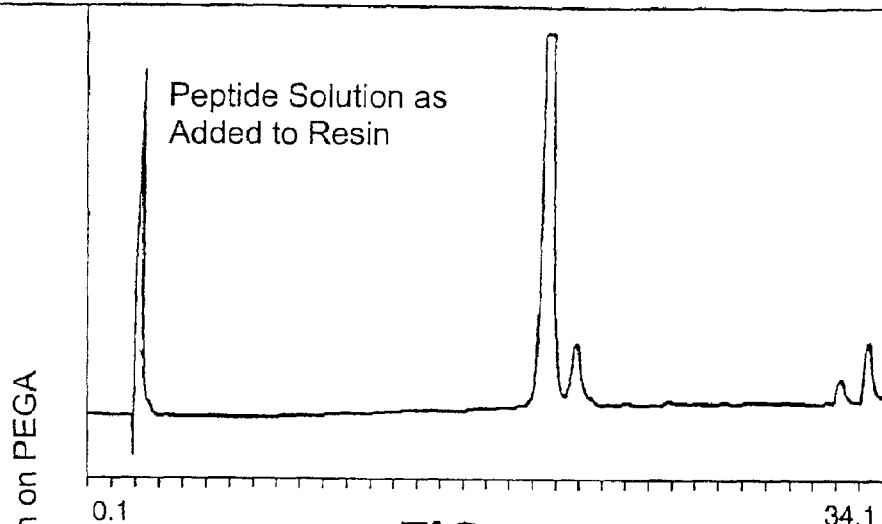
FIG._7A
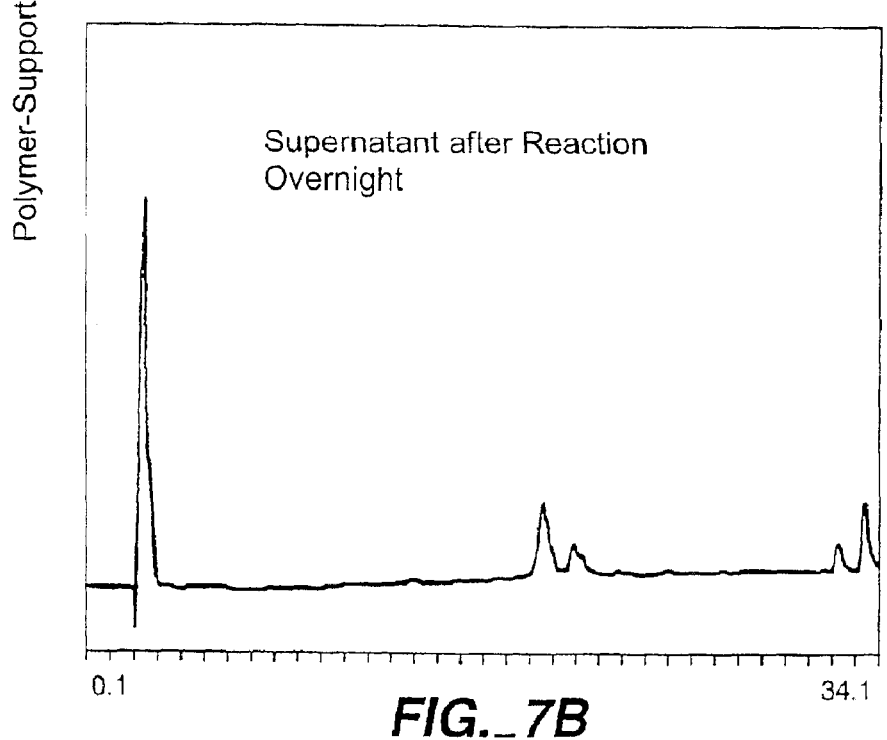
FIG._7B

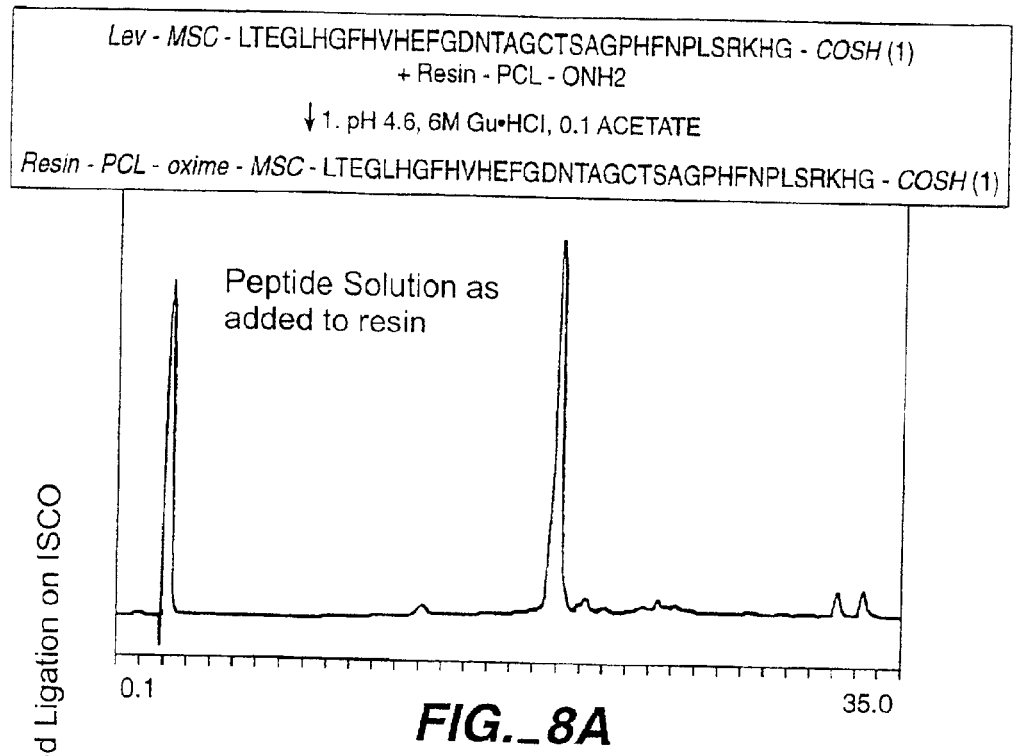
FIG._8A
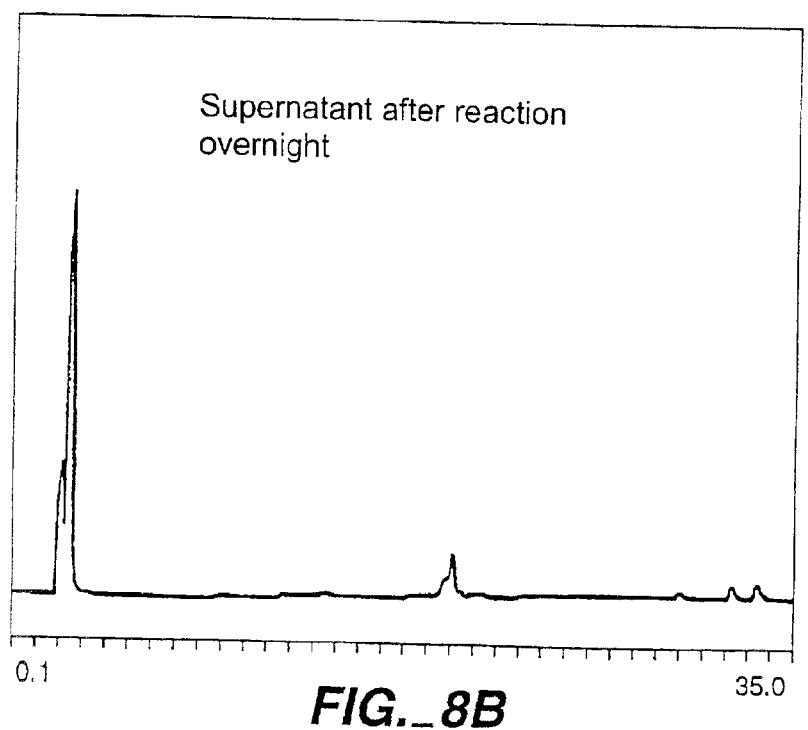
FIG._8B

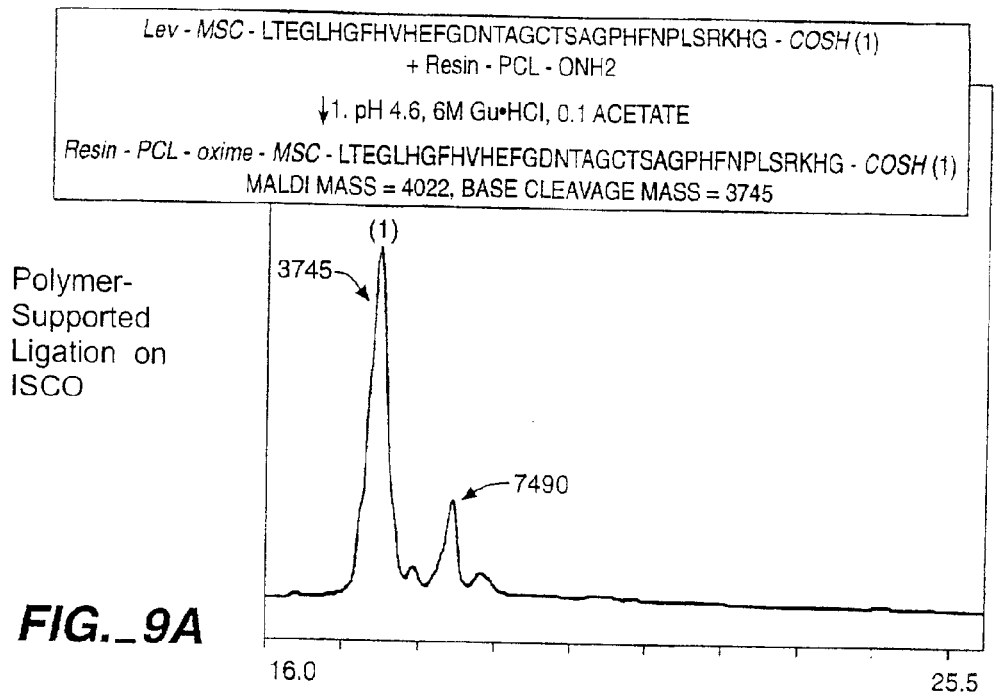
FIG._9A
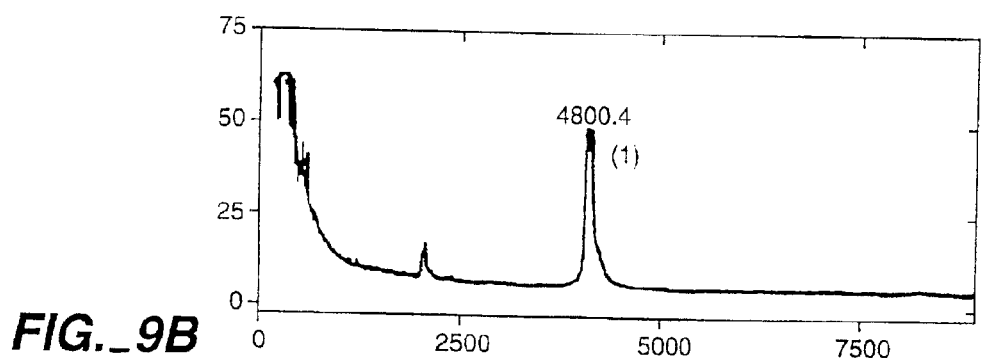
FIG._9B
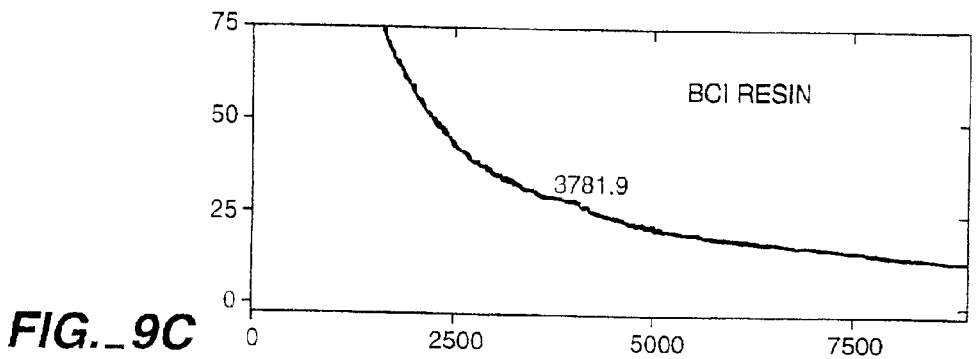
FIG._9C

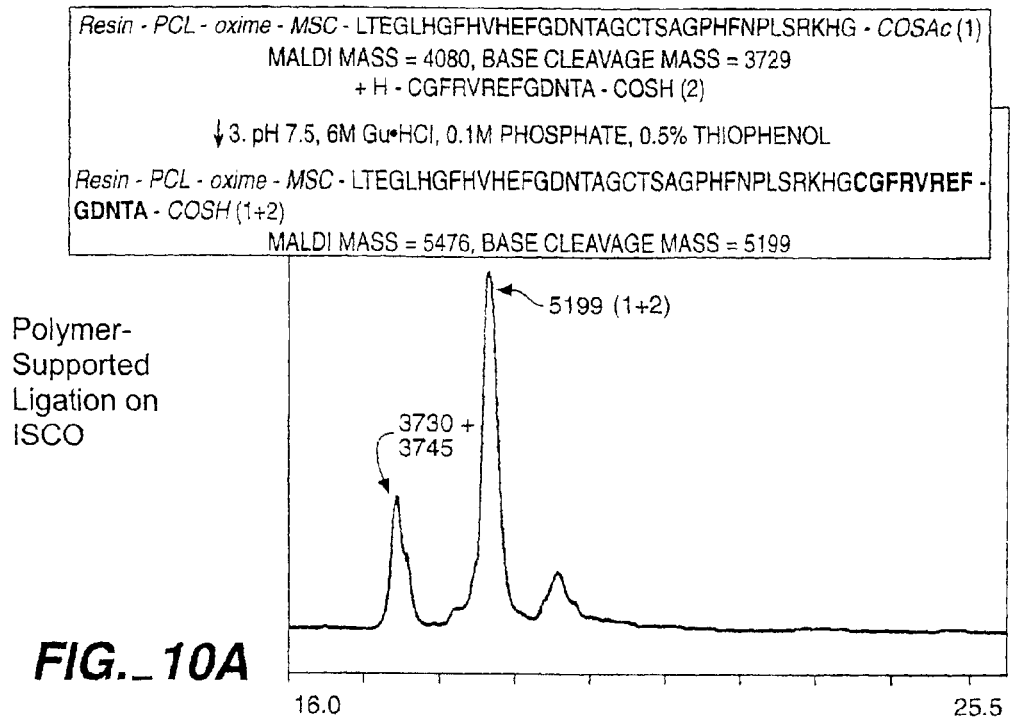
FIG._10A
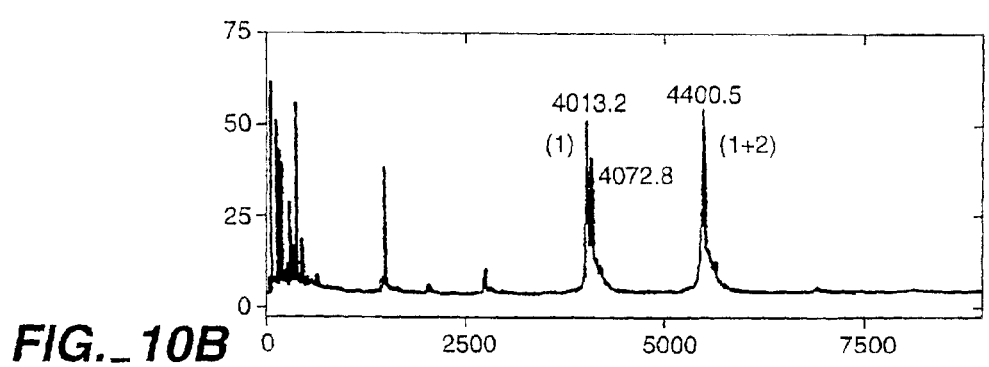
FIG._10B
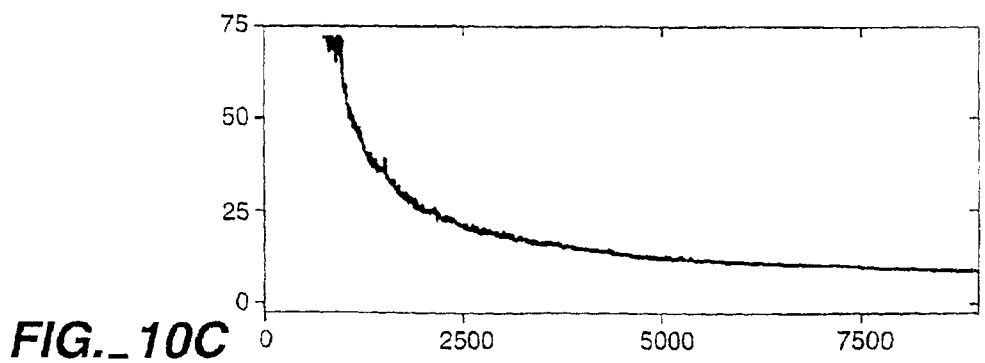
FIG._10C

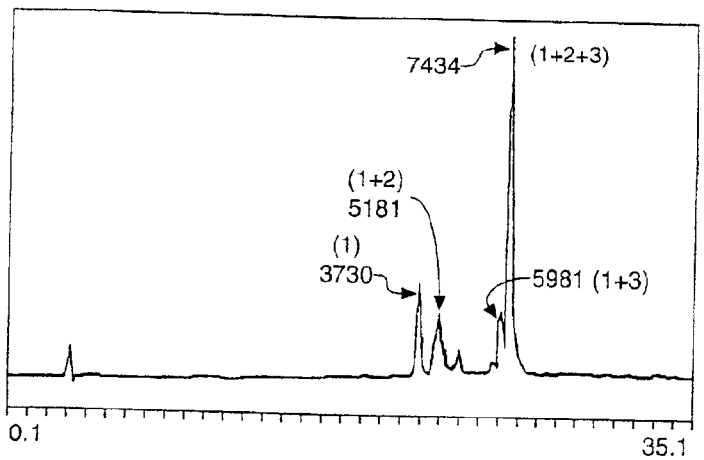
FIG._11
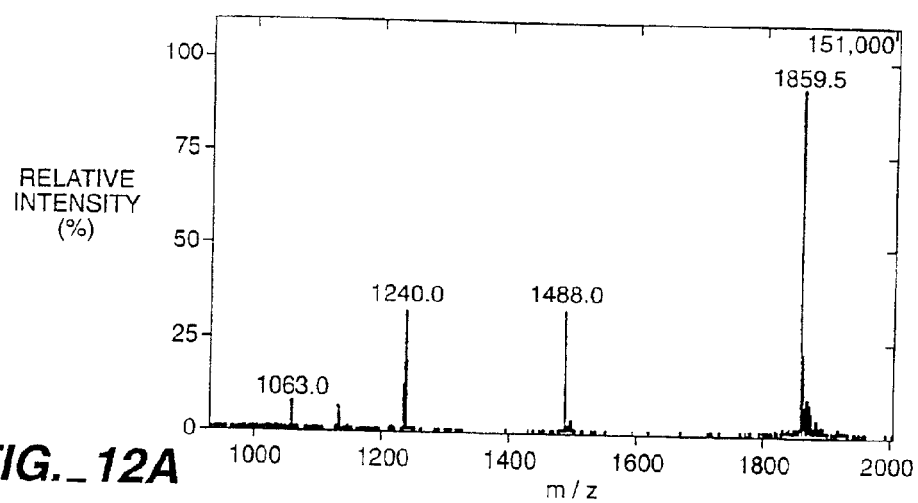
FIG._12A
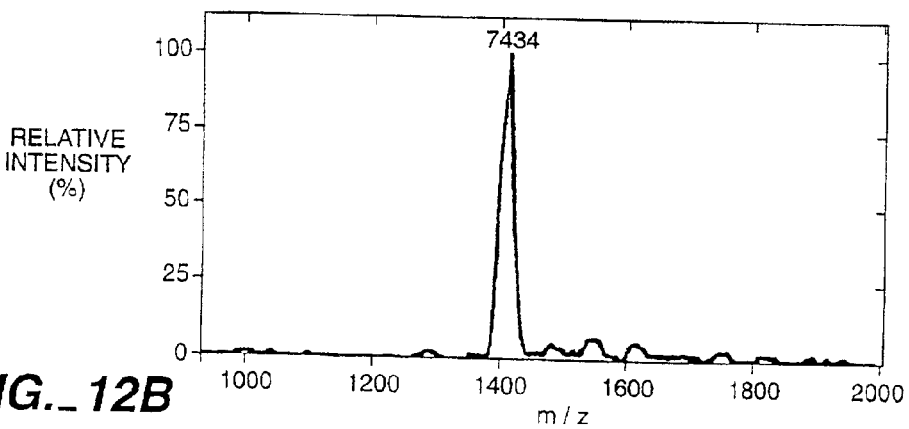
FIG._12B

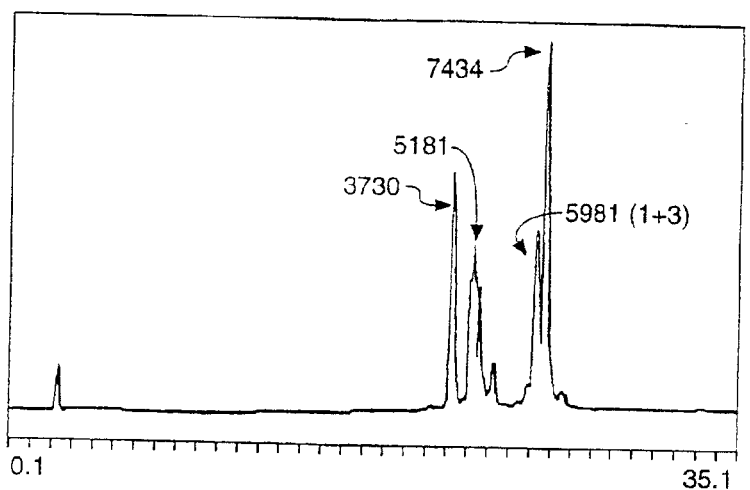
FIG._13
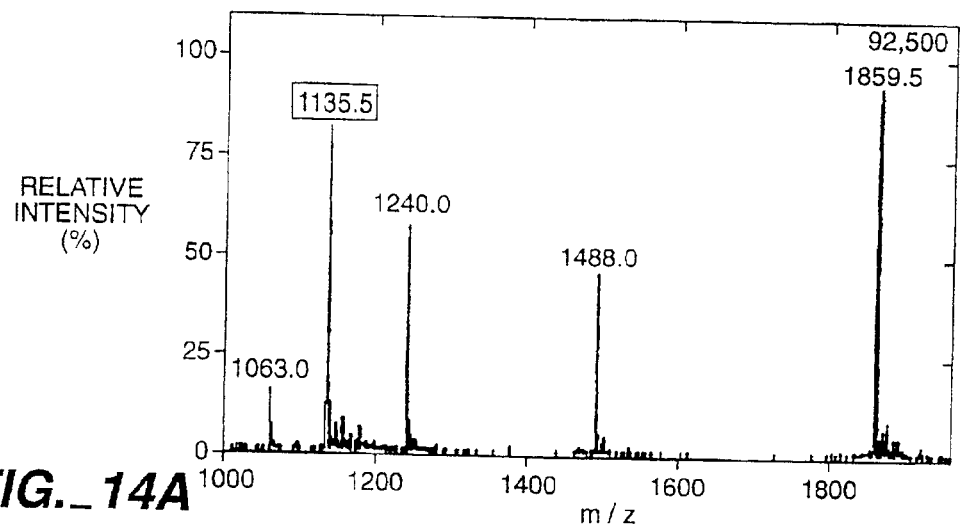
FIG._14A
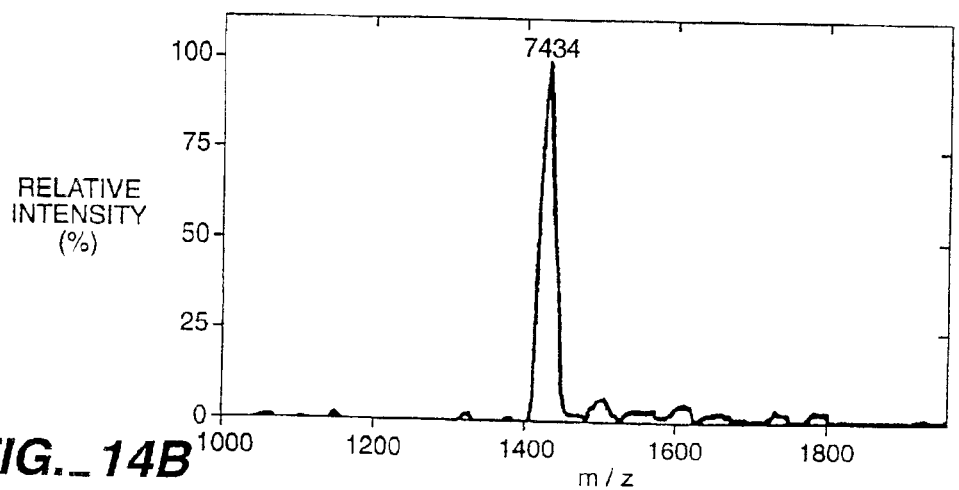
FIG._14B

On Resin Purification
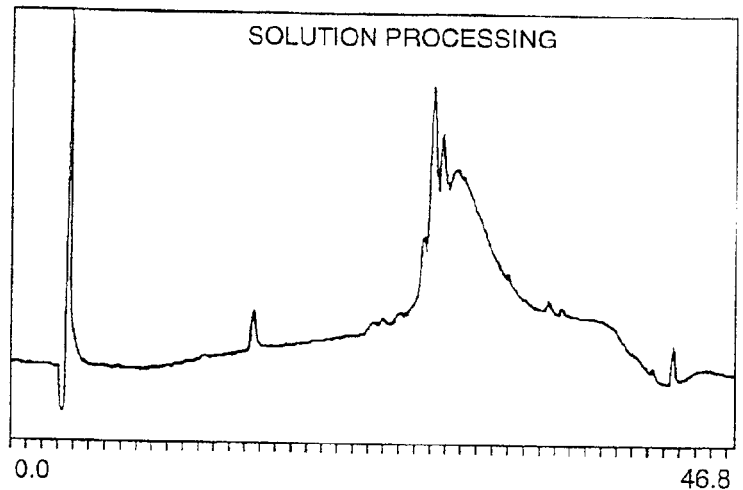
FIG._15A
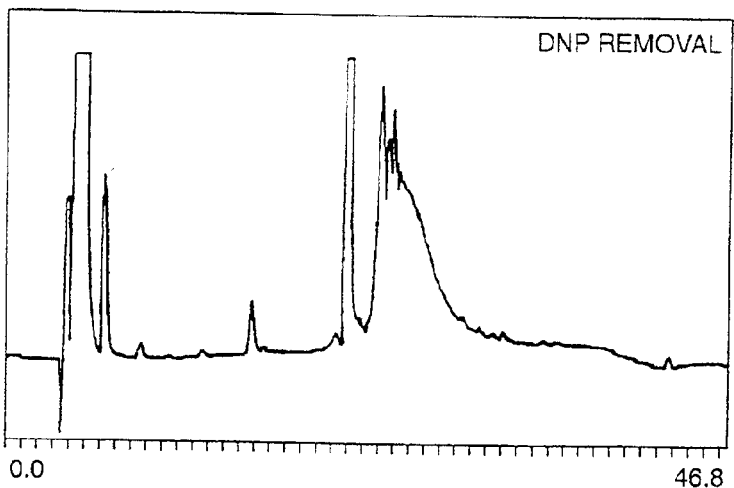
FIG._15B
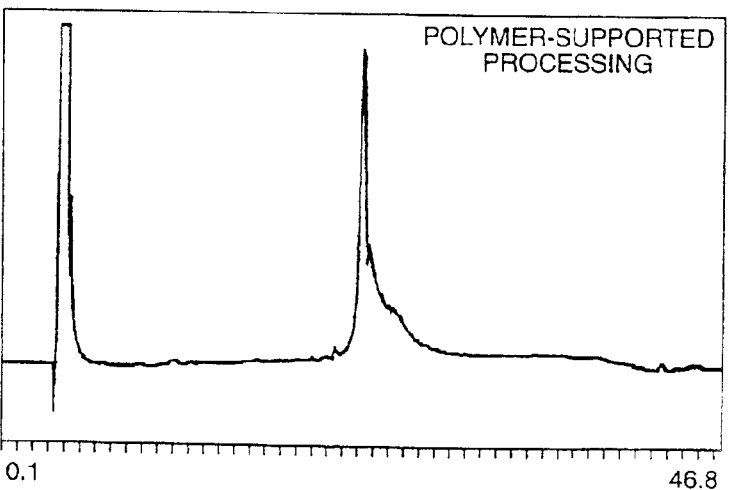
FIG._15C

Synthesis of MIF by Solid Phase Native Ligations

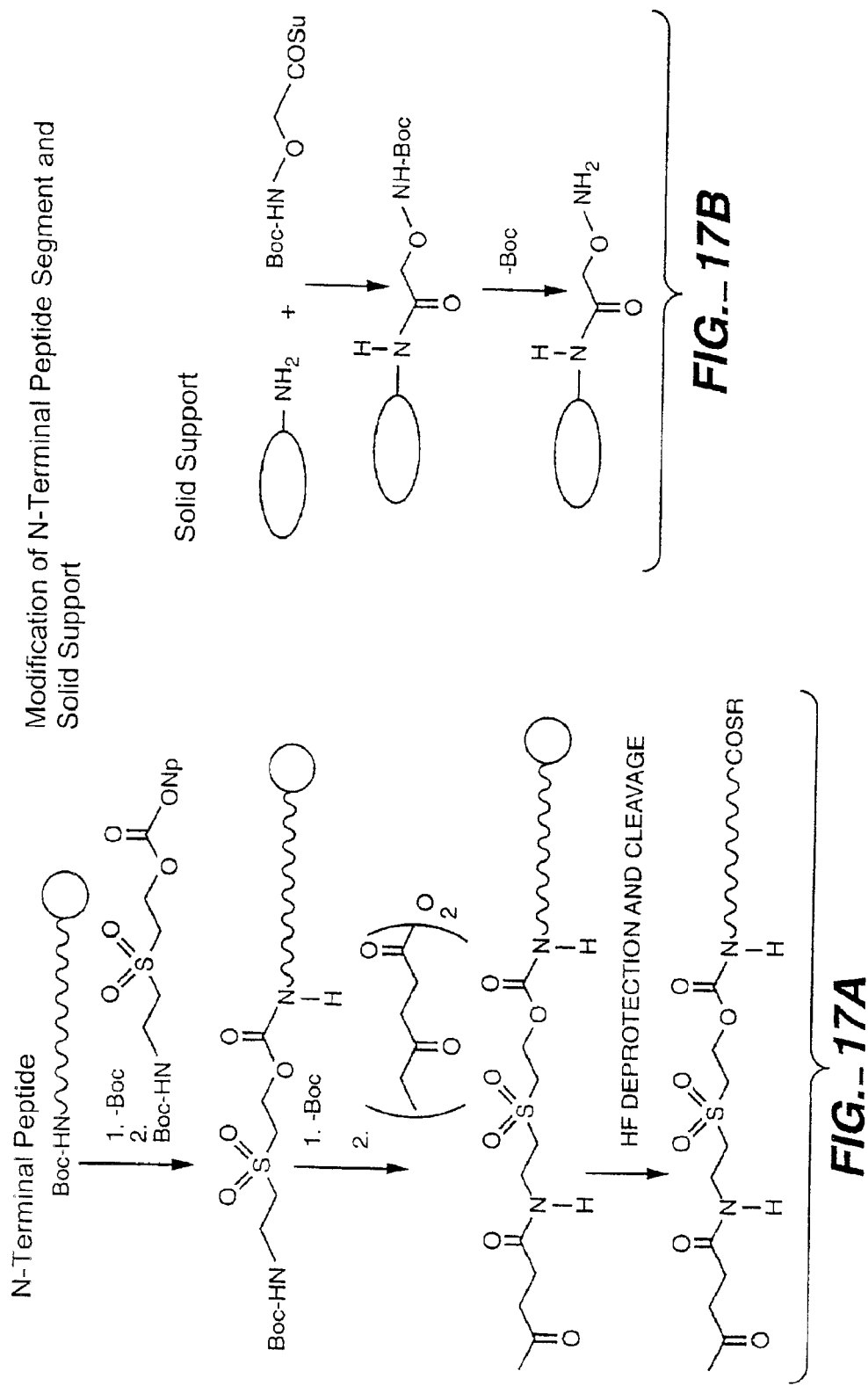
FIG.—17B
FIG.—17A

Coupling of MIF 1-59 to Solid Support
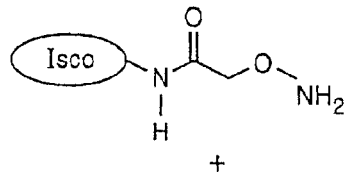
+
KETONE - MSC HANDLE - MET[1] - MIF 2 - 58 - Leu[59] - SAc - βAla - CO$_2$H
1 ↓
Isco — OXIME - MSC HANDLE - MET[1] - MIF 2 - 58 - Leu[59] - SAc - βAla - CO$_2$H
EXPECTED BASE CLEAVAGE MASS = 6271
FIG._18A
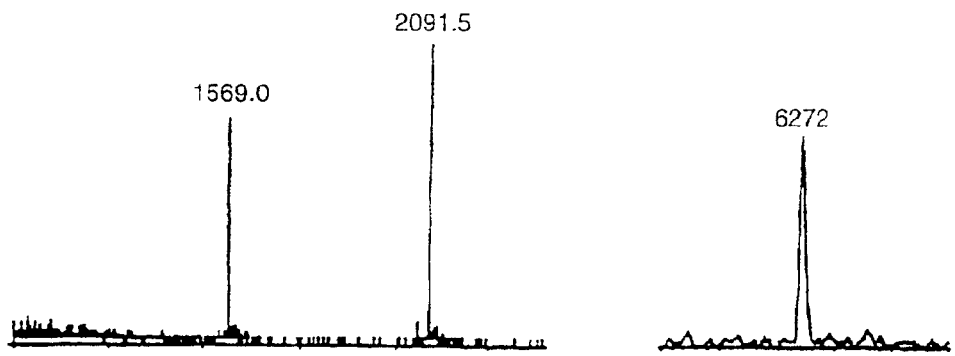
FIG._18C   FIG._18D
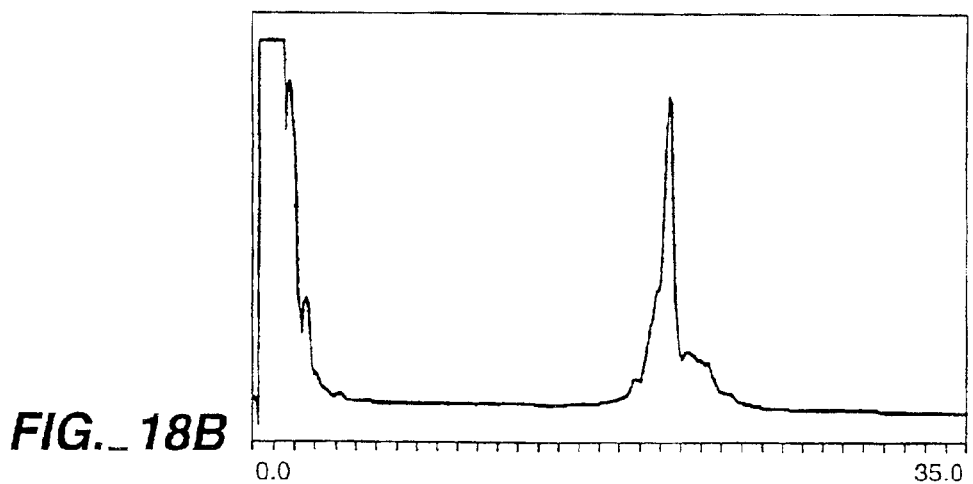
FIG._18B

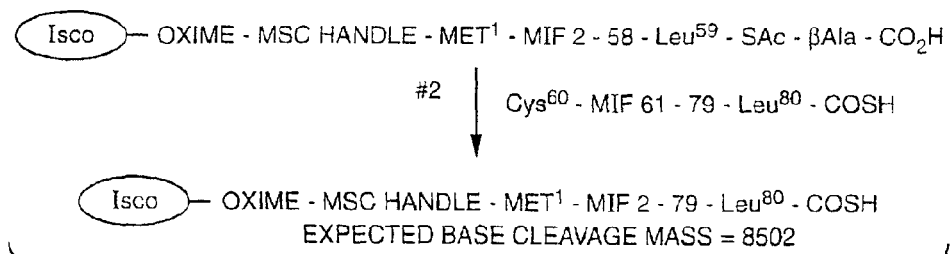
FIG._19A
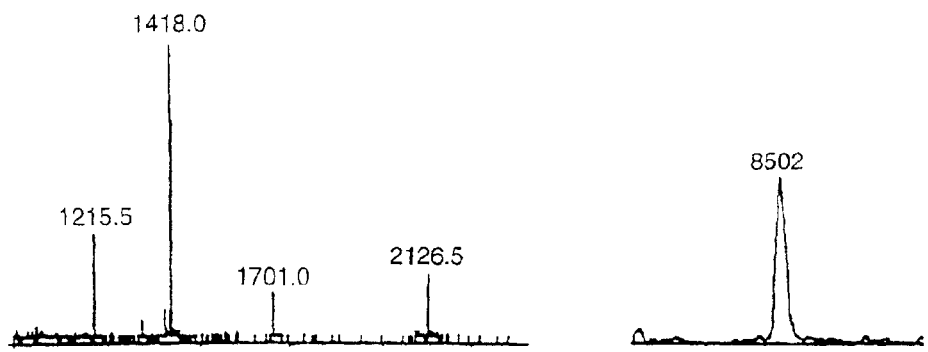
FIG._19C  FIG._19D
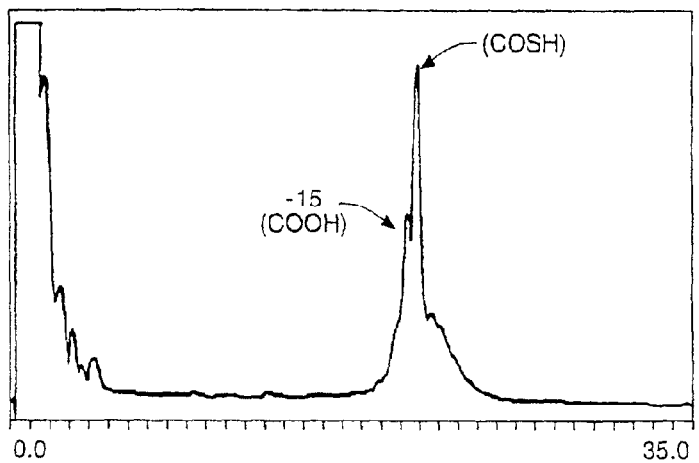
FIG._19B

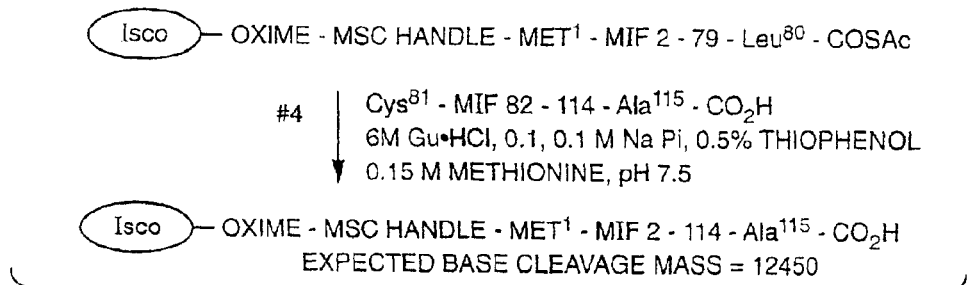
FIG._20A
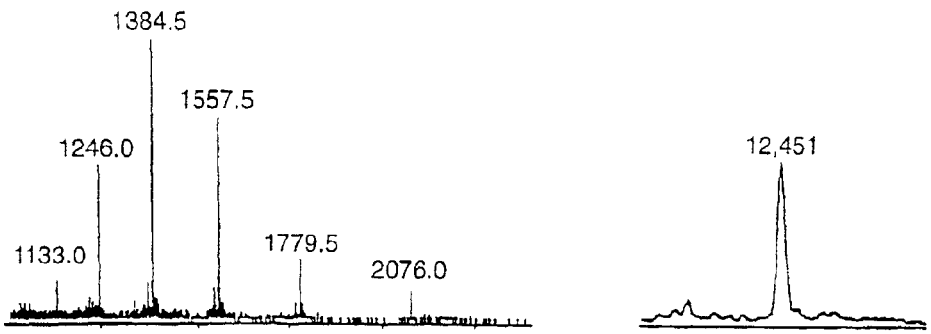
FIG._20C  FIG._20D
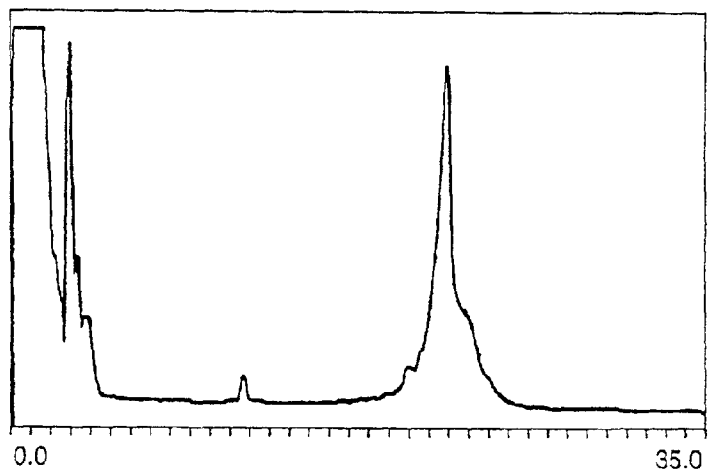
FIG._20B

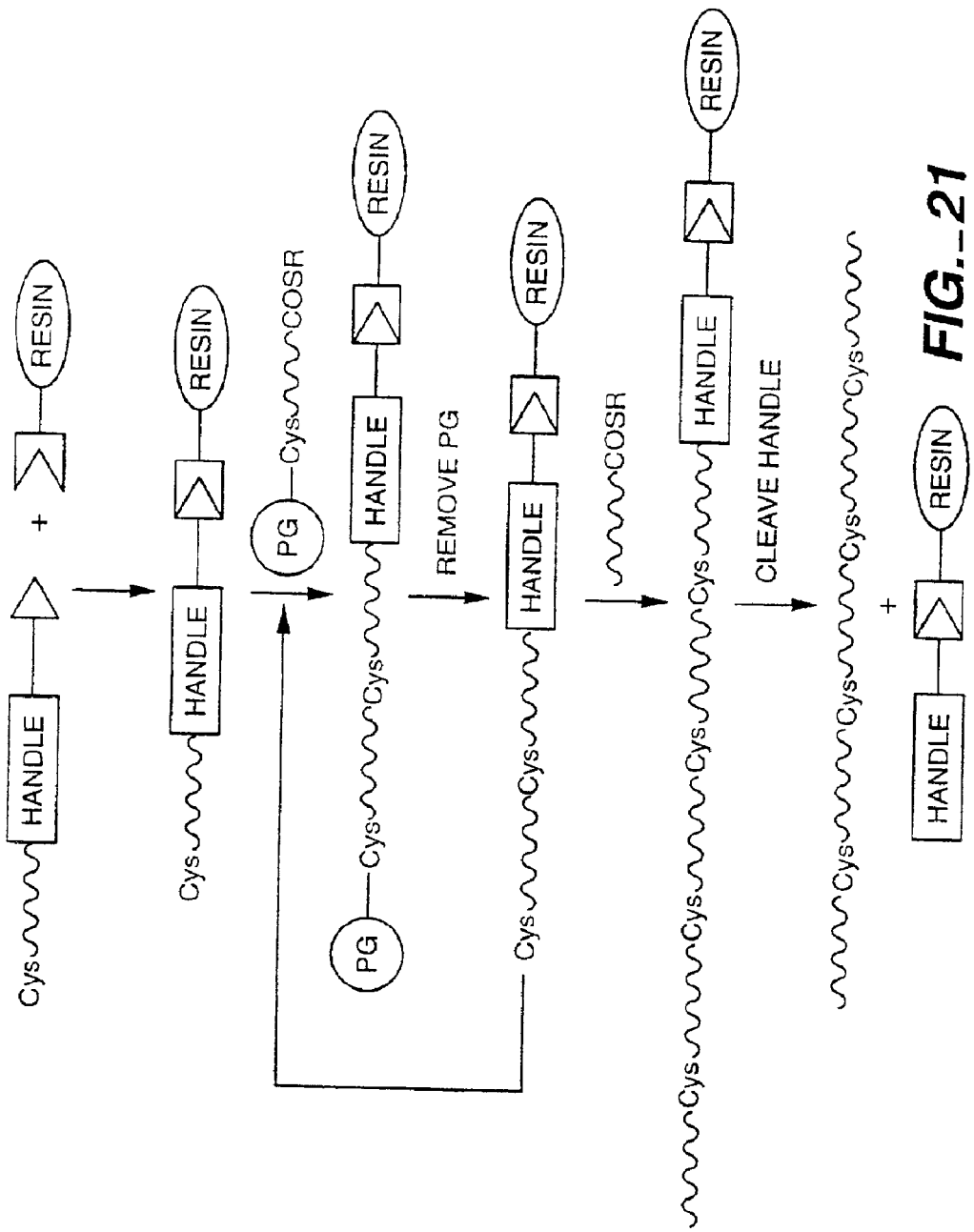
FIG._21

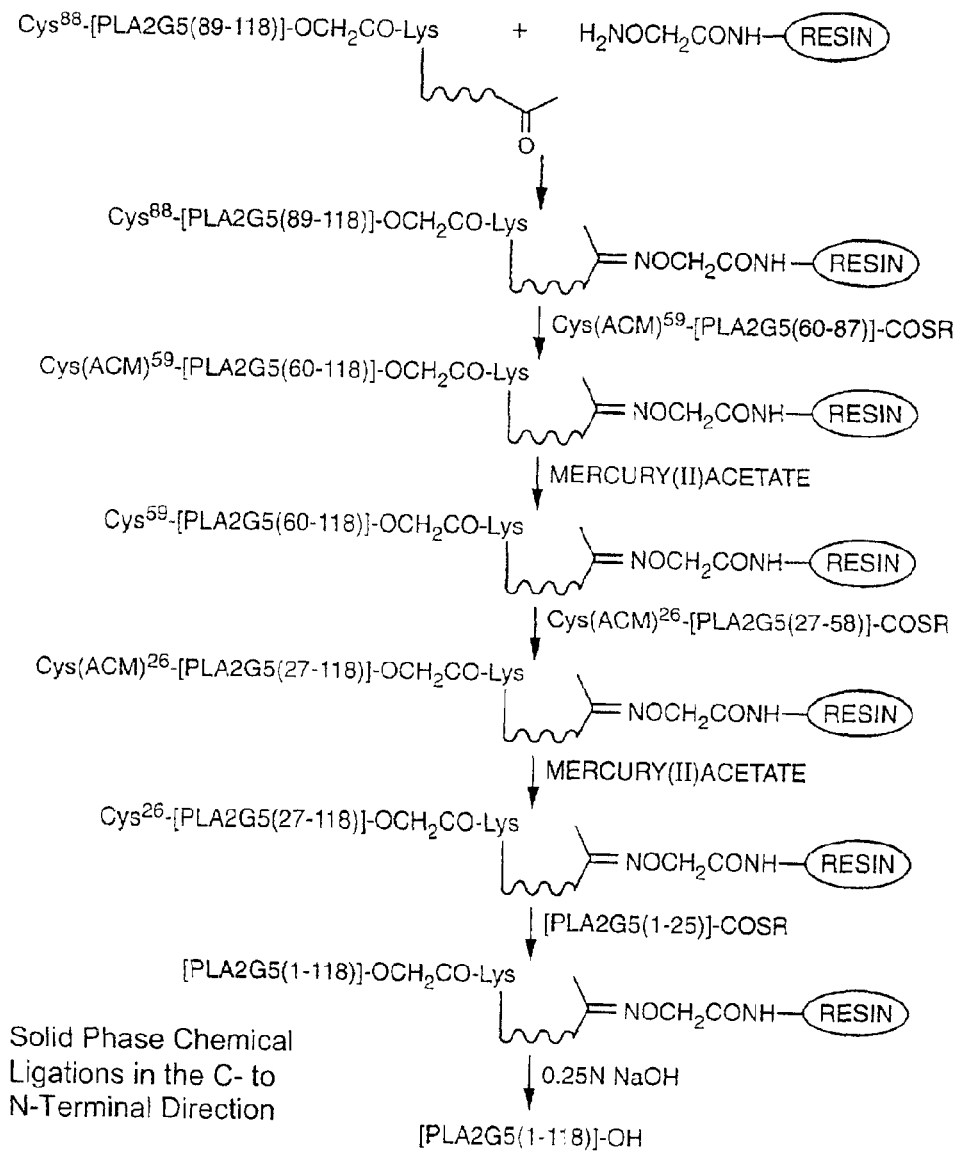
Solid Phase Chemical Ligations in the C- to N-Terminal Direction
Synthesis of Phospholipase A2, Group 5 (PLA2G5)
FIG._22

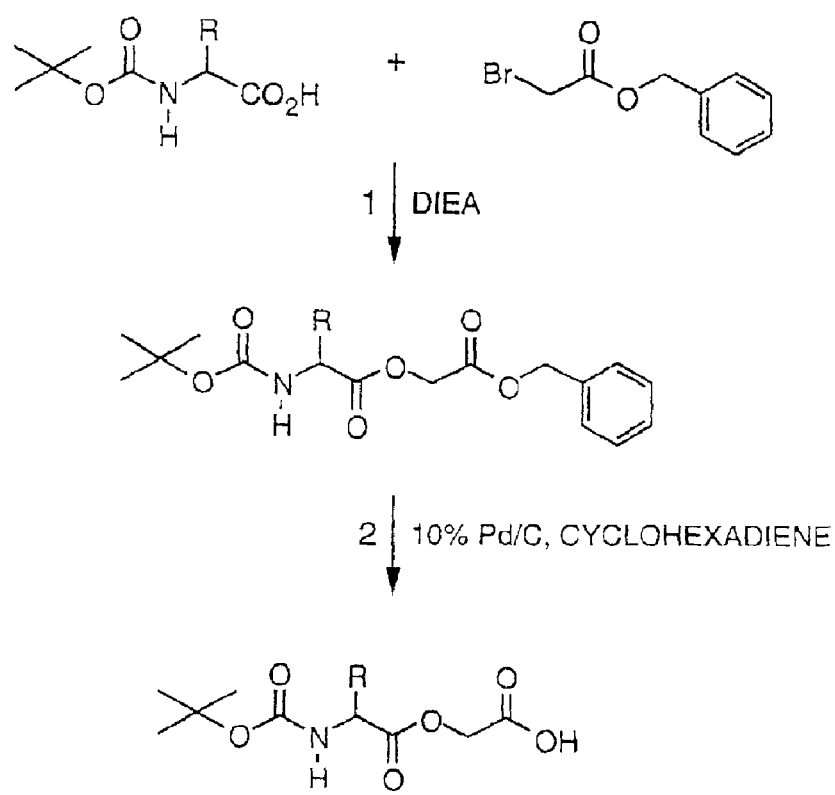
FIG._23
Synthesis of Cam ester derivative

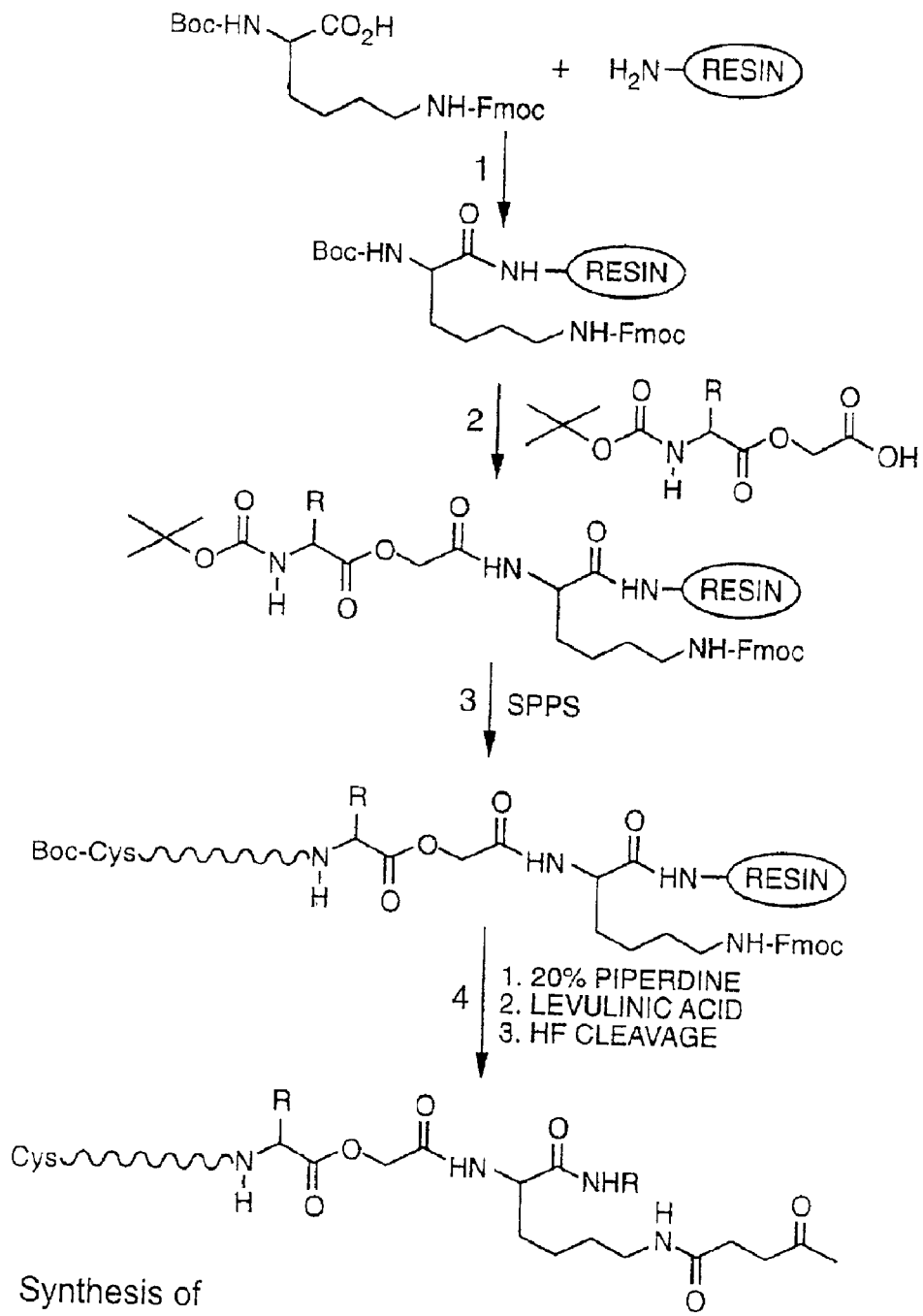
Synthesis of C-Terminal Peptide Segment
FIG._24

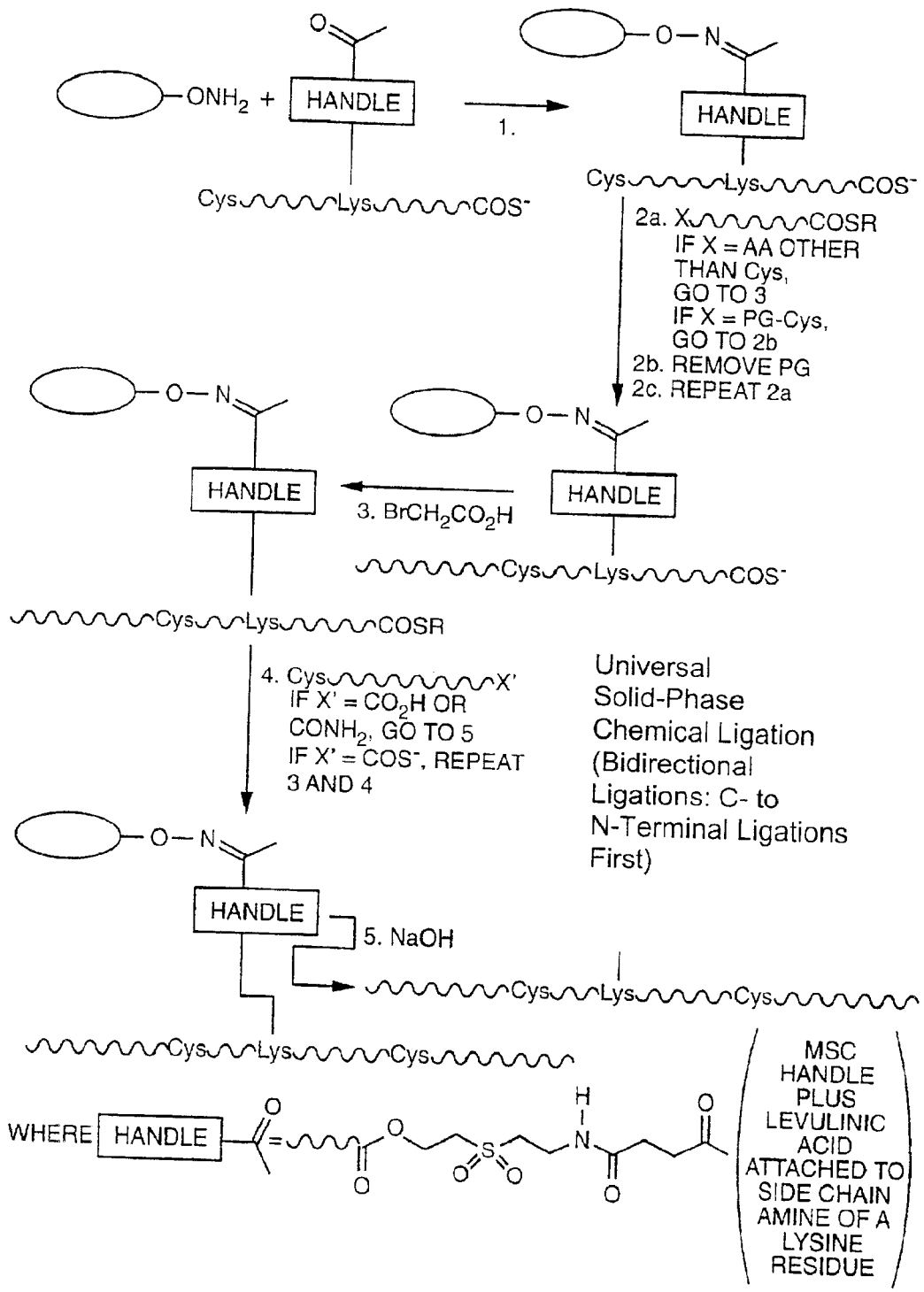
FIG._25A

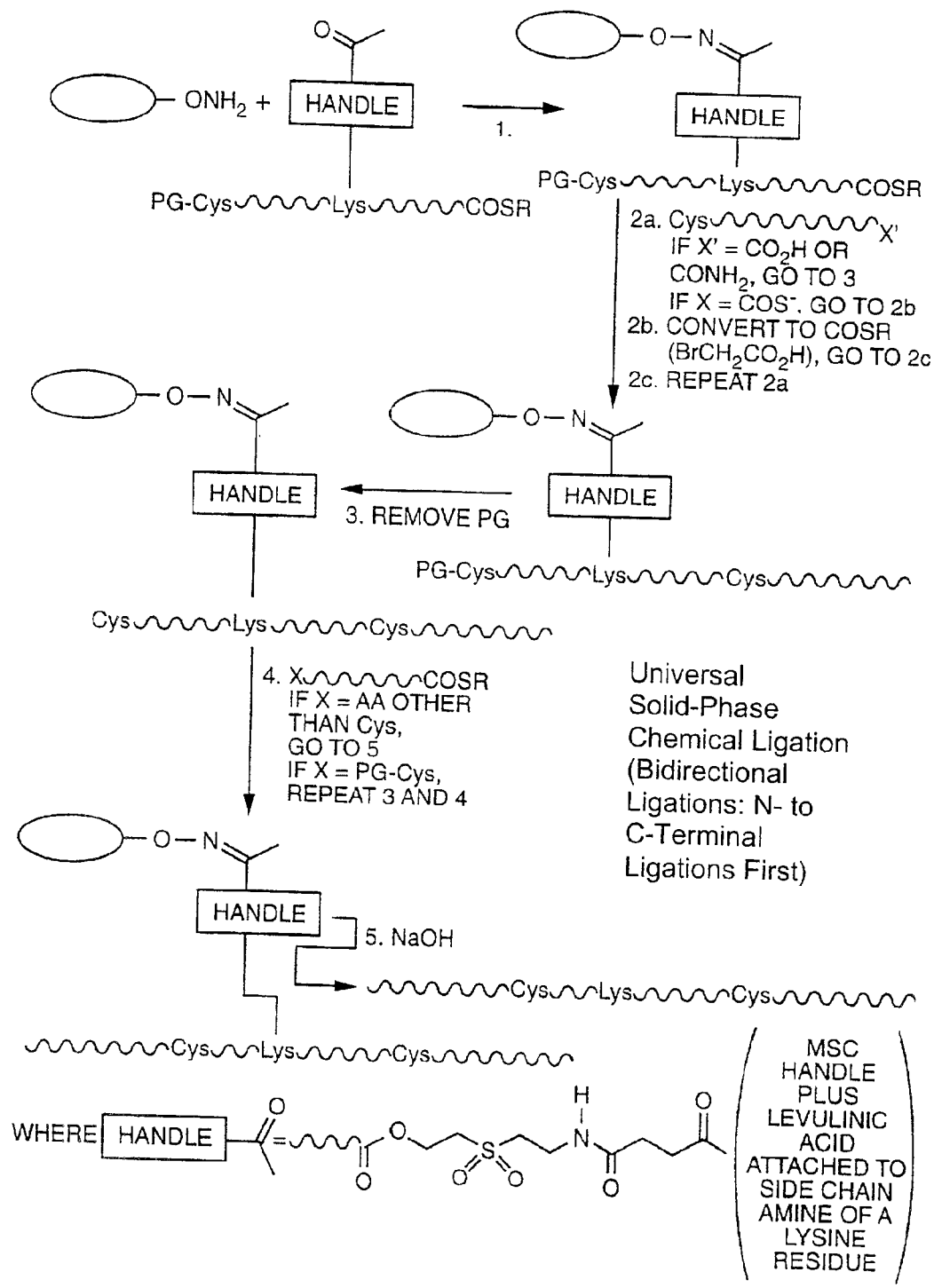
FIG._25B

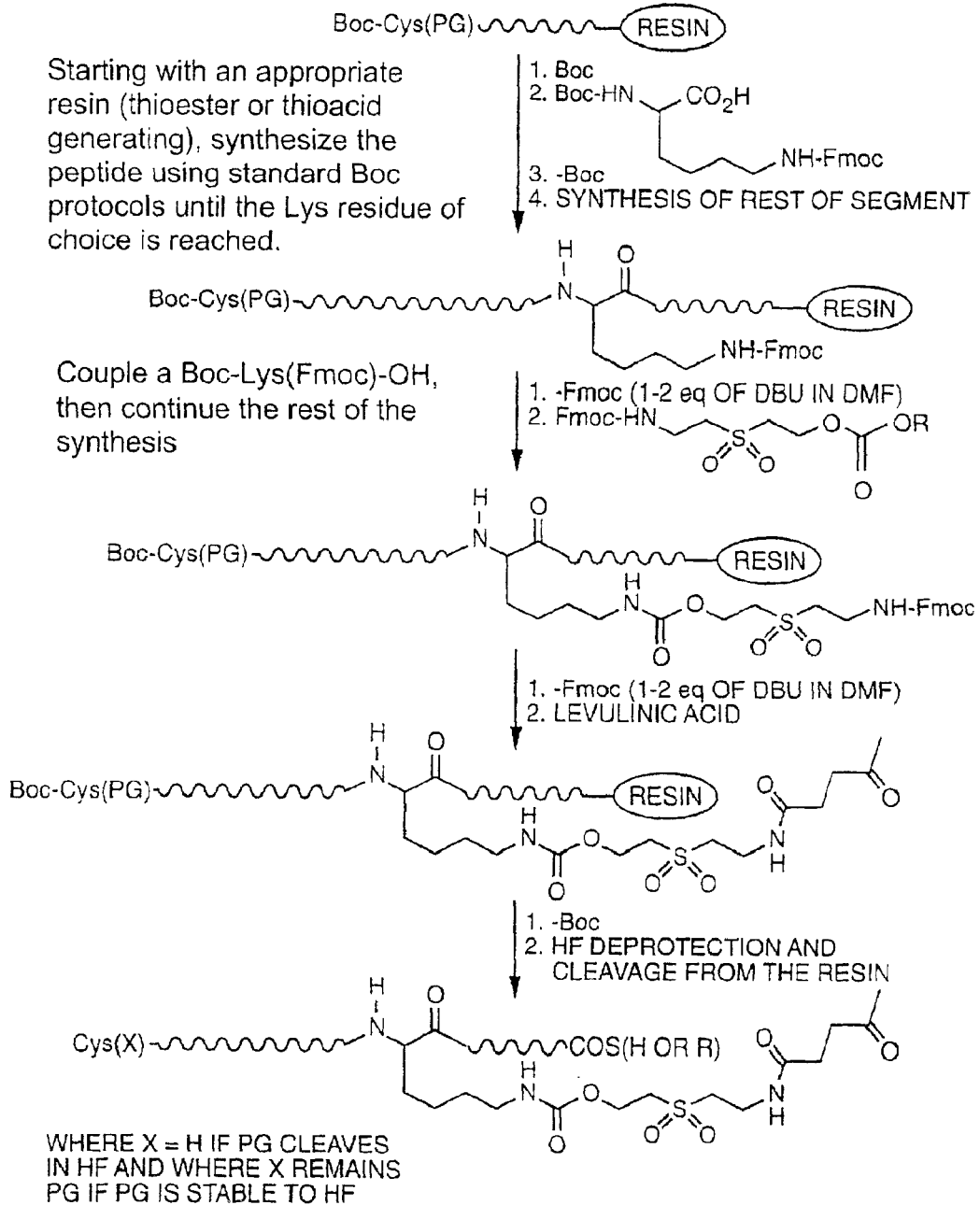
FIG._25C

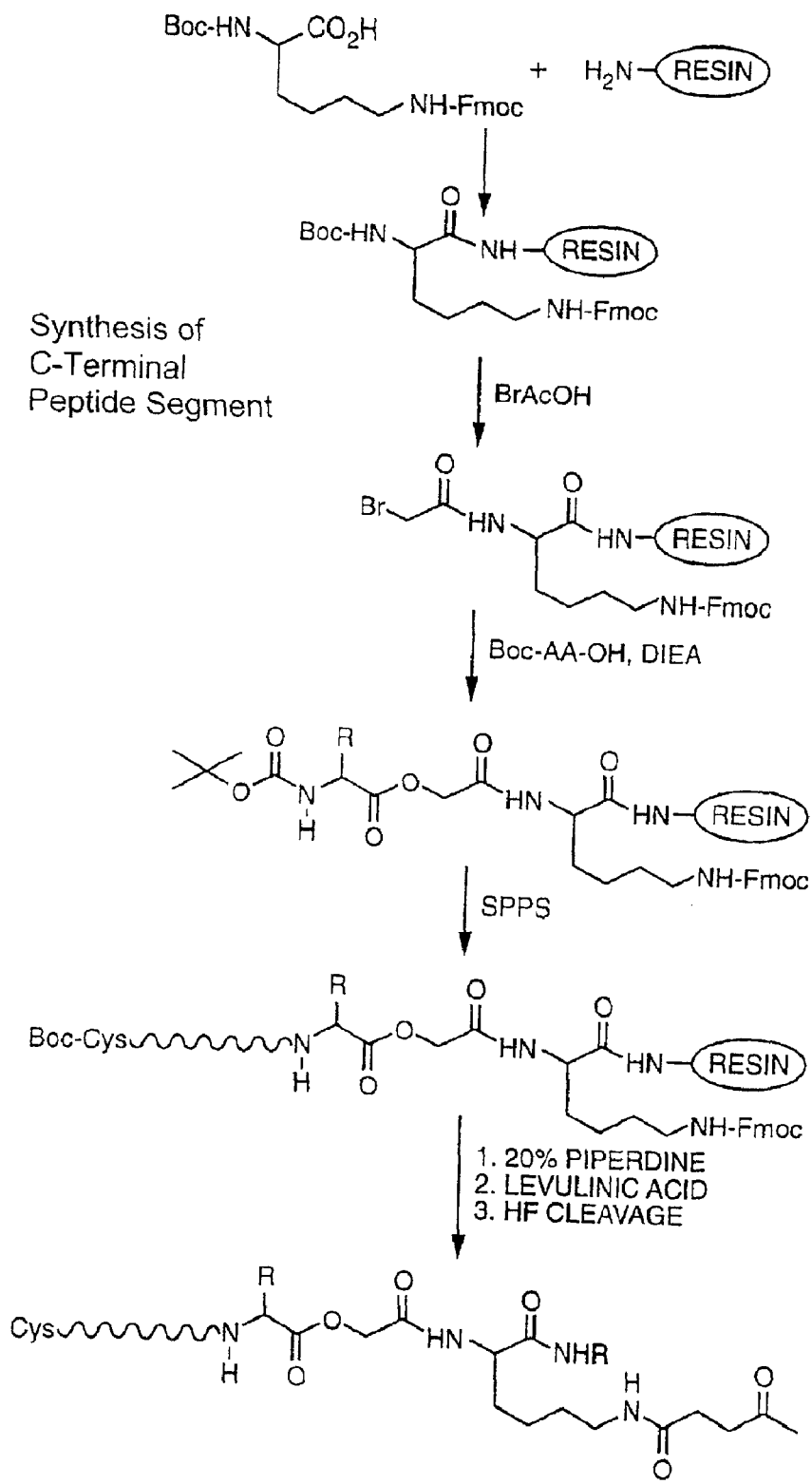
FIG._27

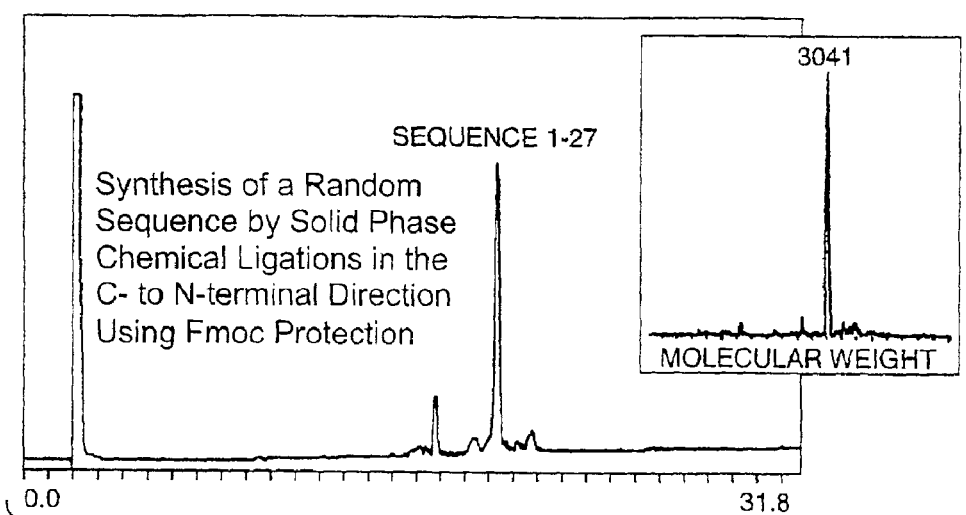
FIG._28
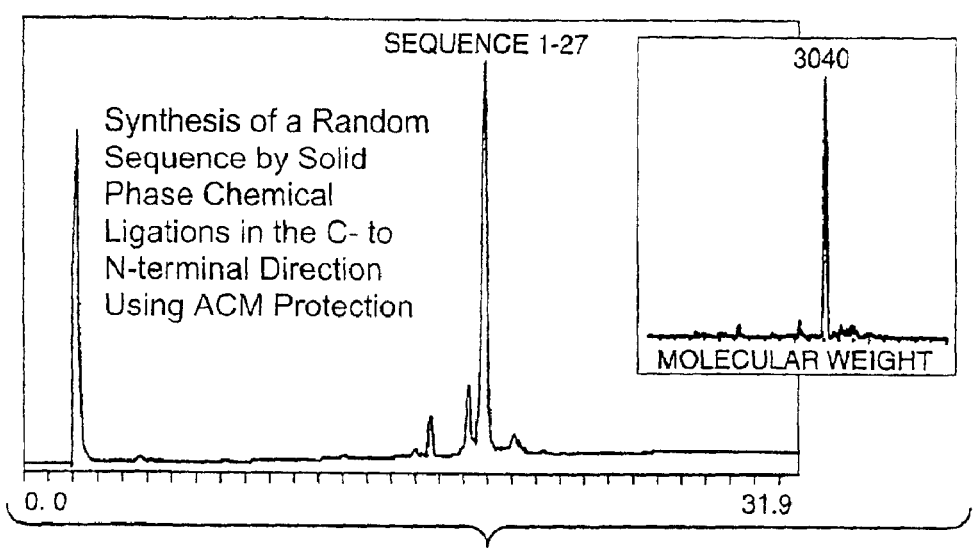
FIG._29

```
1                          26                                    59
GLLDLKSMIEKVTGKNALTNYGFYGCYCGWGGRGTPKDGTDWCCWAHDHCYGRLEEKGC
NIRTQSYKYRFAWGV VTCEPGPFCHVNLCACDRKLVYCLKRNLRSYNPQYQYFPNILCS
                           88                                  118
```
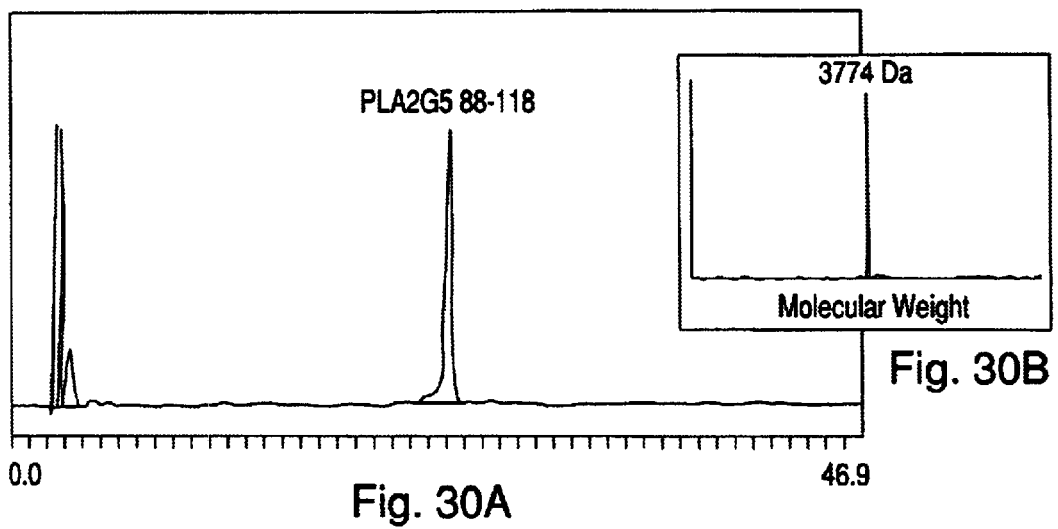
Fig. 30A / Fig. 30B
```
1                          26                                    59
GLLDLKSMIEKVTGKNALTNYGFYGCYCGWGGRGTPKDGTDWCCWAHDHCYGRLEEKGC
NIRTQSYKYRFAWGV VTCEPGPFCHVNLCACDRKLVYCLKRNLRSYNPQYQYFPNILCS
                           88                                  118
```
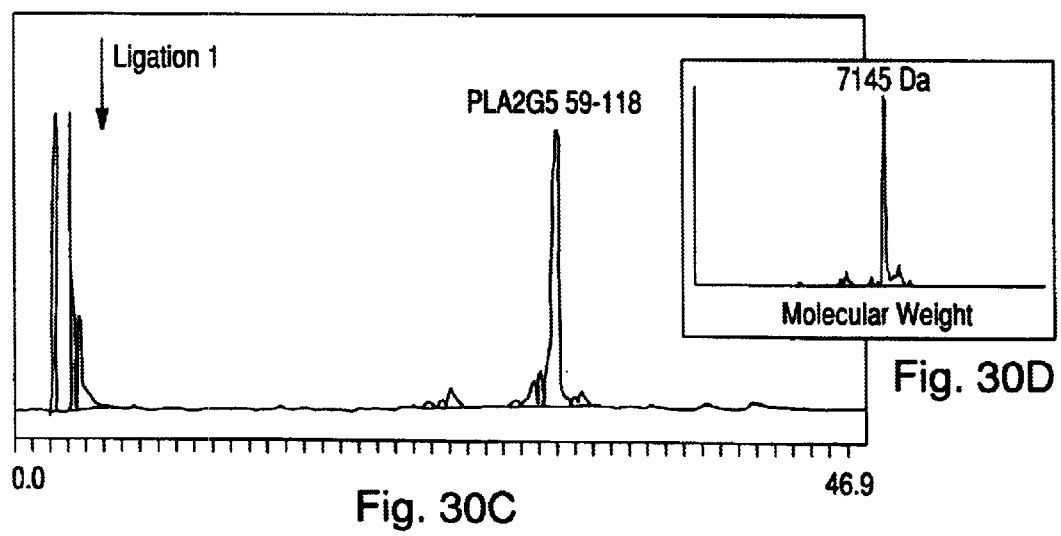
Fig. 30C / Fig. 30D

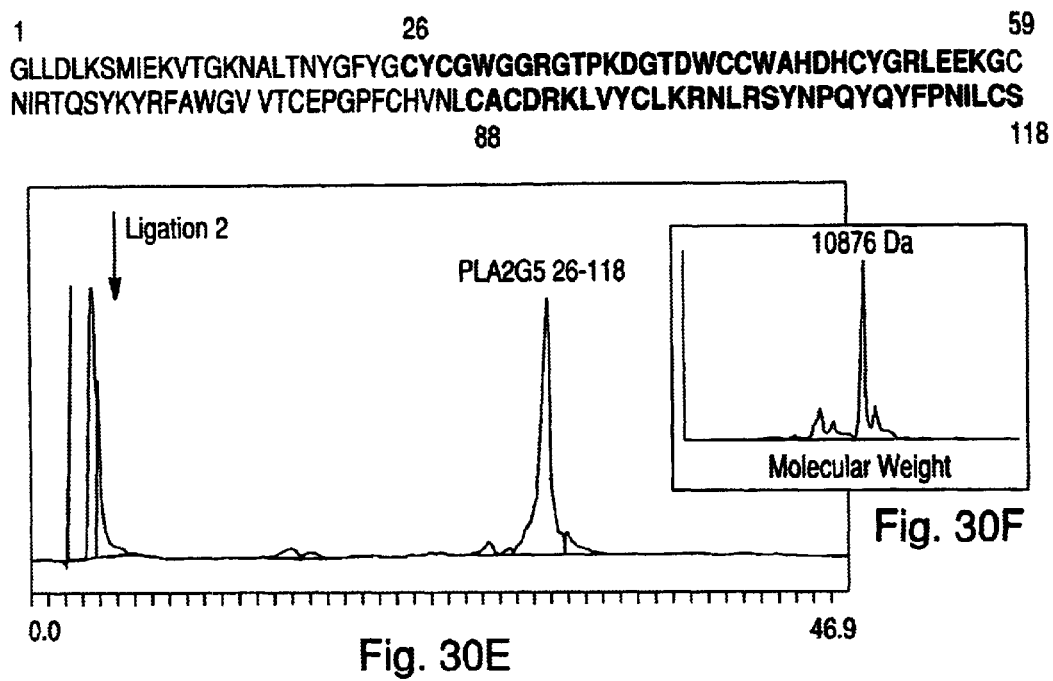
Fig. 30E / Fig. 30F
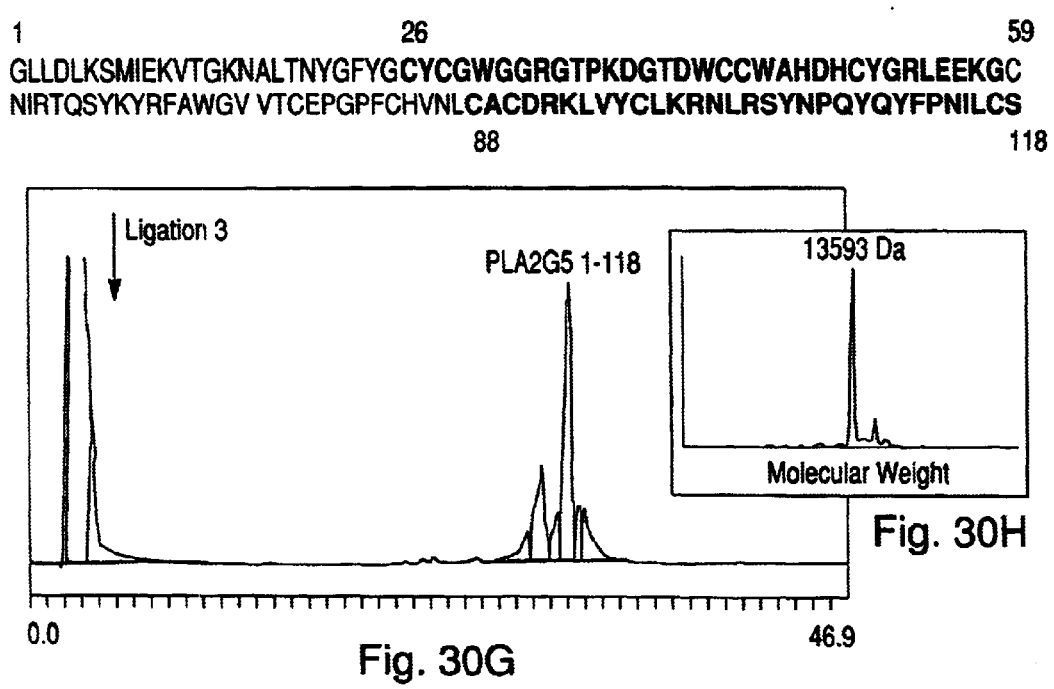
Fig. 30G / Fig. 30H

SOLID PHASE NATIVE CHEMICAL LIGATION OF UNPROTECTED OR N-TERMINAL CYSTEINE PROTECTED PEPTIDES IN AQUEOUS SOLUTION

CROSS-REFERENCE TO RELATED APPLICATIONS

This application is a continuation-in part of, and claims the benefit of, U.S. Provisional Application No. 60/049,553, filed Jun. 13, 1997, herein incorporated by reference, and is a divisional application of, and claims the benefit of, U.S. patent application Ser. No. 09/097,094, filed Jun. 12, 1998, now U.S. Pat. No. 6,326,468, herein incorporated by reference.

BACKGROUND

Existing methods for, the chemical synthesis of proteins include stepwise solid phase synthesis, and fragment condensation either in solution or on solid phase. The classic stepwise solid phase synthesis of Merrifield involves covalently linking an amino acid corresponding to the carboxy-terminal amino acid of the desired peptide chain to a solid support and extending the polypeptide chain toward the amino end by stepwise coupling of activated amino acid derivatives having activated carboxyl groups. After completion of the assembly of the fully protected solid phase bound peptide chain, the peptide-solid phase covalent attachment is cleaved by suitable chemistry and the protecting groups removed to give the product polypeptide.

Some disadvantages of the stepwise solid phase synthesis method include: incomplete reaction at the coupling and deprotection steps in each cycle results in formation of solid-phase bound by products. Similarly, side reactions due to imperfections in the chemistry, and or impurities present in the reagents/protected amino acids, all lead to a multiplicity of solid phase bound products at each step of the chain assembly and to the formation of complex product mixtures in the final product. Thus, the longer the peptide chain, the more challenging it is to obtain high-purity well-defined products. Due to the production of complex mixtures, the stepwise solid phase synthesis approach has size limitations. In general, well-defined polypeptides of 100 amino acid residues or more are not routinely prepared via stepwise solid phase synthesis. Synthesis of proteins and large polypeptides by this route is a time-consuming and laborious task.

The solid phase fragment condensation approach (also known as segment condensation) was designed to overcome the difficulties in obtaining long polypeptides via the solid phase stepwise synthesis method. The segment condensation method involves preparation of several peptide segments by the solid phase stepwise method, followed by cleavage from the solid phase and purification of these maximally protected segments. The protected segments are condensed one-by-one to the first segment, which is bound to the solid phase.

Often, technical difficulties are encountered in many of the steps of solid phase segment condensation. See E. Atherton, et al., "Solid Phase Fragment Condensation—The Problems," in Innovation and Perspectives in Solid Phase Synthesis 11–25 (R. Epton, et al. 1990). For example, the use of protecting groups on segments to block undesired ligating reactions can frequently render the protected segments sparingly soluble, interfering in efficient activation of the carboxyl group. Limited solubility of protected segments also can interfere with purification of protected segments. See K. Akaji et al., Chem. Pharm. Bull.(Tokyo) 33:184–102 (1985). Protected segments are difficult to characterize with respect to purity, covalent structure, and are not amenable to high resolution analytical ESMS (electrospray mass spectrometry) (based on charge). Racemization of the C-terminal residue of each activated peptide segment is also a problem, except if ligating is performed at Glycine residues. Moreover, cleavage of the fully assembled, solid-phase bound polypeptide from the solid phase and removal of the protecting groups frequently can require harsh chemical procedures and long reaction times that result in degradation of the fully assembled polypeptide.

Segment condensation can be done in solution rather than on solid phase. See H. Muramatsu et al., Biochem. and Biophys. Res. Commn. 203(2):1131–1139 (1994). However, segment condensation in solution requires purification of segments prior to ligation as well as use of protecting groups on a range of different side chain functional groups to prevent multiple undesired side reactions. Moreover, the ligation in solution does not permit easy purification and wash steps afforded by solid phase ligations. Furthermore, the limitations with respect to solubility of protected peptide segments and protected peptide intermediate reaction products are exacerbated.

Chemical ligating of minimally protected peptide segments has been explored in order to overcome the solubility problems frequently encountered with maximally protected peptide segments. See Cheng, et al., Chemical Synthesis of Human θ-endorphin(1–27) Analogs by Peptide Segment Coupling. Int. J. Pept. Protein Res. 38:70–78 (1991); J. Blake, Total Synthesis of S-Carbamoylmethyl Bovine Apocytochrome c by Segment Coupling, Int. J. Pept. Protein Res. 27:191–200 (1986); and H. Hojo et al., Protein Synthesis using S-Alkyl Thioester of Partially Protected Peptide Segments, Synthesis of DNA-Binding Protein of *Bacillus stearothermophilus*, Bull. Chem. Soc. Jpn. 65:3055–3063 (1992). However, this method still requires the use of protecting groups on all Lysine side chain amino groups, selective N-α protection of one or more segments, and laborious purification steps, involving purification, reprotection, and repurification.

The use of multiply protected peptide segments is incompatible with the overall scheme of engineering proteins using peptides produced by means of recombinant DNA expression as a source. Protected peptide segment methods are labor-intensive, and the protected peptide segments have unpredictable handling properties, partly due to the solubility and ligating difficulties of protected peptide segments. Often, large protected peptide segments are minimally soluble in even the most powerful polar aprotic solvents such as dimethylsulfoxide (DMSO) and dimethylformamide (DMF). The problem of insolubility in protected peptide segments has been addressed with limited success in several ways, including the use of (1) partial protecting group strategy which masks all side chains except those of Ser, Thr, and Tyr; (2) minimal protecting group strategy that masks only thiol and amino side chains; and (3) using reversible protection of a backbone amide moiety to prevent aggregation/insolubility. Protecting groups used in the latter approach alter peptide conformations. Use of backbone protecting groups is not yet straightforward or predictable and requires significant experimentation for each target polypeptide chain.

There are a number of techniques for ligating unprotected peptide segments via unnatural backbone linkages. In contrast, there are few methods for achieving a "native chemical ligation." A "native chemical ligation" is the chemoselective reaction of unprotected or N-terminal Cysteine protected peptide segments with another unprotected peptide segment resulting in the formation of a ligated peptide with an amide bond at the ligation site. The fully assembled target polypeptides of the invention comprise one, two or more native chemical ligation sites.

Accordingly, there is a need in the art for rapid methods of synthesizing assembled polypeptides via chemical ligation of two or more unprotected peptide segments using a solid support, with improved yields and facilitated handling of intermediate products.

The present invention makes possible, inter alia, the rapid solid-phase synthesis of large polypeptides with a natural peptide backbone via native chemical ligation of two or more unprotected peptide segments where none of the reactive functionalities on the peptide segments need to be temporarily masked by a protecting group. The present invention accomplishes for the first time, solid phase sequential chemical ligation of peptide segments in an N-terminus to C-terminus direction, with the first solid phase-bound unprotected peptide segment bearing a C-terminal α-thioester that reacts with another unprotected peptide segment containing an N-terminal Cysteine and a C-terminal thioacid.

Other embodiments of the invention also permit solid-phase native chemical ligation in the C- to N-terminus direction, with temporary protection of N-terminal cysteine residues on an incoming (second) peptide segment. Those of ordinary skill in the art will readily appreciate that the invention may also include the use of nonnative chemical ligation to sequentially ligate peptide segments via unnatural linkages on a solid phase. Alternatively, the invention may include the use of native chemical ligation of peptide segments wherein said peptide segments comprise one or more unnatural backbone linkages.

REFERENCES

Matthys J. Janssen, "Thiolo, Thiono, and Dithio Acids and Esters," Chptr. 15 of The Chemistry of Carboxylic Acids and Their Esters (1969).

Schnolzer et al., Science 256:221–225 (1992)

Rose et al. J. Am Chem. Soc. 116:30–34 (1994)

Liu et al., Proc. Natl. Acad. Sci. USA 91:6584–6588 (1994).

Dawson et al. Science 266:77–779 (1994).

PCT/US95/05668, WO 96/34878

Sakakibara S., Biopolymers (Peptide Science), 37:17–28 (1995).

Tam et al., PNAS USA, 92:12485–12489 (1995).

SUMMARY OF THE INVENTION

The present invention provides, inter alia, novel methods of producing large polypeptides by native chemical ligation of peptide segments in aqueous solution to an unprotected solid phase bound peptide without need for protecting groups on the peptide segments, or, with temporary protection of the N-terminal cysteine of incoming peptide segments. Among the many advantages of this embodiment of the invention are: ease of purification of the intermediate and final products; faster ligation reactions; rapid synthesis of large polypeptides with a natural peptide backbone; ease of ligating reactions due to the lack of protecting groups and resultant enhanced solubility of peptide segments in aqueous or mixed aqueous/organic solutions; chemoselective ligation due to the lack of reactivity of the thioester moiety with other functional groups present in both reactive peptide segments to form stable co-products, resulting in a purer final product without side reactions; adaptability to monitoring on the solid phase via MALDI mass spectrometry or ESI MS (electrospray ionization mass spectrometry); decreased racemization due to the use of mild activation using a thioester and the avoidance of elevated pHs; the polypeptide product is obtained directly in unprotected form; and adaptability to automation and combinatorial techniques.

A significant advantage of the solid phase ligations over solution ligations is that the solid phase ligation methods do not require arduous HPLC (high pressure liquid chromatography) purification and lyophilization steps after each ligating reaction, whereas ligations in solution do. Thus, the solid phase ligations eliminate many time-consuming purification steps that decrease the recovery of final product. Instead, the solid, phase sequential ligation methods here described only require a single HPLC purification and lyophilization step after the final unprotected peptide segment has been ligated and the assembled peptide is cleaved from the solid phase. The elimination of these time-consuming purification steps allows for faster synthesis of the final product, i.e. the assembled peptide, than would the analogous route in solution. Ready purification of the desired solid phase-bound product from soluble coproducts presents a tremendous advance in terms of the yield of the ultimate assembled polypeptide.

Another advantage of solid phase ligations is that they permit higher concentrations of reactants which leads to faster reaction rates. For example, by using an excess at high concentration of the incoming peptide segment as compared to the solid phase-bound peptide, reactions can reach completion much faster. The excess peptide segment can readily be washed off the solid phase after the ligation reaction is complete. Increased yields of final product can be accomplished by increasing concentrations of peptide segments. For example, the solid phase-bound polypeptide can be dried out on the solid-phase and ressolvated in ligation solution. Alternatively, the solid phase-bound peptide can be washed with a solution of incoming peptide segments at high concentration.

Other advantages of the present invention are that it allows for synthesis of much larger peptides and proteins than are presently attainable by conventional methods, it is amenable to automation, and the use of high resin loadings allow for easy scale up. Moreover, ligation in the N- to C-terminal direction permits the use of crude peptide segments without need for purification or lyophilization, since termination products formed during stepwise solid phase synthesis of the peptide segments will be unreactive with the solid phase-bound peptide.

In one embodiment, the invention comprises a method of producing an assembled peptide having a native peptide backbone by ligating peptide segments in the N- to C-terminal direction, comprising: a) covalently binding an unprotected first peptide segment to a solid phase via a linker comprising a cleavable moiety, wherein said cleavable moiety is stable under ligation conditions and said unprotected first peptide segment is bound to said cleavable moiety at its N-terminus and has an α-thioester at its C-terminus; b) optionally introducing a second unprotected peptide segment, wherein said second segment comprises a cysteine residue at its N-terminus and a thioacid at its C-terminus, under conditions suitable to permit ligation between said first unprotected peptide segment and said second unprotected peptide segment to form a natively ligated peptide bound to said solid phase, wherein said solid phase-bound peptide comprises a thioacid at its C-terminus, and subsequently converting said solid phase-bound peptide thioacid to a thioester; (c) optionally repeating step (b) with additional unprotected peptide segments; (d) introducing a final unprotected peptide segment, comprising a cysteine residue at its N-terminus, under conditions suitable to permit ligation between said solid phase-bound peptide and said final unprotected peptide segment. In a preferred embodiment, the cleavable moiety is cleaved to release the solid phase-bound peptide in the form of the assembled peptide. In another preferred embodiment, cleavable moiety is a cleavable linker capable of being cleaved for purposes of monitoring the sequential ligation reactions. In another embodiment, the first unprotected peptide segment is added as a peptide-αCOSH thioacid and subsequently converted to a thioester.

The sequential ligation in the N- to C-terminus direction is a surprisingly effective and elegant means of obtaining chemoselective ligation of unprotected peptide segments without racemization. Before the present invention, sequential ligations were not conducted in the N- to C-terminal direction due to concerns regarding racemization at the αCOX at the C-terminus of the peptide (peptide-αCOX). Using the present invention, the αCOSH at the C-terminus of the peptide segment is mildly activated to a thioester and the ligating reaction is carried out in the absence of base, in an aqueous buffered solution, resulting in mild conditions that do not generate racemic mixtures.

The methods of the invention can be used for native chemical ligation of peptide segments produced by stepwise solid phase synthesis. The last peptide segment to be added at the C-terminal end of the last solid phase-bound peptide in the reaction scheme may be a recombinantly expressed peptide having an N-terminal Cysteine residue (Cys-recombinant peptide). The thioacid moiety, which is activated to a thioester moiety, can be placed anywhere a native chemical ligation is desired, including on a side chain. Thus, the sequential ligations of the invention are not limited to linearly assembled peptides.

In another embodiment, there is the use of unprotected peptide segment middle pieces each having an N-terminal cysteine residue that participate in native chemical ligation.

In another embodiment, the invention comprises a method of producing an assembled peptide having a native peptide backbone by ligating peptide segments in the C- to N-terminal direction, comprising: a) covalently binding an unprotected first peptide segment to a solid phase via a cleavable handle comprising a cleavable moiety, wherein said cleavable moiety is stable under ligation conditions and said unprotected first peptide segment is bound to said cleavable moiety at its C-terminus and has a Cysteine at its N-terminus; b) introducing a second peptide segment, wherein said second segment comprises a cysteine residue at its N-terminus and an alpha-thioester at its C-terminus, and wherein said second peptide segment has a protecting group bound to its N-terminal cysteine residue, under conditions suitable to permit ligation between said first peptide segment and said second N-terminally protected peptide segment to form a natively ligated peptide bound to said solid phase, wherein said solid phase-bound peptide comprises a protecting group bound to an N-terminal cysteine; c) removing said protecting group from solid phase-bound peptide; (d) optionally repeating steps b) and c) with additional peptide segments comprising an N-terminal Cysteine and a C-terminal alpha thioester, wherein said additional peptide segments have a protecting group bound to their N-terminal cysteine residue (e) introducing a final peptide segment, comprising an alpha-thioester at its C-terminus, providing that if said final peptide segment comprises an N-terminal Cysteine, said N-terminal Cysteine is protected by a protecting group, wherein said introducing occurs under conditions suitable to permit ligation between said solid phase-bound peptide and said final peptide segment; and (e) optionally removing said protecting group from the N-terminal cysteine of said solid phase-bound peptide.

In another embodiment, the invention comprises a method of producing an assembled peptide having a native peptide backbone by ligating peptide segments in the C- to N-terminal direction, comprising: a) covalently binding an unprotected first peptide segment to a solid phase via a cleavable handle comprising a cleavable moiety, wherein said cleavable moiety is stable under ligation conditions and said unprotected first peptide segment is bound to said cleavable moiety at its C-terminus and has a Cysteine at its N-terminus; b) optionally introducing a second peptide segment, wherein said second segment comprises a cysteine residue at its N-terminus and an alpha-thioester at its C-terminus, and wherein said second peptide segment has a protecting group bound to its N-terminal cysteine residue, under conditions suitable to permit ligation between said first peptide segment and said second N-terminally protected peptide segment to form a natively ligated peptide bound to said solid phase, wherein said solid phase-bound peptide comprises a protecting group bound to an N-terminal cysteine, and subsequently removing said protecting group from solid phase-bound peptide; (c) optionally repeating step (b) with additional peptide segments comprising an N-terminal Cysteine and a C-terminal alpha thioester, wherein said additional peptide segments have a protecting group bound to their N-terminal cysteine residue; (d) introducing a final peptide segment, comprising an alpha-thioester at its C-terminus, providing that if said final peptide segment comprises an N-terminal Cysteine, said N-terminal Cysteine is protected by a protecting group, wherein said introducing occurs under conditions suitable to permit ligation between said solid phase-bound peptide and said final peptide segment; and (e) optionally removing said protecting group from the N-terminal cysteine of said solid phase-bound peptide.

In yet another embodiment, there is the solid phase sequential ligation of peptide segments in either or both directions, using a cleavable linker to monitor the ligation reactions via mass spectrometry and to purify the assembled peptide from the solid phase.

Another embodiment is a method of bidirectional solid phase native chemical ligation, comprising providing a first peptide segment bound to a solid support via one of its internal amino acid residues, wherein said first peptide segment comprises an N-terminal Cysteine and a C-terminal thioester, and ligating a second peptide segment to either terminus.

In another embodiment, there is provided a kit comprising an unprotected peptide segment, covalently bound via an internal amino acid side chain functional group to a cleavable handle, wherein said cleavable handle is linked to a solid phase via a chemoselective functional group complementary to a chemoselective functional group on the solid phase. Said kit can be used for solid phase chemical ligation of unprotected or N-terminal cysteine-protected peptide segments to the solid phase-bound peptide. A preferred example of such a cleavable handle is a functionalized cleavable handle, X-aminoethylsulfonylethyloxycarbonyl (wherein X=CH3COCH2CH2CH2CONHCH2-MSC- or X=AOA-NHCH2-MSC-. (AOA=aminooxyacetal).

In another embodiment, there are methods of using bromoacetic acid or iodoacetic acid to convert a peptide segment thioacid (peptide-αCOSH) to a thioester (peptide-αCOSR), on a solid phase.

In yet another embodiment, there is provided a method of monitoring the solid phase sequential ligation process on the solid phase via MALDI or ESI mass spectrometry, using cleavable linkers. Monitoring via ESI MS can also be accomplished using a TFA-cleavable linker or, when MALDI is the mass spectrometric method used, a photo-cleavable linker may preferably be used.

In a further embodiment, there are provided novel methods of preparing modular large peptide or protein libraries using combinations of the aspects of the invention described herein. Particularly useful are the methods of solid phase sequential ligation of peptide segments to rapidly synthesize multiple analogs of known proteins or polypeptides.

Kits and apparatus for assembling polypeptides and polypeptide libraries by the processes described herein are also provided.

One of skill in the art will readily appreciate that each of the embodiments of the invention can be combined with other embodiments to obtain a wide range of useful inventions.

BRIEF DESCRIPTION OF THE DRAWINGS

FIG. 1 is a schematic diagram of a solid phase native chemical ligation scheme, in the N- to C-terminus direction. In one embodiment, the linker is an MSC handle, which is cleavable yet stable under ligation conditions. In another embodiment, the unprotected first peptide segment is covalently bound to a solid phase (resin) via an aminooxy-ketone linkage.

FIG. 2A illustrates the stability of a 13-residue peptide-α-COSH with a Cysteine residue at the N-terminus under ligation conditions. The HPLC chromatogram shows that only a small percentage of the peptide cyclized or formed larger aggregates, even after overnight storage under ligation conditions.

FIG. 2B illustrates the stability of the same 13-residue peptide-αCOSH in the presence of a thioester peptide having a molecular weight of 1230.2. The HPLC chromatogram shows that the Cys-α-COSH peptide is adequately stable to use in ligation without significant reaction with itself. Furthermore, such byproducts as are formed in small proportion by reaction of the 13-residue peptide-αCOSH (having an N-terminal cysteine) with itself are unreactive with a resin-bound peptide α-COSR and are readily removed by simple filtration and washing.

FIGS. 3A, 3B and 3C show HPLC chromatograms of the effect of hydrazine on the removal of the MSC handle from a peptide having an N-terminal Cysteine residue. The peak correlating with the mass of 1708.2 represents the desired peptide with the MSC handle removed. The peak corresponding to the mass of 1814.5 represents a reactive side product formed upon cleavage that can react with the desired peptide without the MSC handle. FIG. 3A shows a fairly large peak at the 1814.5 mw when an aliquot of the peptide was placed in 6M guanidine.HCl, 0.1 M NaPi, pH 7.5, then diluted into 1 N NaOH for 2 min., then quenched with 1 N HCl. FIG. 3B is an HPLC chromatogram of the resulting product when the conditions of FIG. 3A are repeated with the inclusion of 50 mM hydrazine in the 6 M guanidine.HCl solution. FIG. 3C is an HPLC chromatogram of the resulting product when the conditions of FIG. 3A are repeated with 200 mM hydrazine in the 6 M guanidine.HCl solution. Hydrazine scavenges the side product, resulting in a purer product.

FIG. 4 is an HPLC chromatogram of the removal of a cleavable MSC handle from a peptide that does not have an N-terminal Cysteine residue, but rather an N-terminal Leucine residue and a Cysteine residue in its approximate center. The molecular weight of the peptide with the MSC handle is 4022.4 and without the MSC handle, 3745.1. An aliquot of the peptide in 6M guanidine.HCl, 0.1M NaAc, pH 4.6 was diluted into 6M guanidine.HCl, 0.1M NaAc, pH 14 for 2 min., quenched with 6M guanidine.HCl, 0.1M NaAc, pH 2.0. The HPLC shows that an internal reaction with the side product still occurs, to form the peak having a mw of 3979.7 (corresponding to the modification by the LEV-NHCH$_2$-handle), but that the extent of the reaction is less than that occurring with a peptide having an N-terminal Cysteine.

FIG. 5A is a reaction scheme showing the preparation of the PEGA resin used as the solid support in N- to C-terminal sequential ligations. Steps A and B1 are optional steps to produce a photolabile linker for use with MALDI analysis of the resin samples.

FIG. 5B is a diagram illustrating a generalized scheme for preparing a solid phase (resin) for use in the solid phase sequential ligations of the invention. Structure 1 is a cleavable linker useful for monitoring the progress of coupling and ligation reactions by mass spectrometry. For example, a photo-cleavable linker can be used for on-resin monitoring by MALDI MS, whereas a TFA cleavable linker can be used for monitoring by electrospray MS. Once structure 1 is coupled to the resin, the protecting group (PG) is removed and a functional moiety (structure 3) capable of chemoselective reaction with the first peptide segment, is added to the resin. Once 3 is coupled to the resin, the protecting group is removed to give structure 4, which is ready for chemoselective reaction with structure 5, a peptide modified with a cleavable handle and a functional group capable of reaction with the now modified resin (4). Once all subsequent ligations are complete, the "cleavable handle" is cleaved to release the full length peptide (assembled peptide) from the solid phase.

FIG. 6 is a reaction scheme illustrating the derivatization of Peptide Segment 1 (the N-terminal peptide segment).

FIGS. 7A and 7B are HPLC chromatograms of the coupling of a first unprotected peptide segment (1) to the solid support, in this example, an AOA-functionalized resin (PEGA). FIG. 7A is an HPLC of the peptide solution as added to the resin. FIG. 7B is an HPLC of the supernatant after reaction of the peptide with a molar excess of the resin overnight. A significant amount of the peptide has been removed from the supernatant, indicating that it has been bound to the resin after the overnight reaction.

FIGS. 8A and 8B are HPLC chromatograms of the same experiments reflected in FIGS. 7A and 7B, except with Isco resin beads as the solid phase.

FIGS. 9A, 9B, and 9C are analyses of the products after step 1 of this figure, binding of the first unprotected peptide segment to the solid phase. FIG. 9A is an analytical HPLC chromatogram of the (base plus hydrazine) cleavage of the resin-bound peptide. FIG. 9B is a MALDI mass spectrum of the resin, showing a peak corresponding to (1), the resin-bound peptide. FIG. 9C is a MALDI mass spectrum after base cleavage of the linker, showing the lack of a peak corresponding to (1), and showing that no peptide is sticking to the solid phase (resin).

FIGS. 10A, 10B, and 10C are analyses of the products after step 3 of this figure, i.e., ligating of the second unprotected peptide segment (2) to the resin-bound peptide (1). FIG. 10A is an analytical HPLC of the product, resin-bound peptide intermediate, showing a large peak with mass of (1)+(2). FIG. 10B is a MALDI mass spectrum of the resin before cleavage of the linker, and FIG. 10C is a MALDI mass spectrum of the resin after base cleavage of the linker.

FIG. 11 is an HPLC chromatograph of the desalted, lyophilized peptide product (1+2+3 of Table 1) after 2 sequential ligations on a solid phase (Isco resin) in the N- to C-terminal direction. The tallest peak corresponds to the crude, lyophilized product, indicating approximately 36% yield.

FIGS. 12A and 12B are ESI MS (electrospray ionization mass spectra) of the main peak corresponding to the assembled peptide (1+2+3 of Table 1). FIG. 12B is a reconstructed display of the mass spectrum of FIG. 12A, showing the mass of the product ligated peptide.

FIG. 13 is an HPLC chromatogram of the desalted, lyophilized peptide (1+2+3) after base cleavage of the linker to remove the assembled peptide from the solid phase (PEGA resin).

FIGS. 14A and 14B are electrospray ionization mass spectra of the 7434 mass peak, wherein FIG. 14B is a reconstruction of the mass spectrum of FIG. 14A.

FIGS. 15A, 15B and 15C are 3 HPLC chromatograms illustrating that the solid support technique can be used for both purification and ligation. FIGS. 15A and 15B show solution processing of a crude peptide before and after removal of DNP groups, respectively. Both HPLCs show a crude mixture of peptides. FIG. 15C is an HPLC chromatogram of the same peptide solution shown in FIG. 15A, after coupling to a solid support, removal of DNP groups and base cleavage from the solid phase, resulting in a significantly purer assembled peptide product.

FIG. 17A is a reaction scheme for the modification of the N-terminal peptide segment. FIG. 17B is a diagram illustrating the modification of the aqueous-compatible solid phase in preparation for coupling the first unprotected peptide segment.

FIG. 18A is a reaction scheme for the coupling of N-terminal modified MIF(1–59) to a solid phase. FIG. 18B is an HPLC chromatogram of the released peptide after base cleavage, having an expected mass of 6271 Da. FIGS. 18C and 18D are electrospray mass spectra of the main component of the released peptide after cleavage of the cleavable handle. FIG. 18D is a reconstruction of FIG. 18C.

FIG. 19A is a diagram of the ligation step to form resin-bound MIF(1–80). FIG. 19B is an HPLC chromatogram of the products after cleavage of the cleavable handle. FIGS. 19C and 19D are mass spectra of the main components of the released peptide after base cleavage, having an expected mass of 8502 Da. FIG. 19D is a reconstructed display of the mass spectrum of FIG. 19C.

FIG. 20A is a diagram of the ligation step to form resin-bound MIF(1–115). FIG. 20B is an HPLC chromatogram of the products after cleavage of the cleavable handle. FIG. 20C and FIG. 20D are mass spectra of the released products after base cleavage, having an expected mass of 12450 Da.

FIG. 21 is a schematic diagram of solid phase ligations in the C- to N-terminus direction. The "resin" represents a solid phase. The triangle and its sideways M-shaped partner are complementary functional groups that chemoselectively form a covalent bond. The "handle" is a cleavable handle that can be cleaved to remove the assembled peptide product from the solid phase. The undulating lines comprise amino acid residues of peptide segments. The "PG" represents a protecting group, which can be placed either on a side chain thiol or on the α-amino group of the N-terminal cysteine. Steps 2 and 3 can be repeated, as indicated by the arrow marked 4, for additional peptide segments. Also, a cleavable linker for purposes of monitoring the coupling and ligating reactions can be added between the "handle" and the "resin."

FIG. 22 is a reaction scheme for solid phase sequential ligation in the C- to N-terminal direction of PLA2G5.

FIG. 23 is a reaction scheme for synthesizing a Cam ester derivative for solid phase sequential ligation in the C- to N-terminal direction.

FIG. 24 is a reaction scheme for synthesizing the C-terminal peptide segment for solid phase sequential ligation in the C- to N-terminal direction.

FIGS. 25A, B, and C is a diagram of a scheme for synthesizing an assembled polypeptide via bidirectional solid phase sequential ligation of two or more peptide segments.

FIG. 26 are HPLC chromatographs following the solid phase solid phase native chemical ligation of 3 peptide segments in the N- to C-terminal direction, resulting in the assembled peptide, C5a 1–74.

FIG. 27 is a reaction scheme for synthesis of a C-terminal peptide segment for use in the solid phase native chemical ligations described herein, using a CAM ester cleavable handle to remove the synthesized peptide segment from the solid phase.

FIG. 28 are HPLC chromatographs and reconstructed ESI MS of the assembled peptide resulting from solid phase sequential ligation of 3 peptide segments: peptide segment 1 (CADRKNILA) (amino acids 19–27; SEQ ID NO:1), peptide segment 2 (CYGRLEEKG) (amino acids 10–18; SEQ ID NO:1) and peptide segment 3 (ALTKYGFYG) (amino acids 1–9; SEQ ID NO:1) on solid phase in the C- to N-terminal direction, using Fmoc protecting groups.

FIG. 29 are an HPLC chromatograph and ESI MS of the final ligation product, i.e. the first ligation product ligated to the third peptide segment (ALTKYGFYG) (amino acids 1–9; SEQ ID NO:1), resulting from solid phase sequential ligation of 3 peptide segments in the C- to N-terminal direction, using ACM as the protecting group.

FIGS. 30A–H are HPLC chromatographs and reconstructed ESI MS of the steps of synthesizing Phospholipase A2 Group 5, a 118 residue protein, using solid phase sequential native chemical ligation of four peptide segments in the C- to N-terminal direction. The first peptide segment is PLA2G5 88–118; the second is PLA2G5 59–87, the third is PLA2G5 26–58, and the fourth is PLA2G5 1–25.

FIGS. 30A and B are an HPLC chromatograph and reconstructed ESI MS of the first peptide segment, respectively. FIGS. 30C and D are an HPLC chromatograph and reconstructed ESI MS, respectively, of the ligation product of the first and second peptide segments (PLA2G5 59–118). FIGS. 30E and F are an an HPLC chromatograph and reconstructed ESI MS, respectively, of PLA2G5 26–118, the ligation product of PLA2G5 59–118 and PLA2G5 26–58 (the third peptide segment). FIGS. 30G and H are HPLC chromatograph and reconstructed ESI MS, respectively, of PLA2G5 1–118, the assembled polypeptide.

DESCRIPTION OF SPECIFIC EMBODIMENTS

Terminology

Figure 16A:
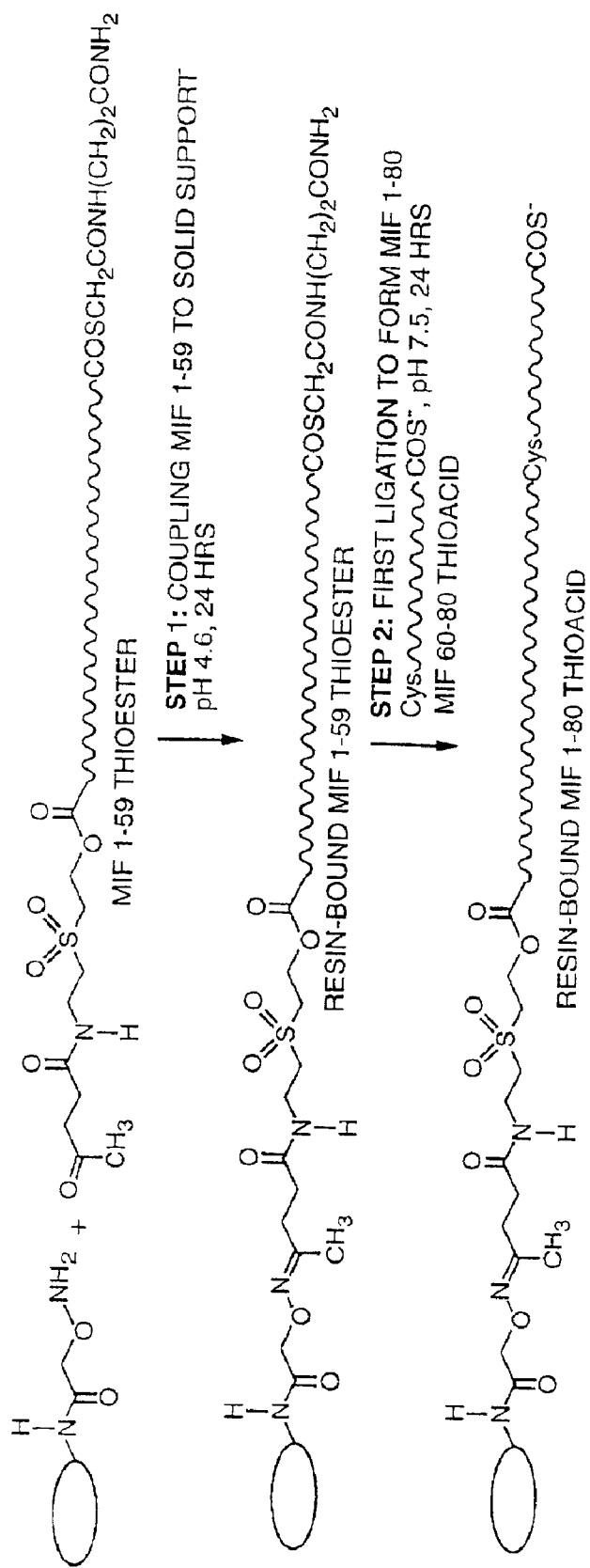
FIGS. 16A and 16B illustrate the reaction scheme for synthesis of MIF(1–115) via solid phase sequential native ligations in the N-terminal to C-terminal direction.

Amino acids: Amino acids include the 20 genetically coded amino acids, rare or unusual amino acids that are found in nature, and any of the non-naturally occurring and modified amino acids.

Aqueous solution: solutions containing water, including up to 8M urea in water, up to 6M guanidine.HCl in water, up to 60% acetonitrile in water.

Assembled Peptide: the final product of a solid phase sequential or bidirectional ligation, after cleavage of the cleavable handle. The assembled peptide comprises at least two separate peptide segments sequentially ligated on a solid phase. The assembled peptide may or may not have biological activity.

Cleavable Handle: A cleavable moiety that is capable of being selectively cleaved to release the assembled peptide from the solid phase. The cleavable handle must be capable of resisting cleavage under conditions suitable for coupling, activating, deprotecting, ligating, washing, and other steps involved in the formation of an assembled peptide. The cleavable handle must also be stable to conditions used to produce the first peptide segment that is capable of being bound to a solid phase, including, for example, stepwise solid phase peptide synthesis. The cleavable handle preferably is located directly adjacent to the first peptide segment such that upon cleavage of the cleavable handle, the desired assembled peptide is released from the solid phase. The cleavable handle may be selected from any of the variety of cleavable handles used by those in the field. See, e.g., L. Canne et al., Tetrahedron Letters, 38(19):3361–3364 (1997); Ball et al., J. Pept. Sci, 1:288–294 (1995); Funakoshi et al, PNAS USA, 88:6981–6985 (1991); Funakoshi et al., J. Chromatog. 638:21–27 (1995); Garcia-Echeverria et al., J. Chem. Soc., Chem. Commun., 779–780 (1995). A preferred cleavable handle is Boc-HN—CH2-CH2-SO2-CH2-CH2-O—CO—ONp (Boc-HNCH2-MSC-) or a functionalized cleavable handle, X-aminoethylsulfonylethyloxycarbonyl (wherein X=CH3COCH2CH2CH2CONHCH2-MSC- or X=AOA-NHCH2-MSC-). (AOA=aminooxyacetal). Another preferred cleavable handle is a CAM ester. See Ceccato, M. L. et al., Tetrahedron Lett. 31:6189–6192 (1990).

Cleavable Linker: A cleavable moiety that is capable of being selectively cleaved to monitor the solid phase sequential ligation using mass spectrometry of small samples of the reaction mixture at any point during the ligation procedure, i.e. after ligating of the second peptide segment, after ligating of the third peptide segment, and so forth. The cleavable linker must be stable under coupling and ligating conditions, deprotecting conditions (if needed), and washing conditions. Preferred cleavable linkers include photolabile linkers and TFA-labile linkers.

Coupling: Chemoselective reactions involving covalent binding of a first peptide segment to a solid phase.

Ligating: Chemoselective reactions involving covalent binding of a peptide segment to a solid phase-bound peptide.

Linker: A covalent linkage linking various moieties. For example, a linker may link a first peptide segment and a solid support, and such a linker may optionally comprises any number of moieties, including a cleavable handle, a cleavable linker, complementary functional groups capable chemoselectively forming a covalent bond (e.g., amino-oxy and ketone to form an oxime).

Peptide: A polymer of at least two monomers, wherein the monomers are amino acids, sometimes referred to as amino acid residues, which are joined together via an amide bond. For purposes of this invention, the terms "peptide," "polypeptide," and "protein," are largely interchangeable as all three types can be made via the methods described herein. Peptides are alternatively referred to as polypeptides. Amino acids include the L and D isoforms of chiral amino acids.

Peptide segment: A peptide or polypeptide, having either a completely native amide backbone or an unnatural backbone or a mixture thereof, ranging in size from 2 to 1000 amino acid residues, preferably from 2–99 amino acid residues, more preferably from 10–60 amino acid residues, and most preferably from 20–40 amino acid residues. Each peptide segment can comprise native amide bonds or any of the known unnatural peptide backbones or a mixture thereof. Each peptide segment can be prepared by any known synthetic methods, including solution synthesis, stepwise solid phase synthesis, segment condensation, and convergent condensation. The final peptide segment to be added to form the assembled peptide product can be recombinantly expressed.

Protecting Group: A chemical moiety capable of protecting a functional group from reacting with another functional group, and removable without damage to the formed amino acid or peptide.

Sequential ligation: ligating three or more peptide segments together in order from C-terminus to N-terminus or from the N-terminus to C-terminus, depending on the directionality chosen, to obtain an assembled peptide product. The directionality of the sequential ligations will always start from the solid phase-bound first peptide segment to the last peptide segment to be added to form the assembled peptide product.

Solid Phase: A material having a surface and which is substantially insoluble when exposed to organic or aqueous solutions used for coupling, deprotecting, and cleavage reactions. Examples of solid phase materials include glass, polymers and resins, including polyacrylamide, PEG, polystyrene PEG-A, PEG-polystyrene, macroporous, POROS™, cellulose, reconstituted cellulose (e.g. Perloza), nitrocellulose, nylon membranes, controlled-pore glass beads, acrylamide gels, polystyrene, activated dextran, agarose, polyethylene, functionalized plastics, glass, silicon, aluminum, steel, iron, copper, nickel and gold. Such materials may be in the form of a plate, sheet, petri dish, beads, pellets, disks, or other convenient forms. Sheets of cellulose can be used as a solid phase in the present invention to accomplish spot ligation in a spatially addressable array. Many of the examples and embodiments described herein refer to resins, which are a type of solid phase, and one of ordinary skill in the art would understand that such examples are not meant to be limited to resins, but to solid phases in general. The terms solid phase and solid support are used herein interchangeably.

Solid Phase-bound Peptide: a solid phase-bound peptide comprises at least one peptide segment bound to a solid phase via any variety of cleavable linkers, handles or moieties. A solid phase-bound peptide can include any of the intermediate peptide products of the sequential ligation reactions, including the final solid-phase bound peptide produced after the final peptide segment is ligated to the penultimate solid phase-bound peptide.

Thioacid: An ionizable thioacid moiety, represented by either —COSH or —COS⁻, often referring to a peptide thioacid, represented by "peptide α-COSH" or "peptide α-COS⁻."

Thioester: A moiety represented by —COSR, often connected to a peptide. For example, a peptide thioester may be represented as "peptide α-COSR". The R group may be any number of groups, including 1–15 C functionalized alkyl, straight or branched, 1–15 C aromatic structures, 1–4 amino acids or derivatives thereof, preferably wherein the R group is selected such that the peptide-alpha-COSR is an activated thioester. In a preferred embodiment, R=—CH3-Ø, -Ø. The term "thioester" is commonly used, but the true IUPAC term is "thioloester." See Matthys J. Janssen, supra I. Solid Phase Sequential Native Ligation of Unprotected Peptide Segments in the N- to C-Terminal Direction There have been few reports of proteins synthesized by sequential, multiple ligations of three or more unprotected peptide segments. Such sequential ligations of free peptide segments in solution consequently require a purification (e.g. HPLC) after each ligation and typically require temporary protection of one of the functionalities of the middle segments.

One aspect of the present invention is a solid phase sequential ligation technique which avoids the need for multiple purifications and the need to temporarily protect the middle peptide segments. This strategy employs (1) the modification of the N-terminal peptide segment with a cleavable handle functionalized with a group capable of chemoselective reaction with the solid support and (2) sequential native chemical ligations of unprotected peptide segments in an N- to C-terminal direction. Native chemical ligation involves reaction of an unprotected peptide segment bearing a C-terminal α-thioester with a second unprotected peptide segment containing an N-terminal Cysteine residue. Thiol exchange yields a thioester-linked intermediate which spontaneously rearranges to a native amide bond at the ligation site. We have determined that a peptide segment bearing an N-terminal Cysteine and a C-terminal thioacid is sufficiently stable under native ligation conditions that it requires no temporary protection of the C-terminal thioacid functionality. Accordingly, these peptide segments can be used as the middle segments in a sequential ligation scheme involving three or more peptide segments as shown in FIG. 1. Once such a middle segment has ligated to the solid phase-bound thioester-containing peptide to generate a solid phase-bound peptide thioacid, the thioacid is easily converted to a thioester and can be reacted with the N-terminal Cysteine of the next peptide segment to be ligated. Alternatively, the incoming peptide segment may have an internal amino acid with a nonnatural side chain bearing amino and thiol moieties on adjacent c atoms, i.e. in a 1,2 relation to one another, and an unreactive, unprotected non-cysteine amino acid residue at its N-terminus, which would lead to a nonlinear assembled peptide. Multiple ligations of distinct peptide segments to form an assembled peptide bound to the solid phase are contemplated. Once all ligations are complete, the linker binding the solid phase-bound peptide to the solid phase is cleaved, releasing the assembled peptide, i.e., the full length peptide. This technique is applied to the total chemical synthesis of a random peptide of artificial sequence (Table 1 in Examples Section), and human Macrophage Migration Inhibitory Factor (MIF), a 115 amino acid cytokine involved in immune system function. See FIGS. 16–20.

A. Peptide Synthesis

Peptide segments were synthesized in stepwise fashion by established machine-assisted solid-phase methods on polystyrene resins using in situ neutralization/HBTU activation protocols for Boc chemistry (L. Canne et al., Tetrahedron Lett. 38:3361–3364 (1997)) on Boc-aminoacyl $OCH_2$-PAM resins, thioester-generating resins (Hojo, et al., Bull. Chem. Soc. Jpn. 64:111–117 (1991)), or thioacid-generating resins. After chain assembly was complete, peptides were deprotected and simultaneously cleaved from the resin by treatment with anhydrous HF containing 5% p-cresol, lyophilized, and purified by preparative HPLC. The N-terminal peptide segment was modified prior to HF cleavage as outlined in FIG. 17A.

B. Preparation of the Solid Phase

The solid phase is prepared as depicted in FIGS. 5A and 5B. FIG. 5A is a scheme for preparing PEGA resin as a solid support. FIG. 5B is a generalized diagram for the preparation of any solid phase. An amino-Spherilose™ (Isco) affinity resin was derivatized with Boc-aminooxyacetic acid as shown in FIG. 17B.

Other resins to be used as the solid phase include EAH Sepharose (Pharmacia), Amino PEGA (Novabiochem), CLEAR base resin (Peptides International), long chain alkylamine controlled pore glass (Sigma), HCl.PEG polystyrene (PerSeptive Biosystems), Lysine Hyper D resin (Biosepra), ArgoGel Base resin (Argonaut Technologies). These resins are available in amino-derivatized form or are readily converted to amino-derivatized form.

C. Coupling of Modified N-Terminal Peptide Segment to Solid Phase

The modified peptide, containing a ketone moiety, as depicted in FIG. 17A, is dissolved in 6M guanidine.HCl, 0.1M Na acetate, 0.15M methionine, pH 4.6 (1.6 mM) and added to the aminooxy functionalized solid support, which had previously been thoroughly washed in the same buffer, and allowed to react at room temperature overnight (FIG. 16A, Step #1).

II. Ligation in the N- to C-Terminal Direction

Figure 16B:
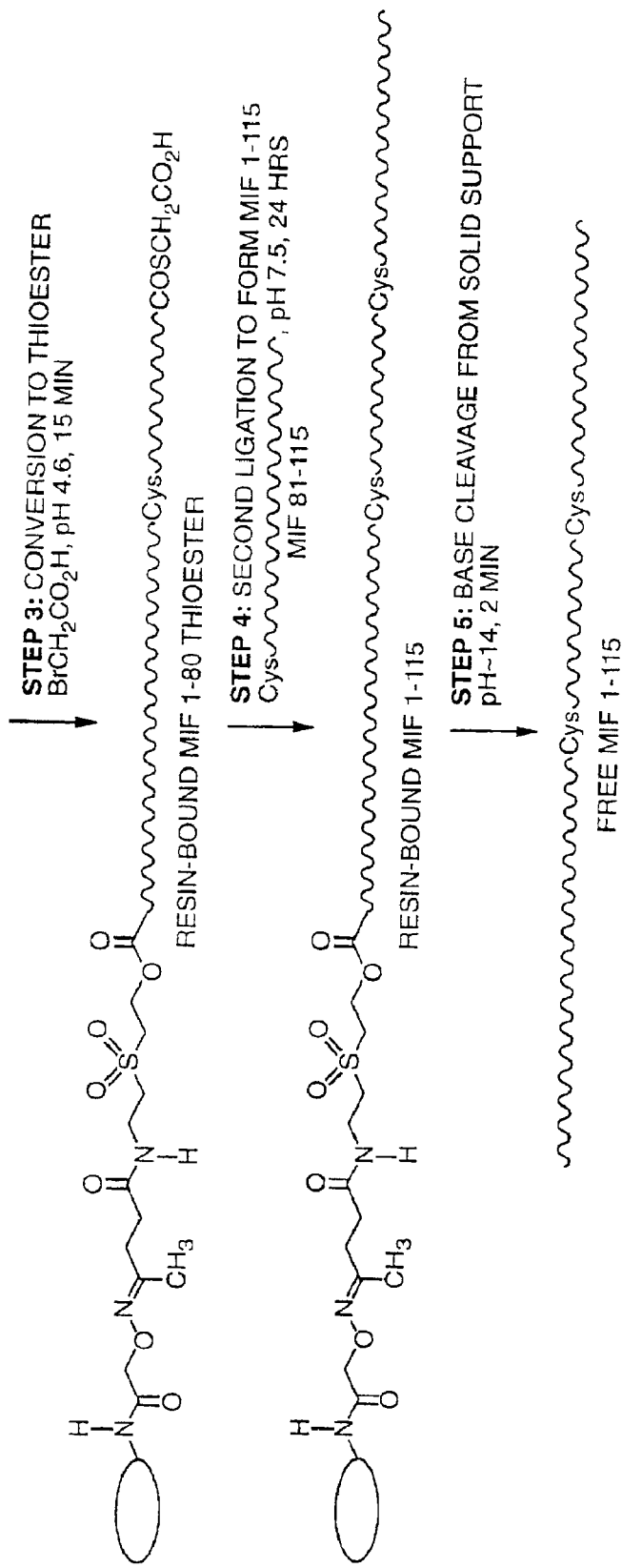

A. Ligation Reactions. The peptide segment to be ligated to the resin-bound peptide thioester was dissolved in 6M guanidine.HCl, 0.1M Na acetate, 0.15M methionine, 0.5% thiophenol, pH 7.5 (3.7–4.0 mM) and added to the resin bound peptide thioester, which was thoroughly washed in the same buffer, and allowed to react at room temperature overnight (FIGS. 16A and 16B, Steps #2 and 4). Preferably the concentration of the first peptide segment can range from 1 to 150 mM; more preferably from 5–100 mM, most preferably from 10–50 mM, depending on the particular peptide segment.

One of skill in the art will understand that concentrations of the first peptide segment and the second and other incoming peptide segments can be optimized using routine experimentation. Concentrations of the second and additional incoming peptide segments can range from 1–200 mM, more preferably from 5–100 mM, and most preferably from 10–59 mM, depending on the particular peptide segment.

Excess first peptide segment and/or excess incoming peptide segments can be readily removed from the solid phase bound peptide by filtration and washing.

B. Conversion of Thioacid to Thioester Using Bromoacetic Acid or Iodoacetic Acid The use of Bromoacetic acid or Iodoacetic acid is an improved method of generating peptide-αCOSR thioesters from peptide-αCOSH thioacids. In order to insure solubility of long unprotected peptides, 6 M guanidine-HCL at near pH 4 is used. Reactions is carried out near pH 4. Under such conditions, the only group reactive with Bromoacetic acid or Iodoacetic acid is the thioacid. Benzyl bromide, a hydrophobic compound, does not dissolve completely in solution, resulting in slow and heterogeneous reactions. The advantages of using bromoacetic acid or iodoacetic acid are that both are readily soluble in 6 M guanidine-HCL (an aqueous solution) at near pH 4, both result in quick completion of the desired reaction, both elute in the void volume of typical reverse-phase HPLC, and allow processing of large amounts of peptide segments.

The resin-bound peptide thioacid is thoroughly washed in 6M guanidine.HCl, 0.1M Na acetate, 0.15M methionine, pH 4.6 and treated with a 50 mM solution of bromoacetic acid in the same buffer for 15 min, followed by thorough washing with the pH 4.6 buffer (FIG. 16B, Step #3).

C. Cleavage from the Solid Phase

Cleavable handles useful in the ligations in the N- to C-terminal direction must be capable of being stable to ligation conditions, stable to stepwise solid phase chemistries, able to be covalently linked in unprotected form to the solid phase, and be cleavable without damaging the assembled polypeptide. Any cleavable handles satisfying these requirements can be used, including, but not limited to: MSC handle, photolabile linkers, CAM esters (—OCHCONH—), (—O—CH2-Ø-SO—CH2-CO—), (—O—CRH—CO-Ø-O—CH2-CO—). For example, (—O—CH2-Ø-SO—CH2-CO—) may be used as a handle cleavable under any of the following conditions: (1) HF, DMS; (2) SciCl4, TFA; or red of Sulfoxide and TFA cleavage; (3) NaOH, water; or (4) red of sulfoxide and TBAF in DMF. See Samamen, J. M., J. Org. Chem. 53:561 (1988). As another example, the (—O—CRH—CO-Ø-O—CH2-CO—) may be used as a cleavable handle under any of the following conditions: (1) NaOH, water (CAM Linker); (2) ZnCH3COOH/Water; (3) photolysis. See Tjoeng et al., Synthesis 897 (1981); Sheehan et al., J. Org. Chem. 38:3771 (1973); Serebryakov et al., Tetrahedron 34:345 (1978); Hendrickson et al., Tetrahedron Lett. 343 (1970); Ceccato, M. L. et al., Tetrahedron Lett. 31:6189–6192 (1990); J. Martinez et al., Tetrahedron Lett. 41:739 (1985). One of skill in the art will readily appreciate the suitability of known cleavable handles for the purposes described herein.

The following conditions can be used for cleavage of the linker to release the assembled polypeptide from the solid phase, particularly when an MSC handle is used. Aliquots of resin-bound peptide are treated with 6M guanidine.HCl, 0.1M Na acetate, 0.15M methionine, containing 200 mM hydrazine, at pH~14 for 2 min, followed by washing with an equal amount of 6M guanidine.HCl, 0.1 M Na acetate, 0.15M methionine, pH~2 and an equal amount of 6M guanidine.HCl, 0.1M Na acetate, 0.15M methionine, pH4.6. The combined eluants of free peptide are analyzed by analytical HPLC and electrospray mass spectrometry (FIG. 16B, Step #5).

II. Solid Phase Ligations in the C- to N-Terminal Direction

The discussion regarding N- to C-terminal ligations above applies equally well to C- to N-terminal ligations, except, as shown in FIG. 23, that: (1) the first peptide segment is bound to the solid phase via its C-terminus, i.e. the C-terminal peptide segment of the resulting assembled polypeptide is the one modified with a cleavable handle and (2) the incoming (i.e. second, third, additional) peptide segments do require temporary protection of their N-terminal Cysteine (see steps 2–4). Optionally, all Cysteine residues of the incoming or middle peptide segments can be temporarily protected along with the N-terminal Cysteine.

As outlined in the scheme (FIG. 23), the C-terminal peptide segment bearing a cleavable handle is coupled to the solid support by reaction with a corresponding functional group on the solid support (e.g. resin), for example, through an oxime linkage (aminooxyacetyl group on the resin and a ketone [via levulinic acid] on the peptide), or the reverse (aminooxyacetyl group on the peptide and a ketone on the solid phase).

Once the first peptide segment is bound to the solid phase as shown in step 1 of FIG. 21, the incoming (second) peptide segment, comprising an N-terminal protected Cys (PG-Cys) and a C-terminal thioester, reacts with the N-terminal unprotected Cys of the resin-bound first peptide segment through the native chemical ligation reaction. After ligation is complete, the protecting group of the N-terminal Cys is removed (step 3 of FIG. 21), and the next peptide segment is added (step 4/2 of FIG. 21). Once all ligations are complete (step 5 of FIG. 21), the handle attaching the sequentially ligated peptide to the resin is cleaved, releasing the full length peptide. This C- to N-terminal technique is applied to the total chemical synthesis of a random peptide of artifical sequence and to human secretory phospholipase A2, group 5 ("PLA2G5"), a 118 amino acid enzyme, as described below.

A. Peptide Synthesis

Peptide synthesis for solid phase sequential native chemical ligation in the C- to N-terminal direction is essentially the same as described above for solid phase sequential native chemical ligation in the N- to C-terminal direction.

See Example 7 below for details re stepwise solid phase peptide synthesis of the peptide segments.

B. Preparation of the Solid Phase

Preparation of the solid phase for the C- to N-terminal direction is identical to that described for the N- to C-terminal direction.

C. Coupling of the Modified C-Terminal Peptide Segment to Solid Phase

Conditions for coupling the modified C-terminal peptide segment to the solid support can be identical to that outlined for coupling of the modified N-terminal peptide in the N- to C-terminal ligations as described above.

D. Ligation in the C- to N-Terminal Direction

Conditions for the native chemical ligation reactions in the C- to N-terminal direction can be identical to that outlined for N- to C-terminal ligations as described above, except that the N-terminal cysteine containing peptide segment is solid phase bound and the incoming thioester containing peptide segment is in solution.

E. Cysteine Protecting Groups and Removal

Any of the known protecting groups suitable for protecting the N-terminal Cys of a peptide segment can be used, provided that they are stable to ligation conditions, stable to conditions for adding the linker, and removable from the peptide segment under conditions that are not harmful to the solid-phase bound peptide, the linker, the resin, or the cleavable handle, if used. The protecting groups must also be stable to stepwise solid phase peptide synthesis conditions. An example of a protecting group is ACM (Acetamidomethyl), which provides cysteine side chain protection (—SCH2NHCOCH3), and can be cleaved with mercury(II)acetate, or other suitable reagents. Fmoc (9Fluorenylmethylcarbamate) provides alpha amino protection, can be cleaved in 20% piperidine in DMF and works well with hydrophilic peptides. DNPE (2-(2,4-dinitriphenyl)ethyl) provides cysteine side chain protection and cleaves in 50% piperidine in DMF. Para-nitrobenzensulfonyl provides alpha-amino protection, and is cleaved in 1 M DBU/1 M beta-mercaptoethanol in DMF. Additional cysteine protecting groups include, but are not limited to, Sulfmoc, NSC, Dde, Boc-Cys(Acm)-OH, Fmoc-Cys-(Mob)-OH, Boc-Cys(Fm)-OH, and Boc-Cys(DNPE)-OH, wherein Acm=acetamidomethyl, Mob=methoxybenzyl, Dnpe=2-(2,4-dinitrophenyl)ethyl, Fm=9-fluorenylmethyl. See Protective Groups inOrganic Synthesis, Green, T. W. and Wuts, P. G. M. eds, (2d Ed. 1991), particularly p. 293–294, 318–319; R. Merrifield, J. Org. Chem. 43:4808–4816 (1978); V. V. Samukov et al., Tetrahedron Lett. 35:7821–7824 (1994); B. W. Bycroft et al., J. Chem. Soc. Chem. Comm. 776–777 (1993); M. Royo et al., Tetrahedron Lett., 33:2391–2394 (1992); S. C. Miller, J. Am. Chem. Soc. 119:2301–2302 (1997). Certain protecting groups can make peptide segments insoluble. For example, certain hydrophobic peptide segments may become insoluble upon addition of a protecting group. One of ordinary skill in the art can readily ascertain the suitability of any particular protecting group for a peptide segment.

Removal of Fmoc as a Cys Protecting Group. One embodiment involves removal of an Fmoc protecting group from the N-terminal Cys of a solid-phase bound peptide. After ligation with a peptide with an N-terminal Fmoc-Cys, the resin bound peptide is washed with 6 M guanidine.HCl, 0.1 M NaPi, 0.15 M methionine, pH 7, followed by water, followed by DMF. The resin is then treated with two aliquots of 20% piperidine in DMF, 5 minutes each. The resin is then washed thoroughly with DMF, followed by water, followed by 6 M guanidine.HCl, 0.1 M NaPi, 0.15 M methionine, pH 7.

Removal of ACM as a Cys Protecting Group. After ligation with a peptide with an N-terminal Cys(ACM), the resin bound peptide is washed with 6 M guanidine.HCl, 0.1 M NaPi, 0.15 M methionine, pH 7, followed by 3% aqueous acetic acid. The resin is then treated with a solution of mercury(II)acetate in 3% aqueous acetic acid (15 mgs/ml) for 30 minutes, followed by washing with 3% aqueous acetic acid. The resin is then washed with 6 M guanidine.HCl, 0.1 M NaPi, 0.15 M methionine, pH 7, followed by treatment with 20% beta-mercaptoethanol in 6 M guanidine.HCl, 0.1 M NaPi, 0.15 M methionine, pH 7 for 30 min. The resin is then washed with 6 M guanidine.HCl, 0.1 M NaPi, 0.15 M methionine, pH 7.

F. Cleavage from the Solid Phase

Cleavable handles are used to cleave the solid-phase bound peptide from the solid phase for ligations in the N- to C-terminal direction, in the C- to N-terminal direction, and in the bidirectional approach (both N- to C-terminal ligation and C- to N-terminal ligation). For solid phase sequential native chemical ligations in the C- to N-terminal direction (and for bidirectional ligations using C- to N-terminal ligation), the requirements of cleavable handle are the same as for those useful in the N- to C-terminal direction, with the additional requirement that the cleavable handle be stable under conditions used for removal of the protecting group from the N-terminal cysteine of the solid-phase bound peptide.

Cleavage of a peptide-CAM ester linkage to the solid phase. Aliquots of resin-bound peptide are washed with 8M urea, 0.1M NaPi, pH 7, followed by treatment for 2 minutes with 0.25N NaOH in the same 8M urea buffer (resulting pH~14). The resin is then washed with an equal amount of 0.25N HCl in the same 8M urea buffer (resulting pH~2), followed by thorough washing with the 8M urea buffer. The combined eluants of free peptide are analyzed by HPLC and electrospray mass spectrometry.

III. Bidirectional Solid Phase Sequential Native Chemical Ligation

Yet another embodiment of the invention relates to bidirectional solid phase protein synthesis that incorporates aspects of both the N- to C-terminus and C- to N-terminus sequential solid phase protein synthesis approaches. In the bidirectional approach, a peptide segment having either or both an N-terminal Cysteine and/or a C-terminal thioester is attached to a solid phase via a side chain of one of its amino acid residues. See FIG. 25A, B, C. The peptide segment can then be ligated at either terminus to a second peptide segment, followed by ligation at the other terminus to a third peptide segment. In this bidirectional approach, if the peptide segment attached to the solid phase has both a protected N-terminal Cysteine and a C-terminal thioester, second and third peptide segments can be added at both ends in subsequent ligations. Additional peptide segments can then be added at either end of the ligated, solid phase bound peptide. The ligations in either direction are accomplished using the methods, described herein for ligations in either the C- to N-terminal direction or the N- to C-terminal direction.

Alternatively, the first peptide segment attached via one of its internal amino acid residues to the solid phase can be used for only uni-directional ligations. For example, the peptide segment attached to the solid phase can be ligated to a second peptide segment at one terminus, followed by one or more ligations to additional peptide segments at the same terminus of the second peptide segment. In this embodiment, the peptide segment bound to the solid phase can be used for either sequential solid phase native chemical ligations in the C- to N-terminal direction or for sequential solid phase native chemical ligations in the N- to C-terminal direction. In this embodiment, the peptide segment bound to the solid phase can be bidirectionally capable (i.e. having both a protected N-terminal Cysteine and a C-terminal thioester) while being used for unidirectional sequential ligations (i.e. having either a protected N-terminal Cysteine or a C-terminal thioester).

The first peptide segment is bound to the solid phase via a side chain of one of its amino acid residues, which is bound to a cleavable handle, which is bound to the solid phase via a functional chemical moiety that is capable of chemoselectively forming a covalent bond with a complementary functional chemical moiety on the solid phase, as illustrated in FIG. 25.

For example, the first peptide segment can be bound to the solid phase via the side chains of a lysine, aspartic acid or glutamic acid, in which case a cleavable handle based on functionalities, such as allyloxycarbonyl (alloc) or Fmoc, i.e. cleavable under orthogonal conditions, may be used to connect the peptide segment to the solid phase via the side chain of its lysine, aspartic acid or glutamic acid. As another example, an oxime bond may be formed by the first peptide segment and the solid phase, wherein the first peptide segment comprises either an amino-oxy or ketone chemoselective functional group and the solid phase comprises a complementary chemoselective functional group, such as a ketone or amino-oxy, respectively.

IV. Use of Cleavable Linkers and Mass Spectrometry to Monitor Ligation Reactions Various known cleavable linkers can be used to monitor the solid phase sequential ligations. These cleavable linkers are placed between the solid phase and the first peptide segment which is covalently bound to the cleavable handle, e.g. solid phase—cleavable linker—cleavable handle—peptide segment. The cleavable linkers are capable of being readily cleaved to permit mass spectrometric analysis of a small portion of solid phase-bound peptide to monitor the coupling and ligation reactions.

For example, when the solid phase consists of resin beads, one can take a few resin beads from the reaction mixture after the coupling reaction or after each ligation reaction to determine the extent of reaction. Particularly preferred cleavable linkers include photolabile cleavable linkers for MALDI mass spectrometry, including 3-nitro-4 (methylamino)benzoyl-. See FIG. 5A. A small aliquot of the reaction mixture is removed for MALDI MS analysis and dried on a slide in mixture with a matrix solution. The laser of the MALDI mass spectrometer cleaves the photolabile linker on the mass spectrometer's stage, permitting mass analysis of the released peptides.

Another preferred cleavable linker is one that is cleavable by TFA (trifluoroacetic acid), which is useful for electrospray ionization mass spectrometry. With TFA-cleavable linkers, the peptides are cleaved from the solid phase prior to ESI MS.

EXAMPLES

Example 1

Preparation of the Solid Phase for N- to C-Terminal Ligations

The preparation of the solid phase is schematically diagrammed in FIG. 5. The solid phase is a resin, for example, Amino PEGA (0.2–0.4 mmol/g swelled in methanol) or an amino-Spherilose affinity resin (15–20 Tmol/ml, 0.6–0.9 mmol/g dry resin), available from Pharmacia, NovaSyn or Isco. The resin (PEGA or Isco) is washed with DMF (dimethylformamide), then is washed briefly with 10% DIEA (diisopropyl ethylamine). Two 30 sec DMF flow washes are used. A photocleavable linker (PCL) (See FIG. 5A) is activated with one equivalent of HBTU (2-(1H-benzotriazol-1-yl)-1,1,3,3-tetramethyl-uronium hexafluorophosphate) and DIEA in DMF for 5–10 min). This activated photocleavable linker is then added to the resin and is left standing at room temperature for ~3 hrs (ninhydrin can be used with Isco).
Two 30 sec. DMF flow washes are used, followed by TFA (1 min×2), and two more 30 sec. DMF flow washes. The remaining steps are in abbreviated form:
   10% DIEA (1 min×2)
   DMF flow wash (30 sec×2)
   addition of activated Boc-aminooxyacetic acid (activated with one equivalent DIC and N-hydroxysuccinimide in DMF for 30–60 min)
   left standing at room temperature for ~1 hr (ninhydrin can be used with Isco)
   DMF flow wash (30 sec×2) [resin can be stored at this stage]
   TFA (1 min×30)
   DMF flow wash (30 sec×2)
   10% DIEA (1 in×2)
   DMF flow wash (30 sec×2)
   thorough washing with aqueous buffer (6 M GuHCl, 0.1 M Na Acetate, pH 4.6) (1 ml×5)

Example 2

Preparation of the First Unprotected Peptide Segment for N- to C-Terminal Ligations The following procedures are used to prepare the first peptide segment (N-terminus), which is diagrammed in FIGS. 6, 7A and 7B.
   The peptide-resin is swelled in DMF
   TFA (1 min×2)
   DMF flow wash (30 sec×2)
   10% DIEA (1 min×2)
   DMF flow wash (30 sec×2)
   Addition of MSC handle in DMF
   leave standing at room temperature for 1 hr
   add DIEA and leave standing for another hr
   use ninhydrin test to verify adequate coupling
   DMF flow wash (30 sec×2)
   TFA (1min×2)
   DMF flow wash (30 sec×2)
   10% DIEA (1 min×2)
   DMF flow wash (30 sec×2)
   addition of activated levulinic acid (activated as the symmetric anhydride with 0.5 equivalents of DIC in DCM for 5–10 min)
   leave standing at room temperature for 30 min
   ninhydrin test to verify adequate ligating
   DMF flow wash (30 sec×2)
   thorough washing with DCM
   dry on lyophilizer
   HF cleavage at 0° C. for 1 hr using p-cresol as a scavenger
   trituration and washing with cold ethyl acetate
   dissolve in 50% B and lyophilize
   purify by preparative HPLC

TABLE 1

Solid Phase Sequential Ligations: N- to C-Terminal
3-Random Peptide Segment Model System Lev-MSC-LTEGLHGFHVHEFGDNTAGCTSAGPHFNPLSRKHG-COS) (1) +
Resin-PCL-ONH$_2$
↓ 1. pH 4.6, 6M GuHCl, 0.1 M acetate
Resin-PCL-oxime-MSC-LTEGLHGFHVHEFGDNTAGCTSAGPHFNPLSRKHG-COS) (1)
↓ 2. pH 4.6, 6M GuHCl, 0.1 M acetate, 50 mM BrAcOH
Resin-PCL-oxime-MSC-LTEGLHGFHVHEFGDNTAGCTSAGPHFNPLSRKHG-COSAc (1) +
H-CGFRVREFGDNTA-COS) (2)
↓ 3. pH 7.5, 6M GuHCl, 0.1M phosphate, 0.5% thiophenol
Resin-PCL-oxime-MSC-LTEGLHGFHVHEFGDNTAGCTSAGPHFNPLSRKHG
CGFRVREF-GDNTA-COS) (1 + 2)
↓ 4. pH 4.6, 6M GuHCl, 0.1M acetate, 50 mM BrAcOH
Resin-PCL-oxime-MSC-LTEGLHGFHVHEFGDNTAGCTSAGPHFNPLSRKHG
CGFRVREF-GDNTA-COSAc (1 + 2) +
H-CADPSEEWVQKYVSDLELSA-OH (3)
↓ 5. pH 7.5, 6M GuHCl, 0.1M phosphate, 0.5% thiophenol
Resin-PCL-oxime-MSC-LTEGLHGFHVHEFGDNTAGCTSAGPHFNPLSRKHG
CGFRVREF-GDNTACADPSEEWVQKYVSDLELSA-OH (1 + 2 + 3)
↓ 6. pH 14, 6M GuHCl, 0.1M phosphate, 200 mM hydrazine
H-LTEGLHGFHVHEFGDNTAGCTSAGPHFNPLSRKHGCGFRVREF-
GDNTACADPSEEWVQKYVSDLELSA-OH (1 + 2 + 3)

PCL = photocleavable linker

Example 3

Solid Phase Native Chemical Ligation of Random Peptide Segments in Aqueous Solution in the N- to C-Terminus Direction The following procedures are used for solid phase ligations in the N- to C-terminus direction, as diagrammed in Table 1. General principals of native chemical ligation are described in WO 96/34878, PCT/US95/05668, incorporated herein by reference.

The resin is washed with 6 M guanidine.HCl, 0.1 M Na Acetate, pH 4.6 (1 ml×5) and drained. The modified N-terminal peptide segment is dissolved in 6 M guanidine.HCl, 0.1 M Na Acetate, pH 4.6 and added to resin and is left standing at room temperature overnight. (The concentration of the first segment is at least 5 mM). The next morning, resin is washed with 6 M guanidine.HCl, 0.1 M Na Acetate, pH 4.6 (1 ml×5) and drained. A sample of resin is removed for MALDI MS analysis and is washed with 50% B, MeOH, DCM and dried. A sample of resin is removed for base cleavage and is treated with 200 µl 6 M guanidine.HCl, 0.1 M Na Pi, 200 mM hydrazine, pH~14 for 2 min and drained, resin is washed with 200 µl 6 M guanidine.HCl, 0.1 M Na acetate, 200 mM hydrazine, pH~2 and with 200 µl 6 M guanidine.HCl, 0.1 M Na Acetate, pH 4.6 and the combined eluants treated with TCEP prior to injection on HPLC.

In preparation for addition of the next peptide segment, the resin is washed with 6 M guanidine.HCl, 0.1 M Na Pi, pH 7.5 (1 ml×5) and drained. The second peptide segment (Cys—COSH) is dissolved in 6 M guanidine.HCl, 0.1 M Na Pi, pH 7.5, 0.5% thiophenol and added to resin. This mixture is left standing at room temperature overnight. The next morning, the resin is washed with 6 M guanidine.HCl, 0.1 M Na Acetate, pH 4.6 (1 ml×5) and drained. Samples of resin are removed for Maldi and base cleavage and treated as above.

The solid phase-bound peptide is then converted from COSH to COSAc by treating the resin with 50 mM BrAcOH in 6 M guanidine.HCl, 0.1 M Na Acetate, pH 4.6 for 15 min.

The resin is washed with 6 M guanidine.HCl, 0.1 M Na Acetate, pH 4.6 (1 ml×5) and drained.

In preparation for addition of the next peptide segment, the resin is washed with 6 M guanidine.HCl, 0.1 M Na Pi, pH 7.5 (1 ml×5) and drained. The final peptide segment is dissolved in 6 M guanidine.HCl, 0.1 M Na Pi, pH 7.5, 0.5% thiophenol and added to resin. This reaction mixture is left standing at room temperature overnight. The next morning, the resin is washed with 6 M guanidine.HCl, 0.1 M Na Acetate, pH 4.6 (1 ml×5) and drained. A sample of resin are removed for monitoring by MALDI MS analysis.

The assembled peptide is removed from the solid phase via base cleavage of the cleavable handle from the remaining resin as outlined above only on a larger scale followed by purification by HPLC or desalting on PD-10 column and lyophilization.

Example 4

Solid Phase Native Chemical Ligation of C5a (1–74) (74aa) in the N- to C-Terminal Direction This example describes solid phase sequential native chemical ligation in the N- to C-terminal direction of C5a, Complement Factor 5A. The sequence of C5a is: (SEQ ID NO. ?) TLQKKIEEEIAAKYKJSVVKKCCYD-GACVNNDETCEQRAARISLGPKCIKAF-TECCVVASQLRANISHKDMQLGR (SEQ ID NO:3).

This peptide is prepared using solid phase sequential native ligation of 3 peptide segments: C5a(1–20), C5a(21–46), and C5a(47–74). The procedures used to synthesize C5a by solid phase ligations are identical to those described in the solid phase sequential native ligation of MIF (See Example 5).

Example 5

Solid Phase Sequential Native Chemical Ligation of MIF(1–115) (115 aa) in the N-Terminal to C-Terminal Direction The sequence of MIF(1–115): MPMFIVNTNVPRASVP-DGFLSELTQQLAQATGKPPQYIAVHVVP-DQLMAFGGSSEPCAL CSLHSIGKIGGAQNR-SYSKLLCGLLAERLRISPDRVYINYYDMNAASVG WNNSTFA (SEQ ID NO:4). This peptide is prepared using solid phase sequential native ligation of 3 peptide segments: MIF(1–59) (amino acid 1–59, SEQ ID NO:4) MIF(60–80) (amino acid 60–80, SEQ ID NO:4) and MIF(81–115) (amino acid 81–115, SEQ ID NO:4). See FIGS. 16–20.

Step #1: The first unprotected peptide segment, MIF (1–59) is coupled to a solid phase as depicted in FIG. 18. The coupling conditions are 6M guanidine.HCl, 0.1M NaAcetate, 0.15M Methionine, pH 4.6, 24 hours.

The MSC handle used is:

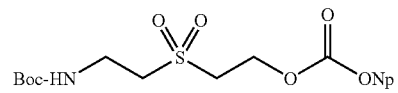

This cleavable handle is based on methylsulfonylethyloxycarbonyl (MSC) amine protecting group. It is easily added to unprotected amino terminus of peptide-resins, survives HF deprotection and cleavage from the resin, is quickly and cleanly cleaved by aqueous base, and is designed with a protected amine which can be derivatized with a variety of functionalities.

Step #2: The second unprotected peptide segment (Cys60-MIF(61–80)-COSH) is then ligated to the solid phase-bound first unprotected peptide segment, under the conditions 6 M guanidine.HCl, 0.1M NaPi, 0.5% thiophenol, 0.15M Methionine, pH 7.5, 24 hours.

Step #3: The solid phase-bound peptide, MIF(1–80)-COSH, is then activated to the thioester under the following conditions: 50 mM BrCH2COOH, 6M guanidine.HCl, 0.1M NaAcetate, 0.15M Methionine, pH 4.6, 15 min.

Step #4: The third unprotected peptide segment (Cys81-MIF82–115-COOH) is ligated to the solid phase-bound peptide with 6 M guanidine.HCl, 0.1M NaPi, 0.5% thiophenol, 0.15M Methionine, pH 7.5, 24 hours.

Step #5: The MIF(1–115) bound to the solid phase is then cleaved from the solid support by base cleavage of the cleavable handle under the cleaving conditions: 6 M guanidine.HCl, 0.1M NaAcetate, 0.15M Methionine, 200 mM hydrazine, at pH~14 for 2 min., followed by 6 M guanidine.HCl, 0.1M NaAcetate, 0.15M Methionine, 200 mM hydrazine, at pH~2. The expected mass of the assembled peptide MIF(1–115) released upon base cleavage is 12450 Da. FIGS. 20C and 20D are mass spectra of the assembled peptide having an expected mass of 12450. FIG. 20D is a reconstruction of the mass spectrum of FIG. 20C. FIG. 20B is an HPLC chromatogram of the assembled peptide.

Example 6

Solid Phase Native Chemical Ligation of Phospholipase A2, Group 5(1–118) (118aa) in the C- to N-Terminal Direction The sequence of Phospholipase A2, group 5 (PLA2G5) is: GLLDLKSMIEKVTGKNALTNYGFYGCY-CGWGGRGTPKDGTDWCCWAHDHCYGRLEE KGC-NIRTQSYKYRFAWGVVTCEPGPFCHVNL-CACDRKLVYCLKRNLRSYNPQYQYFPNILCS (SEQ ID NO:5).

This peptide is prepared using solid phase sequential native ligation of 4 peptide segments: PLA2G5 (1–25), PLA2G5 (26–58), PLA2G5(59–87) and PLA2G5 (88–118). The procedures used to synthesize PLA2G5 by solid phase ligations are identical to those used for synthesizing the random sequence using ACM protection of the N-terminal Cys residues of the middle segments, as described in Example 9. See FIG. 22 for the reaction scheme. The Cam ester derivative is synthesized and incorporated into the C-terminal peptide segment according to the diagrams in FIG. 23, 24/FIG. 27. The assembled polypeptide, PLA2G5 (1–118), was folded and assayed for biological activity. It had the full activity of a recombinantly expressed PLA2G5.

Example 7

Preparation of Modified C-Terminal Peptide Segment (On-Resin CAM Linker Synthesis) (FIG. 27)

The commerical resin of choice (MBHA, any Boc-AA-OCH2-Pam resin) is swelled in DMF
TFA (1 min×2) (not necessary if working with MBHA resin)
DMF flow wash (30 sec×2)
addition of activated Boc-Lys(Fmoc)-OH (HBTU/DIEA activation), check for completion of reaction after 10–15 minutes by ninhydrin test
DMF flow wash (30 sec×2)
TFA (1 min×2)
DMF flow wash (30 sec×2)
10% DIEA in DMF (1 min×2)
addition of activated bromoacetic acid (activated as the symmetric anhydride with 0.5 equivalents of DIC in DCM for 5–10 minutes), check for completion of reaction after 30 minutes by ninhydrin test
DMF flow wash (30 sec×2)
addition of first Boc-protected amino acid of the sequence (Boc-AA-OH) 2M in 20% DIEA in DMF. Leave standing at room temperature for 3 hrs.
DMF flow wash (30 sec×2)
synthesize rest of the sequence by standard protocols for Boc chemistry
remove Fmoc group by treating with 20% piperidine in DMF (5 min×2)
DMF flow wash (30 sec×2)
addition of activated levulinic acid (activated as the symmetric anhydride with 0.5 equivalents of DIC in DCM for 5–10 min), check for completion of reaction after 30 minutes by ninhydrin test
DMF flow wash (30 sec×2)
thorough washing with DCM
thoroughly dry resin
HF cleavage at 0° C. for 1 hr using p-cresol as a scavenger
trituration and washing with cold ethyl ether
dissolve in aqueous HPLC buffer and lyophilize
purify by preparative HPLC

Example 8

Solid Phase Native Chemical Ligation of Random Peptide Segments in the C- to N-Terminal Direction Using Fmoc Protection (See FIG. 28)

The following procedures can be used for solid phase ligations in the C- to N-terminal direction, as diagramed in Table 2. By example, a random peptide of: ALTKYGFYG-CYGRLEEKGCADRKNILA (SEQ ID NO:1) can be ligated in three peptide segments (from C- to N-terminal direction): segment 1=CADRKNILA (amino acids 19–27; SEQ ID NO:1); segment 2=CYGRLEEKG (amino acids 10–18; SEQ ID NO:1); and segment 3=ALTKYGFYG (amino acids 1–9; SEQ ID NO:1).

The resin is washed with 6M Gu.HCL, 0.1M Na Acetate, pH 4.6 (1 ml×5) and drained. The modified C-terminal peptide segment (first peptide segment) is dissolved in 6M Gu.HCL, 0.1M Na Acetate, pH 4.6 (5 mM first peptide segment) and added to the resin and is left standing at room temperature overnight. The resin is washed with 6M Gu.HCL, 0.1M Na Acetate, pH 4.6 (1 ml×5) and drained. A sample is removed for base cleavage and is treated with 8M urea, 0.1M NaPi, pH 7, treated for 2 minutes with 0.25N NaOH in the same 8M urea buffer (resulting pH~14), washed with an equal amount of 0.25N HCl in the same 8M urea buffer (resulting pH~2), and the combined eluants treated with TCEP prior to injection on HPLC.

In preparation for addition of the next segment, the resin is washed with 6M Gu.HCl, 0.1M NaPi, pH 7.0 (1 ml×5) and drained. The second peptide segment (Fmoc-Cys-peptide-COSR) is dissolved in 6M Gu.HCl, 0.1M NaPi, pH 7.0, 0.5% thiophenol (to at least 10 mM to 50 mM second peptide segment) and added to the resin. The mixture is left standing at room temperature overnight. The resin is washed with 6M Gu.HCl, 0.1M NaPi, pH 7.0 (1 ml×5), water (1 ml×5), DMF (1 ml×5), and the Fmoc protecting group removed by treating with two aliquots of 20% piperidine in DMF (5 min each). The resin is then washed with DMF (1 ml×5), water (1 ml×5), and 6M Gu.HCl, 0.1M NaPi, pH 7.0 (1 ml×5). A sample of resin is removed and base cleaved as above.

The final peptide segment is dissolved in 6M Gu.HCl, 0.1M NaPi, pH 7.0, 0.5% thiophenol and added to the resin. This mixture is left standing at room temperature overnight. The resin is then washed with 6M Gu.HCl, 0.1M NaPi, pH 7.0 and the assembled peptide is removed from the solid phase via base cleavage of the cleavable handle from the remaining resin as outlined above only on a larger scale followed by purification by HPLC or deslating on PD-10 column and lyophilization.

These methods can be applied to make any peptides having cysteine residues.

Example 8A

Solid Phase Native Chemical Ligation of Random Peptide Segments in the C- to N-Terminal Direction Using DNPE Protection DNPE (2-(2,4-dinitrophenylethyl)) is another cysteine side chain protecting group which can be used for ligations in the C- to N-terminal direction. Example 8 was repeated using DNPE as the protecting group. The conditions for solid phase chemical ligation of random peptide segments in the C- to N-terminal direction were identical to those used for Example 8 above except that in the removal of the DNPE protecting group, 50% piperidine is used.

Example 9

Solid Phase Native Chemical Ligation of Random Peptide Segments in the C- to N-Terminal Direction Using ACM Protection The following procedures are used for solid phase ligations in the C- to N-terminal direction, as diagramed in Table 3. The same random polypeptide described in the Example above is ligated.

The resin is washed with 6M Gu.HCL, 0.1M Na Acetate, pH 4.6 (1 ml×5) and drained. The modified C-terminal peptide segment is dissolved in 6M Gu.HCL, 0.1M Na Acetate, pH 4.6 and added to the resin and is left standing at room temperature overnight. The resin is washed with 6M Gu.HCL, 0.1M Na Acetate, pH 4.6 (1 ml×5) and drained. A sample is removed for base cleavage and is treated with 8M urea, 0.1M NaPi, pH 7, treated for 2 minutes with 0.25N NaOH in the same 8M urea buffer (resulting pH~14), washed with an equal amount of 0.25N HCl in the same 8M urea buffer (resulting pH~2), and the combined eluants treated with TCEP prior to injection on HPLC.

In preparation for addition of the next segment, the resin is washed with 6M Gu.HCl, 0.1M NaPi, pH 7.0 (1 ml×5) and drained. The second peptide segment (Fmoc-Cys-peptide-COSR) is dissolved in 6M Gu.HCl, 0.1M NaPi, pH 7.0, 0.5% thiophenol (to at least 10 mM second peptide segment) and added to the resin. The mixture is left standing at room temperature overnight. The resin is washed with 6M Gu.HCl, 0.1M NaPi, pH 7.0 (1 ml×5), 3% acetic acid in water (1 ml×5), and the ACM protecting group removed by treating with mercury(II)acetate in 3% acetic acid in water (15 mgs/ml) for 30 min. The resin is then washed with 3% acetic acid in water (1 ml×5), 6M Gu.HCl, 0.1M NaPi, pH 7.0 (1 ml×5), and treated with 20% beta-mercaptoethanol in 6M Gu.HCl, 0.1M NaPi, pH 7.0 for 30 min, followed by washing with 6M Gu.HCl, 0.1M NaPi, pH 7.0 (1 ml×5). A sample of resin is removed and base cleaved as above.

The final peptide segment is dissolved in 6M Gu.HCl, 0.1M NaPi, pH 7.0, 0.5% thiophenol and added to the resin. This mixture is left standing at room temperature overnight. The resin is then washed with 6M Gu.HCl, 0.1M NaPi, pH 7.0 and the assembled peptide is removed from the solid phase via base cleavage of the cleavable handle from the remaining resin as outlined above only on a larger scale followed by purification by HPLC or desalting on PD-10 column and lyophilization.

TABLE 2

Polymer-Supported Ligations
C- to N- Terminal Direction
Fmoc Protection

H-CADRKNILA-CAM-Lys(Levulinic acid)-NH2 (1) +
Resin- ONH₂
↓ 1. pH 4.6, 6M Gu.HCl, 0.1 acetate
H-CADRKNILA-CAM-Lys-oxime-Resin (1) +
Fmoc-CYGRLEEKG-COSR (2)
↓ 2. pH 7.5, 6M Gu.HCl, 0.1M phosphate, 0.5% thiophenol
Fmoc-CYGRLEEKGCADRKNILA-CAM-Lys-oxime-Resin (1 + 2)
↓ 3. 20% piperidine/DMF
H-CYGRLEEKGCADRKNILA-CAM-Lys-oxime-Resin (1 + 2) +
H-ALTKYGFYG-COSR (3)
↓ 4. pH 7.5, 6M Gu.HCl, 0.1M phosphate, 0.5% thiophenol
H-ALTKYGFYGCYGRLEEKGCADRKNILA-CAM-Lys-oxime-Resin (1 + 2 + 3)
↓ 5. pH 14, 8M Urea, 0.1M phosphate, 0.25N NaOH
H-ALTKYGFYGCYGRLEEKGCADRKNILA-OH

TABLE 3

Polymer-Supported Ligations
C- to N- Terminal Direction
ACM Protection

H-CADRKNILA-CAM-Lys(Levulinic acid)-NH2 (1) +
Resin- ONH₂
↓ 1. pH 4.6, 6M Gu.HCl, 0.1 acetate
H-CADRKNILA-CAM-Lys-oxime-Resin (1) +
H-C(ACM)YGRLEEKG-COSR (2)
↓ 2. pH 7.5, 6M Gu.HCl, 0.1M phosphate, 0.5% thiophenol
H-C(ACM)YGRLEEKGCADRKNILA-CAM-Lys-oxime-Resin (1 + 2)
↓ 3. a. mercury(II)acetate in 3% Aq. AcOH
    b. 20% mercaptoethanol in pH 7.5, 6M Gu.HCl, 0.1M phosphate
H-CYGRLEEKGCADRKNILA-CAM-Lys-oxime-Resin (1 + 2) +
H-ALTKYGFYG-COSR (3)
↓ 4. pH 7.5, 6M Gu.HCl, 0.1M phosphate, 0.5% thiophenol
H-ALTKYGFYGCYGRLEEKGCADRKNILA-CAM-Lys-oxime-Resin (1 + 2 + 3)
↓ 5. pH 14, 8M Urea, 0.1M phosphate, 0.25N NaOH
H-ALTKYGFYGCYGRLEEKGCADRKNILA-OH

Example 10

Bidirectional Solid Phase Sequential Native Chemical Ligation

This example illustrates one of the embodiments of the bidirectional solid phase protein ligation approach, namely the situation starting with a first peptide segment bound to the solid phase, wherein the first peptide segment is a "middle piece" of the target protein desired, i.e. the first peptide segment, bound to the solid phase, is used for ligations at both its N-terminal Cysteine and its C-terminal thioester.

Starting with one of the middle pieces of the target protein, a cleavable linker is added to the side chain of one of the amino acid residues of the middle piece. The side chain of any amino acid residue having a protectable functional group can be used, including, preferably Aspartic Acid or Glutamic Acid. Most preferably, a Lysine amino acid residue is used. For example, a CAM ester cleavable handle or any other carboxylic acid protecting group may be adapted to attach the first peptide segment to the solid phase through the side chain of Aspartic or Glutamic Acid. One of skill in the art will readily appreciate the necessary chemistries for accomplishing this step.

For example, the synthesis of a first peptide segment to be attached to the solid phase via an internal amino acid is illustrated in FIG. 25C. Starting with an appropriate solid phase (thioester or thiacid generating), the first peptide segment is synthesized using standard Boc protocols until the Lysine residue of choice is reached. Using Boc chemistry, a Lysine with its side chain amine protected with an Fmoc group (Boc-Lys(Fmoc)-OH) is inserted at the appropriate location during solid phase stepwise peptide synthesis, followed by continued synthesis to the end of the first peptide segment. The Fmoc protecting group is removed at the end of the stepwise peptide synthesis and the cleavable handle coupled to the side chain amine (step B of FIG. 25C).

This method is much the same as the procedure outlined in FIG. 24, with the following differences: the levulinic acid in step 4 is replaced with the cleavable handle and the 20% piperidine used to cleave the Fmoc group (also part of step 4) is replaced with a much smaller concentration of an alternative base such as 1,8-Diazabicyclo[5.4.0]undec-7-ene (DBU), e.g. 1–2 equivalents of DBU in DMF. The reason is the middle peptide segments, regardless of whether they generate thioacids or thioesters upon cleavage from the resin, are connected to the resin by a thioester which would be cleaved in the presence of 20% piperidine.

For this particular strategy, the MSC handle is preferred, although other cleavable handles can be used. Attachment to the side chain amine of a lysine residue and further modification of the linker with an appropriate functional group capable of reacting with a corresponding group on the solid phase ligation resin would be generally as outlined in FIG. 17A, with the exception that the amine of the MSC handle should be protected with an Fmoc instead of a Boc group. Since attachment to the peptide segment is through an internal amino acid residue, the N-terminal amino acid would be Boc protected and it is not possible for the N-terminal amino group and the amino group of the MSC cleavable handle to be protected by the same group. Removal of the Fmoc group on the MSC cleavable handle would also need to be done with DBU instead of piperidine. As in FIG. 17A, levulinic acid is preferred for coupling to the linker with a corresponding aminooxyacetyl group on the solid support (FIG. 17B).

Two versions of the first peptide segment to be coupled to the resin are described below.

First Version. The first peptide segment has an unprotected N-terminal cysteine and a C-terminal thioacid (FIG. 25A). The second peptide segment (step 2. in FIG. 25A), to be ligated to the first peptide segment, is a peptide with a C-terminal thioester and optionally a protected N-terminal Cysteine (if additional C- to N-terminal ligations are desired), wherein the C-terminal thioester is capable of reacting with the N-terminal Cys of the first peptide segment (i.e. in the C- to N-terminal direction). This step can be multiply repeated with additional peptide segments added in the C- to N-terminal direction, if desired, provided that the internal incoming peptide segments each comprise a protected N-terminal Cysteine, which can be deprotected according to the standard C- to N-terminal solid phase native chemical ligation steps outlined in FIG. 21 (the final peptide segment to be added at the N-terminus of the resulting product need not have an N-terminal Cysteine). After ligation is complete, the C-terminal thioacid of the resulting solid-phase bound peptide (i.e. ligation product of first and second peptide segments) is then converted to a thioester with bromoacetic acid (as outlined in N- to C-terminal ligations in Table 1 and diagrammed as step 3 of FIG. 25A). The next step (step 4 of FIG. 25A) comprises ligation of the solid-phase bound peptide to a third peptide segment with an N-terminal Cys. This step can optionally be repeated, to add additional incoming peptide segments in the N- to C-terminal direction, if desired, provided that the internal incoming peptide segments each comprise an unprotected N-terminal Cysteine and a C-terminal thioacid, with conversion of the thioacid to thioester after the ligation is complete and prior to addition of the next peptide segment. The final peptide segment to be added at the C-terminus of the resulting product need not have a C-terminal thioacid.

One of skill in the art will appreciate that multiple ligations can subsequently be performed in both directions if the appropriate protecting groups and other appropriate chemistries are used on the middle piece or the solid-phase bound peptide. These additional steps are identical to the strategies used for the individual directions, i.e. N-terminal unprotected Cys plus C-terminal thioester for the N- to C-direction and N-terminal Cys(ACM) plus C-terminal thioester for the C- to N-terminal direction. Assuming the MSC linker is used, cleavage of the full length product from the resin would be in basic solution (pH 12–14) as outlined in step 6 in Table 1. However, the preferred approach is to complete all ligation steps necessary for one direction, followed by the ligation steps for the other direction. As long as the solid phase bound peptide has either a protected N-terminal Cysteine or a C-terminal thioacid, ligations can proceed in either direction provided that the appropriate strategies as described herein are followed. If the solid phase bound peptide has both an unprotected N-terminal Cysteine and a C-terminal thioester, any attempts at ligating to an additional incoming peptide segment will result in cyclization of the solid-phase bound peptide.

Second Version. The second version of this scheme involves starting with ligation in the N- to C-terminal direction, followed by ligation in the opposite direction, as shown in FIG. 25B. The first peptide segment to be coupled to the resin comprises a temporarily protected N-terminal Cys and a C-terminal thioester. The ligation of a second peptide segment to the first peptide segment is then in the N- to C-terminal direction. Any subsequent ligations in the C- to N-terminal direction would first require removal of the protecting group.

Except for the attachment of the first peptide segment to the solid support, this strategy merely combines the procedures for N- to C- and C- to N-terminal ligations (described above).

REFERENCES

S. Funakoshi et al., Chemoselective one-step purification method for peptides synthesized by the solid-phase technique, Proc. Nat. Acad. Sci. USA, 88:6981–6985 (August 1991).

S. Funakoshi et al., Affinity purification method using a reversible biotinylating reagent for peptides synthesized by the solid-phase technique, J. Chromatog. 638:21–27 (1993).

M. Mutter et al., Pseudo-prolines (psi Pro) for accessing inaccessible peptides, Pept. Res. 8(3):145–153 (1995).

M. Baca et al., Chemical ligation of cysteine-containing peptides: synthesis of a 22 kDa tethered dimer of HIV-1 protease, J. Am. Chem. Soc. 117(7):1881–1887 (1995).

J. Camarero et al., Chemical Ligation of Unprotected Peptides Directly From a Solid Support, J. Peptide Res. 51:303–316 (1998).

L. Canne et al., Total Chemical Synthesis of a Unique Transcription Factor-Related Protein: cMyc-Max, J. Am. Chem. Soc. 117:2998–3007 (1995).

C. Cho et al., An Unnatural Biopolymer, Science 261:1303–1305 (1993).

P. Dawson et al., Synthesis of Proteins by Native Chemical Ligation, Science 266:776–779 (1994).

N. Fotouhi et al., J. Org. Chem. 54:2803–2817 (1989).

G. Barany and R. B. Merrifield, A New Amino Protecting Group Removal by Reduction. Chemistry of the Dithiasuccinoyl (Dts) Function, J. Am. Chem. Soc., 99(22) :7363–7365 (1977).

C. Hennard and J. Tam, Sequential Orthogonal Coupling Strategy for the Synthesis of Biotin Tagged β Defensin, Abstract P118, Fifteenth American Peptide Symposium, Jun. 14–19, 1997.

C. Hyde et al., Some difficult sequences made easy, A study of interchain association in solid-phase peptide synthesis, Int. J. Peptide Protein Res. 43:431–440 (1994).

W. Lu et al., Biochemistry, 36(4):673–679 (1997).

C.-F. Liu and J. Tam, Peptide segment ligation strategy without use of protecting groups, Proc. Nat. Acad. Sci. USA, 91:6584–6588 (1994).

C.-F. Liu and J. Tam, Chemical ligation approach to form a peptide bond between unprotected peptide segments. Concept and model study, J. Am. Chem. Soc. 116(10):4149–4153 (1994). Schnolzer et al., Science 256:221–225 (1992).

Rose et al. J. Am Chem. Soc. 116:30–34 (1994).

Liu et al., Proc. Natl. Acad. Sci. USA 91:6584–6588 (1994).

Dawson et al. Science 266:77–779 (1994).

PCT/US95/05668, WO 96/34878.

Sakakibara S., Biopolymers (Peptide Science), 37:17–28 (1995).

Tam et al., PNAS USA, 92:12485–12489 (1995).

T. Muir, A Chemical approach to the construction of multimeric protein assemblies, Structure 3:649–652 (1995).

R. Merrifield, Solid Phase Peptide Synthesis: The Synthesis of a Tetrapeptide, J. Am. Chem. Soc., 85:2149–2154 (1963).

H. Muramatsu et al., Localization of Heparin-Binding, Neurite Outgrowth and Antigenic Regions in Midkine Molecule, Biochem. And Biophys. Res. Commn. 203(2):1131–1139 (1994).

PCT/US94/07222, WO 95/00846, Published Jan. 5, 1995.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. An apparatus for producing assembled polypeptides, said apparatus comprising a reaction vessel containing as components:
   (a) a solid phase support having bound thereto a plurality of first peptides, said first peptides comprising partially or completely unprotected peptides having an N-terminus that is bound to said solid phase support via a cleavable handle, and a C-terminus that comprises a thioacid or a thioester;
   (b) a plurality of second peptides comprising partially or completely unprotected peptides having an N-terminal cysteine and a C-terminal thioester or thioacid.

2. The apparatus of claim 1, wherein the C-terminus of said first peptides comprises a thioacid.

3. The apparatus of claim 1, wherein the C-terminus of said first peptides comprises a thioester.

4. The apparatus of claim 1, wherein the C-terminus of said second peptides comprises a thioacid.

5. The apparatus of claim 1, wherein the C-terminus of said second peptides comprises a thioester.

6. The apparatus of claim 1, wherein said solid phase support is a bead resin.

7. The apparatus of claim 1, wherein said first peptides and said second peptides range in size from 5 to 99 amino acid residues.

8. The apparatus of claim 1, wherein said first peptides and said second peptides are prepared by solid phase synthesis.

9. The apparatus of claim 1, wherein at least one of said plurality of first peptides and said plurality of second peptides comprises peptides having an unnatural backbone structure.

10. An apparatus for preparing assembled polypeptides, said apparatus comprising a reaction vessel containing as components:
   a) a solid phase support having bound thereto a plurality of first peptides, said first peptides comprising partially or completely unprotected peptides having a C-terminus that is bound to said solid phase support via a cleavable linkage and an N-terminus that comprises a cysteine residue;
   b) a plurality of second peptides comprising partially or completely unprotected peptides having an N-terminal cysteine and a C-terminal thioacid or thioester.

11. The apparatus of claim 10, wherein said plurality of second peptides is comprised of peptides having the same length, but different amino acid sequences.

12. The apparatus of claim 10, wherein said plurality of second peptides consists essentially of identical peptides.

13. The apparatus of claim 10, wherein the C-terminus of said first peptides comprises a thioacid.

14. The apparatus of claim 10, wherein the C-terminus of said first peptides comprises a thioester.

15. The apparatus of claim 10, wherein the C-terminus of said second peptides comprises a thioacid.

16. The apparatus of claim 10, wherein the C-terminus of said second peptides comprises a thioester.

17. The apparatus of claim 10, wherein said solid phase support is a bead resin.

18. The apparatus of claim 10, wherein said first peptides and said second peptides range in size from 5 to 99 amino acid residues.

19. The apparatus of claim 10, wherein said first peptides and said second peptides are prepared by solid phase synthesis.

20. The apparatus of claim 10, wherein at least one of said plurality of first peptides and said plurality of second peptides comprises peptides having an unnatural backbone structure.

* * * * *

SEQUENCE LISTING

<160> NUMBER OF SEQ ID NOS: 6

<210> SEQ ID NO 1
<211> LENGTH: 27
<212> TYPE: PRT
<213> ORGANISM: Artificial Sequence
<220> FEATURE:
<223> OTHER INFORMATION: Description of Artificial Sequence:synthetic

<400> SEQUENCE: 1

Ala Leu Thr Lys Tyr Gly Phe Tyr Gly Cys Tyr Gly Arg Leu Glu Glu
 1               5                  10                  15

Lys Gly Cys Ala Asp Arg Lys Asn Ile Leu Ala
            20                  25

<210> SEQ ID NO 2
<211> LENGTH: 68
<212> TYPE: PRT
<213> ORGANISM: Artificial Sequence
<220> FEATURE:
<223> OTHER INFORMATION: Description of Artificial Sequence:synthetic

<400> SEQUENCE: 2

Leu Thr Glu Gly Leu His Gly Phe His Val His Glu Phe Gly Asp Asn
 1               5                  10                  15

Thr Ala Gly Cys Thr Ser Ala Gly Pro His Phe Asn Pro Leu Ser Arg
            20                  25                  30

Lys His Gly Cys Gly Phe Arg Val Arg Glu Phe Gly Asp Asn Thr Ala
        35                  40                  45

Cys Ala Asp Pro Ser Glu Glu Trp Val Gln Lys Tyr Val Ser Asp Leu
    50                  55                  60

Glu Leu Ser Ala
65

<210> SEQ ID NO 3
<211> LENGTH: 73
<212> TYPE: PRT
<213> ORGANISM: Homo sapiens

<400> SEQUENCE: 3

```
Thr Leu Gln Lys Lys Ile Glu Ile Ala Ala Lys Tyr Lys Ser Val
 1               5                  10                 15

Val Lys Lys Cys Cys Tyr Asp Gly Ala Cys Val Asn Asn Asp Glu Thr
                20                  25                 30

Cys Glu Gln Arg Ala Ala Arg Ile Ser Leu Gly Pro Lys Cys Ile Lys
            35                  40                  45

Ala Phe Thr Glu Cys Cys Val Val Ala Ser Gln Leu Arg Ala Asn Ile
    50                  55                  60

Ser His Lys Asp Met Gln Leu Gly Arg
65              70
```

<210> SEQ ID NO 4
<211> LENGTH: 115
<212> TYPE: PRT
<213> ORGANISM: Homo sapiens

<400> SEQUENCE: 4

```
Met Pro Met Phe Ile Val Asn Thr Asn Val Pro Arg Ala Ser Val Pro
 1               5                  10                 15

Asp Gly Phe Leu Ser Glu Leu Thr Gln Gln Leu Ala Gln Ala Thr Gly
                20                  25                 30

Lys Pro Pro Gln Tyr Ile Ala Val His Val Val Pro Asp Gln Leu Met
            35                  40                  45

Ala Phe Gly Gly Ser Ser Glu Pro Cys Ala Leu Cys Ser Leu His Ser
    50                  55                  60

Ile Gly Lys Ile Gly Gly Ala Gln Asn Arg Ser Tyr Ser Lys Leu Leu
65              70                  75                  80

Cys Gly Leu Leu Ala Glu Arg Leu Arg Ile Ser Pro Asp Arg Val Tyr
                85                  90                  95

Ile Asn Tyr Tyr Asp Met Asn Ala Ala Ser Val Gly Trp Asn Asn Ser
                100                 105                110

Thr Phe Ala
    115
```

<210> SEQ ID NO 5
<211> LENGTH: 118
<212> TYPE: PRT
<213> ORGANISM: Homo sapiens

<400> SEQUENCE: 5

```
Gly Leu Leu Asp Leu Lys Ser Met Ile Glu Lys Val Thr Gly Lys Asn
 1               5                  10                 15

Ala Leu Thr Asn Tyr Gly Phe Tyr Gly Cys Tyr Cys Gly Trp Gly Gly
                20                  25                 30

Arg Gly Thr Pro Lys Asp Gly Thr Asp Trp Cys Cys Trp Ala His Asp
            35                  40                  45

His Cys Tyr Gly Arg Leu Glu Glu Lys Gly Cys Asn Ile Arg Thr Gln
    50                  55                  60

Ser Tyr Lys Tyr Arg Phe Ala Trp Gly Val Val Thr Cys Glu Pro Gly
65              70                  75                  80

Pro Phe Cys His Val Asn Leu Cys Ala Cys Asp Arg Lys Leu Val Tyr
                85                  90                  95

Cys Leu Lys Arg Asn Leu Arg Ser Tyr Asn Pro Gln Tyr Gln Tyr Phe
                100                 105                110

Pro Asn Ile Leu Cys Ser
    115
```

```
<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence:synthetic

<400> SEQUENCE: 6

Asp Ser Val Ile Ser Leu Ser Gly Asp His
 1               5                  10
```